(12) United States Patent
Nitsch et al.

(10) Patent No.: US 7,494,645 B2
(45) Date of Patent: Feb. 24, 2009

(54) LIPID PHOSPHATE PHOSPHATASES AND USES THEREOF FOR TREATING NEURONAL DISEASES

(75) Inventors: Robert Nitsch, Berlin (DE); Olaf Ninnemann, Wensickendorf (DE); Anja U. Bräuer, Berlin (DE); Nicolai E. Savaskan, Berlin (DE)

(73) Assignee: Charite Universitaetsmedzin-Berlin, Berlin (DE)

( * ) Notice: Subject to any disclaimer, the term of this patent is extended or adjusted under 35 U.S.C. 154(b) by 0 days.

(21) Appl. No.: 10/527,646

(22) PCT Filed: Sep. 15, 2003

(86) PCT No.: PCT/EP03/10228

§ 371 (c)(1),
(2), (4) Date: Jun. 28, 2005

(87) PCT Pub. No.: WO2004/033691

PCT Pub. Date: Apr. 22, 2004

(65) Prior Publication Data

US 2006/0166202 A1    Jul. 27, 2006

(30) Foreign Application Priority Data

Sep. 13, 2002    (EP) ................... 02020679
Feb. 11, 2003    (EP) ................... 03002993

(51) Int. Cl.
*C12N 9/16* (2006.01)
*C12Q 1/68* (2006.01)
*C12P 21/06* (2006.01)
*A61K 38/00* (2006.01)
*A61K 38/46* (2006.01)
*C07H 21/04* (2006.01)

(52) U.S. Cl. .................. 424/94.6; 435/6; 435/69.1; 435/196; 514/2; 536/23.2

(58) Field of Classification Search ................. 435/196; 536/23.2
See application file for complete search history.

(56) References Cited

FOREIGN PATENT DOCUMENTS

| WO | WO 01/59063 A | 8/2001 |
|---|---|---|
| WO | WO 02/22660 A | 3/2002 |
| WO | WO 02/092798 A | 11/2002 |
| WO | WO 03/057870 A | 7/2003 |

OTHER PUBLICATIONS

Database EMBL [Online] Jul. 27, 2002, Database accession No. ABB97308.
Database EBI [Online] Mar. 10, 2001, Database accession No. AL136596.
Database EBI [Online] Jun. 16, 2001, Database accession No. BC009378.
Database EBI [Online] Dec. 10, 2001, Database accession No. BC018242.
Database EMBL [Online] Aug. 6, 2002, Database accession No. AK056665.
Database EMBL [Online] Nov. 30, 2000, Database accession No. BB594581.
Database EMBL [Online] Oct. 20, 2001, Database accession No. BB633873.
Database EMBL [Online] Jul. 12, 2002, Database accession No. AL834390.
Database EMBL [Online] Jan. 23, 2002, Database accession No. ABB14761.
Database EMBL [Online] Jan. 23, 2002, Database accession No. ABA146530.
Database EMBL [Online] Jan. 23, 2002, Database accession No. ABA14531.
Database EMBL [Online] Dec. 21 2002, Database accession No. AK043762.
Tigyi Gabor et al., "Lysophosphatidic acid-induced neurite retraction in PC12 cells: Control by phosphoinositide-Ca-2+signaling and Rho", *Journal of Neurochemistry*, vol. 66, No. 2, 1996, pp. 537-548.
Hooks et al. "Lysophosphatidic acid-induced mitogenesis is regulated by lipid phosphate phosphatases and is Edg-receptor independent", *Journal of Biological Chemistry*, vol. 276, No. 7, Feb. 16, 2001, pp. 4611-4621.
Brindley D N et al., "Lipid phosphate phosphatases regulate signal transduction through glycerolipids and sphingolipids", *Biochimica and Biophysica ACTA. Molecular and Cell Biology of Lipids*, vol. 1582, No. 1-3, May 23, 2002, pp. 33-44.
Fukushima et al., "Lysophosphatidic acid (LPA) is a novel extracellular regulator of cortical neuroblast morphology", *Developmental Biology*, vol. 228, No. 1, Dec. 1, 2000, pp. 6-18.
Brauer et al., "A new phospholipid phosphatase, PRG-1, is involved in axon growth and regenerative sprouting", *Nature Neuroscience*, vol. 6, No. 6, Jun. 20, 2003, pp. 572-578.

*Primary Examiner*—Rebecca E Prouty
*Assistant Examiner*—Iqbal H Chowdhury
(74) *Attorney, Agent, or Firm*—Nixon Peabody LLP

(57) ABSTRACT

Lipid phosphate phosphatase proteins, genes coding for them, vectors and cells comprising them, antibodies directed against them, methods of identifying compounds binding to them and functional interactors as well as to the use of proteins, genes, vectors, cells, interacting compounds and functional interactors for treating neuronal diseases and/or injuries.

2 Claims, 16 Drawing Sheets

Figure 1

A

Figure 3:
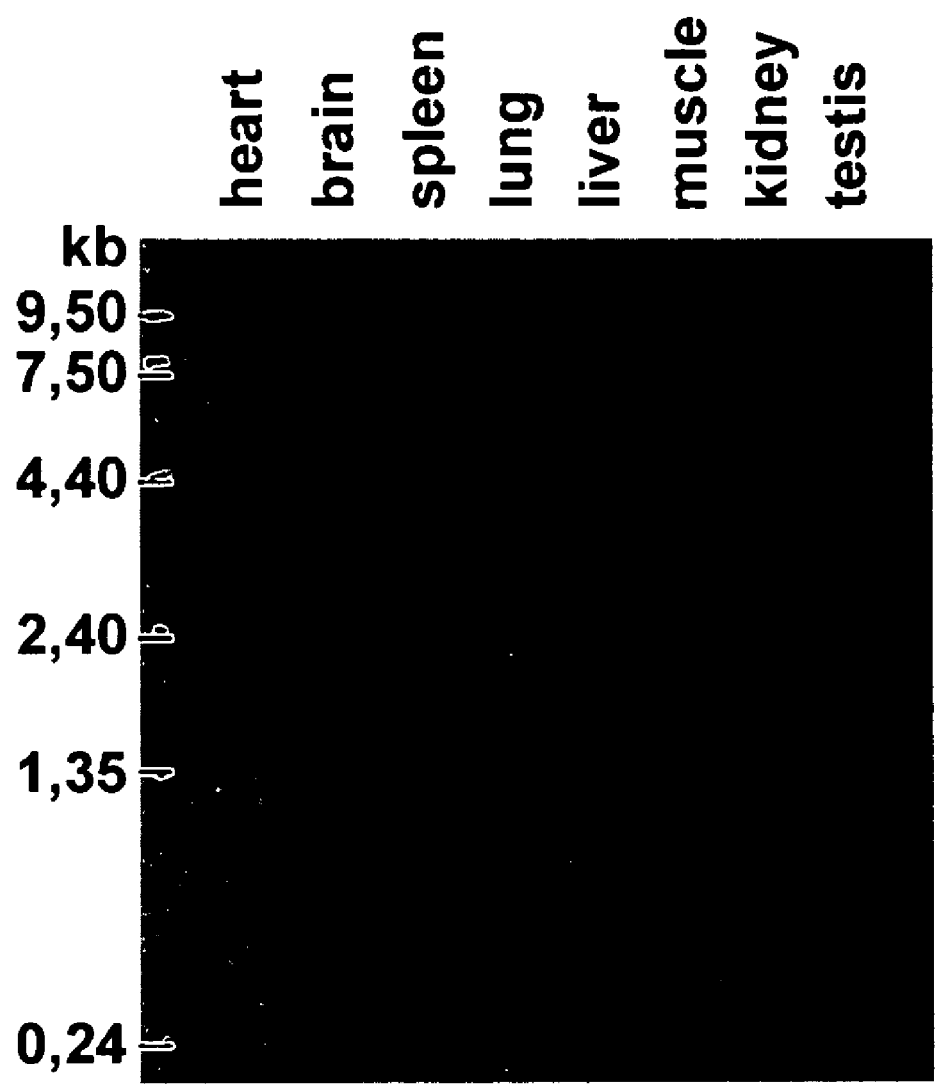

```
         1          10                   20                   30                   40                   50                   60
MQRAGSSGGR GECDISGAGR LGLEEAARLS CAVHTSPGGG RRPGQAAGMS AKERPKGKVI
         70          80                   90                  100                  110                  120
KDSVTLLPCF YFVELPILAS SVVSLYFLEL TDVFKPVHSG FSCYDRSLSM PYIEPTQEAI
        130         140                  150                  160                  170                  180
PFLMLLSLAF AGPAITIMVG EGILYCCLSK RRNGVGLEPN INAGGCNFNS FLRRAVRFVG
        190         200                  210                  220                  230                  240
VHVFGLCSTA LITDIIQLST GYQAPYFLTV CKPNYTSLNV SCKENSYIVE DICSGSDLTV
        250    ★    260                  270                  280                  290                  300
INSGRKSFPS QHATLAAFAA VYVSMYFNST LTDSSKLLKP LLVFTFIICG IICGLTRITQ
        310         320                  330                  340                  350                  360
YKNHPVDVYC GFLIGGGIAL YLGLYAVGNF LPSDESMFQH RDALRSLTDL NQDPNRLLSA
        370         380                  390                  400                  410                  420
KNGSSSDGIA HTEGILNRNH RDASSLTNLK RANADVEIIT PRSPMGKENM VTESNTLPRA
        430         440                  450                  460                  470                  480
NTPSVEDPVR RNASIHASMD SARSKQLLTQ WKNKNESRKL SLQVIEPEPG QSPPRSIEMR
        490         500                  510                  520                  530                  540
SSSEPSRVGV NGDHHGPGNQ YLKIQPGAVP GCNNSMPGGP RVSIQSRPGS SQLVHIPEET
        550         560                  570                  580                  590                  600
QENISTSPKS SSARAKWLKA AEKTVACNRS NSQPRIMQVI AMSKQQGVLQ SSPKNTEGST
        610         620                  630                  640                  650                  660
VSCTGSIRYK TLTDHEPSGI VRVEAHPENN RPIIQIPSTE GEGSGSWKWK APEKGSLRQT
        670         680                  690                  700                  710                  720
YELNDLNRDS ESCESLKDSF GSGDRKRSNI DSNEHHHGI TTIRVTPVEG SEIGSETLSI
        730         740                  750                  760
SSSRDSTLRR KGNIILIPER SNSPENTRNI FYKGTSPTRA YKD
```

B

Figure shows the nucleotide sequence with corresponding amino acid translation, with transmembrane regions TM1–TM6 highlighted.

Figure 2
A
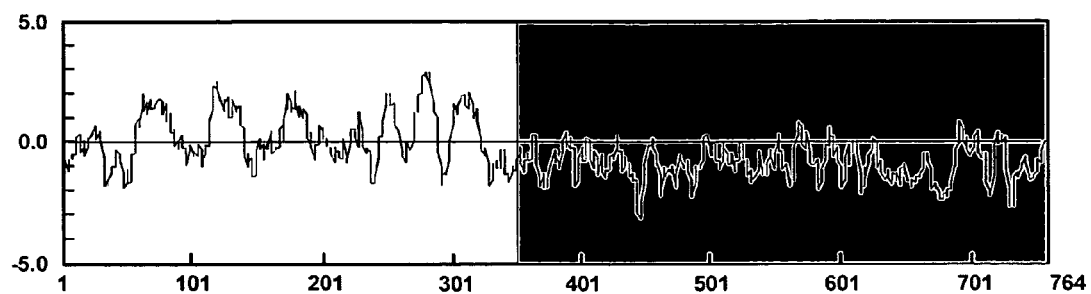
B
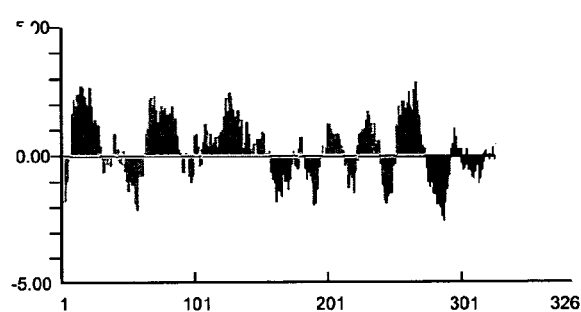
C
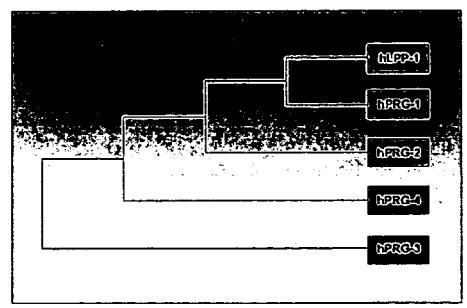

Figure 6
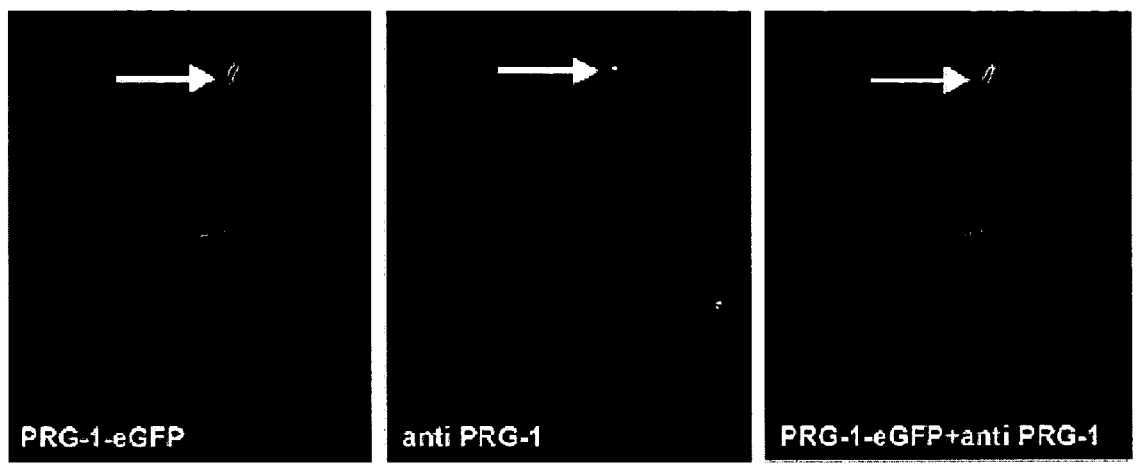
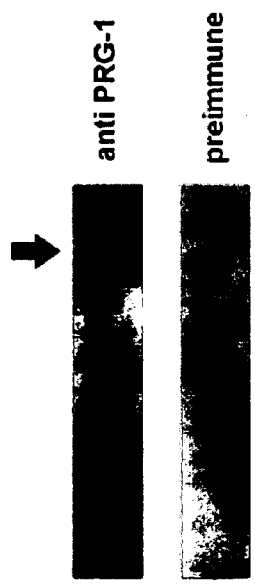

Figure 7
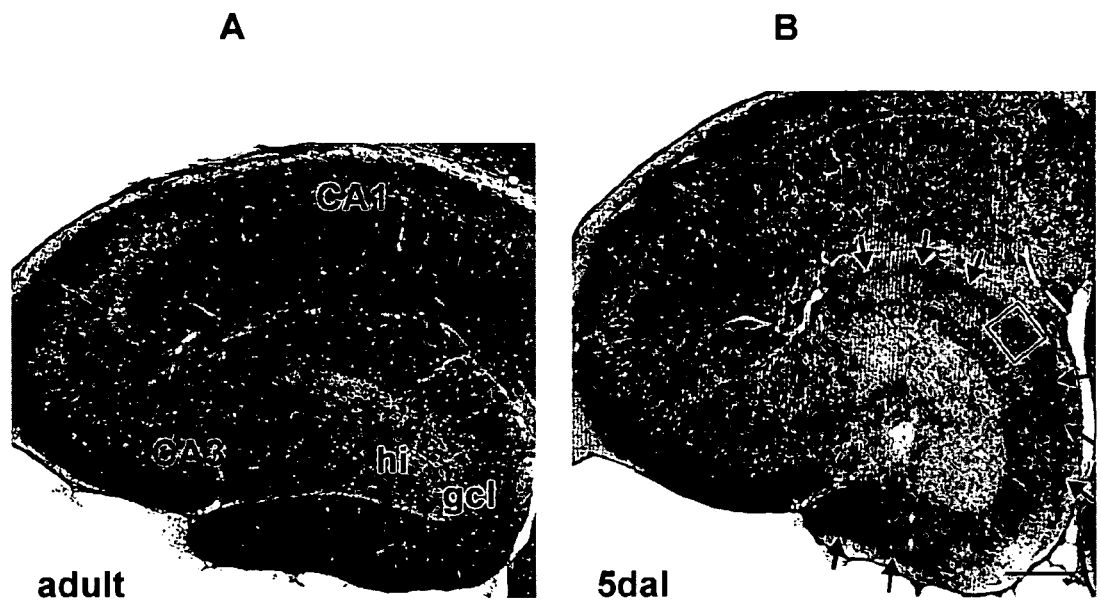
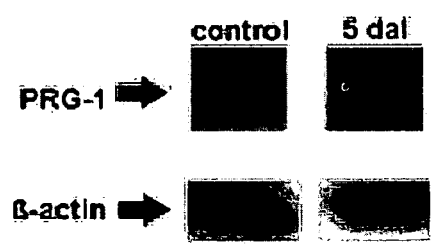
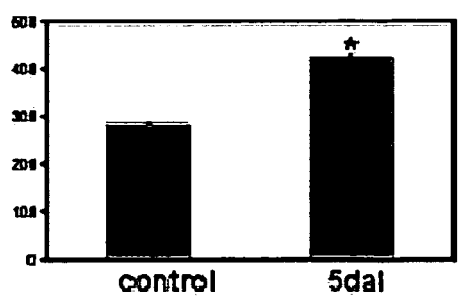

SEQUENCE LISTING

```
<160> NUMBER OF SEQ ID NOS: 38

<210> SEQ ID NO 1
<211> LENGTH: 763
<212> TYPE: PRT
<213> ORGANISM: Homo sapiens

<400> SEQUENCE: 1

Met Gln Arg Ala Gly Ser Ser Gly Gly Arg Gly Glu Cys Asp Ile Ser
1               5                   10                  15

Gly Ala Gly Arg Leu Gly Leu Glu Glu Ala Ala Arg Leu Ser Cys Ala
            20                  25                  30

Val His Thr Ser Pro Gly Gly Arg Arg Pro Gly Gln Ala Ala Gly
            35                  40                  45

Met Ser Ala Lys Glu Arg Pro Lys Gly Lys Val Ile Lys Asp Ser Val
    50                  55                  60

Thr Leu Leu Pro Cys Phe Tyr Phe Val Glu Leu Pro Ile Leu Ala Ser
65                  70                  75                  80

Ser Val Val Ser Leu Tyr Phe Leu Glu Leu Thr Asp Val Phe Lys Pro
                85                  90                  95

Val His Ser Gly Phe Ser Cys Tyr Asp Arg Ser Leu Ser Met Pro Tyr
            100                 105                 110

Ile Glu Pro Thr Gln Glu Ala Ile Pro Phe Leu Met Leu Leu Ser Leu
            115                 120                 125

Ala Phe Ala Gly Pro Ala Ile Thr Ile Met Val Gly Glu Gly Ile Leu
130                 135                 140

Tyr Cys Cys Leu Ser Lys Arg Arg Asn Gly Val Gly Leu Glu Pro Asn
145                 150                 155                 160

Ile Asn Ala Gly Gly Cys Asn Phe Asn Ser Phe Leu Arg Arg Ala Val
                165                 170                 175

Arg Phe Val Gly Val His Val Phe Gly Leu Cys Ser Thr Ala Leu Ile
            180                 185                 190

Thr Asp Ile Ile Gln Leu Ser Thr Gly Tyr Gln Ala Pro Tyr Phe Leu
        195                 200                 205

Thr Val Cys Lys Pro Asn Tyr Thr Ser Leu Asn Val Ser Cys Lys Glu
    210                 215                 220

Asn Ser Tyr Ile Val Glu Asp Ile Cys Ser Gly Ser Asp Leu Thr Val
225                 230                 235                 240

Ile Asn Ser Gly Arg Lys Ser Phe Pro Ser Gln His Ala Thr Leu Ala
                245                 250                 255

Ala Phe Ala Ala Val Tyr Val Ser Met Tyr Phe Asn Ser Thr Leu Thr
            260                 265                 270

Asp Ser Ser Lys Leu Leu Lys Pro Leu Leu Val Phe Thr Phe Ile Ile
```

-continued

```
                275                 280                 285
Cys Gly Ile Ile Cys Gly Leu Thr Arg Ile Thr Gln Tyr Lys Asn His
            290                 295                 300
Pro Val Asp Val Tyr Cys Gly Phe Leu Ile Gly Gly Ile Ala Leu
305                 310                 315                 320
Tyr Leu Gly Leu Tyr Ala Val Gly Asn Phe Leu Pro Ser Asp Glu Ser
                325                 330                 335
Met Phe Gln His Arg Asp Ala Leu Arg Ser Leu Thr Asp Leu Asn Gln
            340                 345                 350
Asp Pro Asn Arg Leu Leu Ser Ala Lys Asn Gly Ser Ser Ser Asp Gly
            355                 360                 365
Ile Ala His Thr Glu Gly Ile Leu Asn Arg Asn His Arg Asp Ala Ser
            370                 375                 380
Ser Leu Thr Asn Leu Lys Arg Ala Asn Ala Asp Val Glu Ile Ile Thr
385                 390                 395                 400
Pro Arg Ser Pro Met Gly Lys Glu Asn Met Val Thr Phe Ser Asn Thr
                405                 410                 415
Leu Pro Arg Ala Asn Thr Pro Ser Val Glu Asp Pro Val Arg Arg Asn
            420                 425                 430
Ala Ser Ile His Ala Ser Met Asp Ser Ala Arg Ser Lys Gln Leu Leu
            435                 440                 445
Thr Gln Trp Lys Asn Lys Asn Glu Ser Arg Lys Leu Ser Leu Gln Val
        450                 455                 460
Ile Glu Pro Glu Pro Gly Gln Ser Pro Arg Ser Ile Glu Met Arg
465                 470                 475                 480
Ser Ser Ser Glu Pro Ser Arg Val Gly Val Asn Gly Asp His His Gly
                485                 490                 495
Pro Gly Asn Gln Tyr Leu Lys Ile Gln Pro Gly Ala Val Pro Gly Cys
            500                 505                 510
Asn Asn Ser Met Pro Gly Gly Pro Arg Val Ser Ile Gln Ser Arg Pro
            515                 520                 525
Gly Ser Ser Gln Leu Val His Ile Pro Glu Glu Thr Gln Glu Asn Ile
            530                 535                 540
Ser Thr Ser Pro Lys Ser Ser Ala Arg Ala Lys Trp Leu Lys Ala
545                 550                 555                 560
Ala Glu Lys Thr Val Ala Cys Asn Arg Ser Asn Ser Gln Pro Arg Ile
                565                 570                 575
Met Gln Val Ile Ala Met Ser Lys Gln Gln Gly Val Leu Gln Ser Ser
            580                 585                 590
Pro Lys Asn Thr Glu Gly Ser Thr Val Ser Cys Thr Gly Ser Ile Arg
            595                 600                 605
Tyr Lys Thr Leu Thr Asp His Glu Pro Ser Gly Ile Val Arg Val Glu
        610                 615                 620
Ala His Pro Glu Asn Asn Arg Pro Ile Ile Gln Ile Pro Ser Thr Glu
625                 630                 635                 640
Gly Glu Gly Ser Gly Ser Trp Lys Trp Lys Ala Pro Glu Lys Gly Ser
                645                 650                 655
Leu Arg Gln Thr Tyr Glu Leu Asn Asp Leu Asn Arg Asp Ser Glu Ser
            660                 665                 670
Cys Glu Ser Leu Lys Asp Ser Phe Gly Ser Gly Asp Arg Lys Arg Ser
            675                 680                 685
Asn Ile Asp Ser Asn Glu His His His His Gly Ile Thr Thr Ile Arg
            690                 695                 700
```

```
Val Thr Pro Val Glu Gly Ser Glu Ile Gly Ser Glu Thr Leu Ser Ile
705                 710                 715                 720

Ser Ser Ser Arg Asp Ser Thr Leu Arg Arg Lys Gly Asn Ile Ile Leu
            725                 730                 735

Ile Pro Glu Arg Ser Asn Ser Pro Glu Asn Thr Arg Asn Ile Phe Tyr
            740                 745                 750

Lys Gly Thr Ser Pro Thr Arg Ala Tyr Lys Asp
            755                 760

<210> SEQ ID NO 2
<211> LENGTH: 746
<212> TYPE: PRT
<213> ORGANISM: Homo sapiens

<400> SEQUENCE: 2

Met Ile Ser Thr Lys Glu Lys Asn Lys Ile Pro Lys Asp Ser Met Thr
1               5                   10                  15

Leu Leu Pro Cys Phe Tyr Phe Val Glu Leu Pro Ile Val Ala Ser Ser
            20                  25                  30

Ile Val Ser Leu Tyr Phe Leu Glu Leu Thr Asp Leu Phe Lys Pro Ala
            35                  40                  45

Lys Val Gly Phe Gln Cys Tyr Asp Arg Thr Leu Ser Met Pro Tyr Val
50                  55                  60

Glu Thr Asn Glu Glu Leu Ile Pro Leu Leu Met Leu Leu Ser Leu Ala
65                  70                  75                  80

Phe Ala Ala Pro Ala Ala Ser Ile Met Val Ala Glu Gly Met Leu Tyr
                85                  90                  95

Cys Leu Gln Ser Arg Leu Trp Gly Arg Ala Gly Gly Pro Ala Gly Ala
            100                 105                 110

Glu Gly Ser Ile Asn Ala Gly Gly Cys Asn Phe Asn Ser Phe Leu Arg
        115                 120                 125

Arg Thr Val Arg Phe Val Gly Val His Val Phe Gly Leu Cys Ala Thr
    130                 135                 140

Ala Leu Val Thr Asp Val Ile Gln Leu Ala Thr Gly Tyr His Thr Pro
145                 150                 155                 160

Phe Phe Leu Thr Val Cys Lys Pro Asn Tyr Thr Leu Leu Gly Thr Ser
                165                 170                 175

Cys Glu Val Asn Pro Tyr Ile Thr Gln Asp Ile Cys Ser Gly His Asp
            180                 185                 190

Ile His Ala Ile Leu Ser Ala Arg Lys Thr Phe Pro Ser Gln His Ala
        195                 200                 205

Thr Leu Ser Ala Phe Ala Ala Val Tyr Val Ser Val Ser Pro Ala Pro
    210                 215                 220

His Cys Pro Ser Gln Ala Leu Leu Thr Arg Gly Glu Pro Ser Leu
225                 230                 235                 240

Thr Pro Thr Pro Met Pro Gln Met Tyr Phe Asn Ser Val Ile Ser Asp
                245                 250                 255

Thr Thr Lys Leu Leu Lys Pro Ile Leu Val Phe Ala Phe Ala Ile Ala
            260                 265                 270

Ala Gly Val Cys Gly Leu Thr Gln Ile Thr Gln Tyr Arg Ser His Pro
        275                 280                 285

Val Asp Val Tyr Ala Gly Phe Leu Ile Gly Ala Gly Ile Ala Ala Tyr
    290                 295                 300

Leu Ala Cys His Ala Val Gly Asn Phe Gln Ala Pro Pro Ala Glu Lys
```

```
            305                 310                 315                 320
Pro Ala Ala Pro Ala Pro Ala Lys Asp Ala Leu Arg Ala Leu Thr Gln
                325                 330                 335
Arg Gly His Asp Ser Val Tyr Gln Gln Asn Lys Ser Val Ser Thr Asp
                340                 345                 350
Glu Leu Gly Pro Pro Gly Arg Leu Glu Gly Ala Pro Arg Pro Val Ala
                355                 360                 365
Arg Glu Lys Thr Ser Leu Gly Ser Leu Lys Arg Ala Ser Val Asp Val
                370                 375                 380
Asp Leu Leu Ala Pro Arg Ser Pro Met Ala Lys Glu Asn Met Val Thr
385                 390                 395                 400
Phe Ser His Thr Leu Pro Arg Ala Ser Ala Pro Ser Leu Asp Asp Pro
                405                 410                 415
Ala Arg Arg His Met Thr Ile His Val Pro Leu Asp Ala Ser Arg Ser
                420                 425                 430
Lys Gln Leu Ile Ser Glu Trp Lys Gln Lys Ser Leu Glu Gly Arg Gly
                435                 440                 445
Leu Gly Leu Pro Asp Asp Ala Ser Pro Gly His Leu Arg Ala Pro Ala
                450                 455                 460
Glu Pro Met Ala Glu Glu Glu Glu Glu Asp Glu Glu Glu
465                 470                 475                 480
Glu Glu Glu Glu Glu Glu Glu Asp Glu Gly Pro Ala Pro Pro Ser Leu
                485                 490                 495
Tyr Pro Thr Val Gln Ala Arg Pro Gly Leu Gly Pro Arg Val Ile Leu
                500                 505                 510
Pro Pro Arg Ala Gly Pro Pro Leu Val His Ile Pro Glu Glu Gly
                515                 520                 525
Ala Gln Thr Gly Ala Gly Leu Ser Pro Lys Ser Gly Ala Gly Val Arg
                530                 535                 540
Ala Lys Trp Leu Met Met Ala Glu Lys Ser Gly Ala Ala Val Ala Asn
545                 550                 555                 560
Pro Pro Arg Leu Leu Gln Val Ile Ala Met Ser Lys Ala Pro Gly Ala
                565                 570                 575
Pro Gly Pro Lys Ala Ala Glu Thr Ala Ser Ser Ser Ala Ser Ser
                580                 585                 590
Asp Ser Ser Gln Tyr Arg Ser Pro Ser Asp Arg Asp Ser Ala Ser Ile
                595                 600                 605
Val Thr Ile Asp Ala His Ala Pro His His Pro Val His Leu Ser
                610                 615                 620
Ala Gly Gly Ala Pro Trp Glu Trp Lys Ala Ala Gly Gly Ala Lys
625                 630                 635                 640
Ala Glu Ala Asp Gly Gly Tyr Glu Leu Gly Asp Leu Ala Arg Gly Phe
                645                 650                 655
Arg Gly Gly Ala Lys Pro Pro Gly Val Ser Pro Gly Ser Ser Val Ser
                660                 665                 670
Asp Val Asp Gln Glu Glu Pro Arg Phe Gly Ala Val Ala Thr Val Asn
                675                 680                 685
Leu Ala Thr Gly Glu Gly Leu Pro Pro Leu Gly Ala Ala Asp Gly Ala
                690                 695                 700
Leu Gly Pro Gly Ser Arg Glu Ser Thr Leu Arg Arg His Ala Gly Gly
705                 710                 715                 720
Leu Gly Leu Ala Glu Arg Glu Ala Glu Ala Glu Ala Glu Gly Tyr Phe
                725                 730                 735
```

Arg Lys Met Gln Ala Arg Arg Phe Pro Asp
            740                 745

<210> SEQ ID NO 3
<211> LENGTH: 325
<212> TYPE: PRT
<213> ORGANISM: Homo sapiens

<400> SEQUENCE: 3

Met Ala Val Gly Asn Asn Thr Gln Arg Ser Tyr Ser Ile Ile Pro Cys
1               5                   10                  15

Phe Ile Phe Val Glu Leu Val Ile Met Ala Gly Thr Val Leu Leu Ala
                20                  25                  30

Tyr Tyr Phe Glu Cys Thr Asp Thr Phe Gln Val His Ile Gln Gly Phe
            35                  40                  45

Phe Cys Gln Asp Gly Asp Leu Met Lys Pro Tyr Pro Gly Thr Glu Glu
        50                  55                  60

Glu Ser Phe Ile Thr Pro Leu Val Leu Tyr Cys Val Leu Ala Ala Thr
65                  70                  75                  80

Pro Thr Ala Ile Ile Phe Ile Gly Glu Ile Ser Met Tyr Phe Ile Lys
                85                  90                  95

Ser Thr Arg Glu Ser Leu Ile Ala Gln Glu Lys Thr Ile Leu Thr Gly
            100                 105                 110

Glu Cys Cys Tyr Leu Asn Pro Leu Leu Arg Arg Ile Ile Arg Phe Thr
        115                 120                 125

Gly Val Phe Ala Phe Gly Leu Phe Ala Thr Asp Ile Phe Val Asn Ala
130                 135                 140

Gly Gln Val Val Thr Gly His Leu Thr Pro Tyr Phe Leu Thr Val Cys
145                 150                 155                 160

Lys Pro Asn Tyr Thr Ser Ala Asp Cys Gln Ala His His Gln Phe Ile
                165                 170                 175

Asn Asn Gly Asn Ile Cys Thr Gly Asp Leu Glu Val Ile Glu Lys Ala
            180                 185                 190

Arg Arg Ser Phe Pro Ser Lys His Ala Ala Leu Ser Ile Tyr Ser Ala
        195                 200                 205

Leu Tyr Ala Thr Met Tyr Ile Thr Ser Thr Ile Lys Thr Lys Ser Ser
210                 215                 220

Arg Leu Ala Lys Pro Val Leu Cys Leu Gly Thr Leu Cys Thr Ala Phe
225                 230                 235                 240

Leu Thr Gly Leu Asn Arg Val Ser Glu Tyr Arg Asn His Cys Ser Asp
                245                 250                 255

Val Ile Ala Gly Phe Ile Leu Gly Thr Ala Val Ala Leu Phe Leu Gly
            260                 265                 270

Met Cys Val Val His Asn Phe Lys Gly Thr Gln Gly Ser Pro Ser Lys
        275                 280                 285

Pro Lys Pro Glu Asp Pro Arg Gly Val Pro Leu Met Ala Phe Pro Arg
290                 295                 300

Ile Glu Ser Pro Leu Glu Thr Leu Ser Ala Gln Asn His Ser Ala Ser
305                 310                 315                 320

Met Thr Glu Val Thr
            325

<210> SEQ ID NO 4
<211> LENGTH: 343
<212> TYPE: PRT

<213> ORGANISM: Homo sapiens

<400> SEQUENCE: 4

```
Met Ala Gly Gly Arg Pro His Leu Lys Arg Ser Phe Ser Ile Ile Pro
1               5                   10                  15
Cys Phe Val Phe Val Glu Ser Val Leu Leu Gly Ile Val Ile Leu Leu
            20                  25                  30
Ala Tyr Arg Leu Glu Phe Thr Asp Thr Phe Pro Val His Thr Gln Gly
        35                  40                  45
Phe Phe Cys Tyr Asp Ser Thr Tyr Ala Lys Pro Tyr Pro Gly Pro Glu
    50                  55                  60
Ala Ala Ser Arg Val Pro Pro Ala Leu Val Tyr Ala Leu Val Thr Ala
65                  70                  75                  80
Gly Pro Thr Leu Thr Ile Leu Leu Gly Glu Leu Ala Arg Ala Phe Phe
                85                  90                  95
Pro Ala Pro Pro Ser Ala Val Pro Val Ile Gly Glu Ser Thr Ile Val
            100                 105                 110
Ser Gly Ala Cys Cys Arg Phe Ser Pro Pro Val Arg Arg Leu Val Arg
        115                 120                 125
Phe Leu Gly Val Tyr Ser Phe Gly Leu Phe Thr Thr Thr Ile Phe Ala
    130                 135                 140
Asn Ala Gly Gln Val Val Thr Gly Asn Pro Thr Pro His Phe Leu Ser
145                 150                 155                 160
Val Cys Arg Pro Asn Tyr Thr Ala Leu Gly Cys Leu Pro Pro Ser Pro
                165                 170                 175
Asp Arg Pro Gly Pro Asp Arg Phe Val Thr Asp Gln Gly Ala Cys Ala
            180                 185                 190
Gly Ser Pro Ser Leu Val Ala Ala Arg Arg Ala Phe Pro Cys Lys
        195                 200                 205
Asp Ala Ala Leu Cys Ala Tyr Ala Val Thr Tyr Thr Ala Met Tyr Val
    210                 215                 220
Thr Leu Val Phe Arg Val Lys Gly Ser Arg Leu Val Lys Pro Ser Leu
225                 230                 235                 240
Cys Leu Ala Leu Leu Cys Pro Ala Phe Leu Val Gly Val Val Arg Val
                245                 250                 255
Ala Glu Tyr Arg Asn His Trp Ser Asp Val Leu Ala Gly Phe Leu Thr
            260                 265                 270
Gly Ala Ala Ile Ala Thr Phe Leu Val Thr Cys Val Val His Asn Phe
        275                 280                 285
Gln Ser Arg Pro Pro Ser Gly Arg Arg Leu Ser Pro Trp Glu Asp Leu
    290                 295                 300
Gly Gln Ala Pro Thr Met Asp Ser Pro Leu Glu Lys Asn Pro Arg Ser
305                 310                 315                 320
Ala Gly Arg Ile Arg His Arg His Gly Ser Pro His Pro Ser Arg Arg
                325                 330                 335
Thr Ala Pro Ala Val Ala Thr
            340
```

<210> SEQ ID NO 5
<211> LENGTH: 766
<212> TYPE: PRT
<213> ORGANISM: Mus musculus

<400> SEQUENCE: 5

Met Gln Arg Ala Gly Ser Ser Gly Ala Arg Gly Glu Cys Asp Ile Ser

```
                1               5                       10                      15
        Gly Ala Gly Arg Leu Arg Leu Glu Gln Ala Ala Arg Leu Gly Gly Arg
                        20                      25                      30

Thr Val His Thr Ser Pro Gly Gly Leu Gly Ala Arg Gln Ala Ala
                        35                      40                  45

Gly Met Ser Ala Lys Glu Arg Pro Lys Gly Lys Val Ile Lys Asp Ser
                50                      55                      60

Val Thr Leu Leu Pro Cys Phe Tyr Phe Val Glu Leu Pro Ile Leu Ala
        65                      70                      75                      80

Ser Ser Val Val Ser Leu Tyr Phe Leu Glu Leu Thr Asp Val Phe Lys
                                85                      90                      95

Pro Val His Ser Gly Phe Ser Cys Tyr Asp Arg Ser Leu Ser Met Pro
                        100                     105                     110

Tyr Ile Glu Pro Thr Gln Glu Ala Ile Pro Phe Leu Met Leu Leu Ser
                        115                     120                     125

Leu Ala Phe Ala Gly Pro Ala Ile Thr Ile Met Val Gly Glu Gly Ile
                130                     135                     140

Leu Tyr Cys Cys Leu Ser Lys Arg Arg Asn Gly Ala Gly Leu Glu Pro
        145                     150                     155                     160

Asn Ile Asn Ala Gly Gly Cys Asn Phe Asn Ser Phe Leu Arg Arg Ala
                        165                     170                     175

Val Arg Phe Val Gly Val His Val Phe Gly Leu Cys Ser Thr Ala Leu
                        180                     185                     190

Ile Thr Asp Ile Ile Gln Leu Ser Thr Gly Tyr Gln Ala Pro Tyr Phe
                        195                     200                     205

Leu Thr Val Cys Lys Pro Asn Tyr Thr Ser Leu Asn Val Ser Cys Lys
                210                     215                     220

Glu Asn Ser Tyr Ile Val Glu Asp Ile Cys Ser Gly Ser Asp Leu Thr
        225                     230                     235                     240

Val Ile Asn Ser Gly Arg Lys Ser Phe Pro Ser Gln His Ala Thr Leu
                        245                     250                     255

Ala Ala Phe Ala Ala Val Tyr Val Ser Met Tyr Phe Asn Ser Thr Leu
                        260                     265                     270

Thr Asp Ser Ser Lys Leu Leu Lys Pro Leu Leu Val Phe Thr Phe Ile
                        275                     280                     285

Ile Cys Gly Ile Ile Cys Gly Leu Thr Arg Ile Thr Gln Tyr Lys Asn
                290                     295                     300

His Pro Val Asp Val Tyr Cys Gly Phe Leu Ile Gly Gly Gly Ile Ala
        305                     310                     315                     320

Leu Tyr Leu Gly Leu Tyr Ala Val Gly Asn Phe Leu Pro Ser Glu Asp
                        325                     330                     335

Ser Met Leu Gln His Arg Asp Ala Leu Arg Ser Leu Thr Asp Leu Asn
                        340                     345                     350

Gln Asp Pro Ser Arg Val Leu Ser Ala Lys Asn Gly Ser Ser Gly Asp
                        355                     360                     365

Gly Ile Ala His Thr Glu Gly Ile Leu Asn Arg Asn His Arg Asp Ala
                370                     375                     380

Ser Ser Leu Thr Asn Leu Lys Arg Ala Asn Ala Asp Val Glu Ile Ile
        385                     390                     395                     400

Thr Pro Arg Ser Pro Met Gly Lys Glu Ser Met Val Thr Phe Ser Asn
                        405                     410                     415

Thr Leu Pro Arg Ala Asn Thr Pro Ser Val Glu Asp Pro Val Arg Arg
                        420                     425                     430
```

```
Asn Ala Ser Ile His Ala Ser Met Asp Ser Ala Arg Ser Lys Gln Leu
            435                 440                 445

Leu Thr Gln Trp Lys Ser Lys Asn Glu Ser Arg Lys Met Ser Leu Gln
    450                 455                 460

Val Met Asp Thr Glu Pro Glu Gly Gln Ser Pro Arg Ser Ile Glu
465                 470                 475                 480

Met Arg Ser Ser Ser Glu Pro Ser Arg Val Gly Val Asn Gly Asp His
                485                 490                 495

His Val Pro Gly Asn Gln Tyr Leu Lys Ile Gln Pro Gly Thr Val Pro
            500                 505                 510

Gly Cys Asn Asn Ser Met Pro Gly Gly Pro Arg Val Ser Ile Gln Ser
            515                 520                 525

Arg Pro Gly Ser Ser Gln Leu Val His Ile Pro Glu Glu Thr Gln Glu
        530                 535                 540

Asn Ile Ser Thr Ser Pro Lys Ser Ser Ser Ala Arg Ala Lys Trp Leu
545                 550                 555                 560

Lys Ala Ala Glu Lys Thr Val Asp Cys Asn Arg Ser Asn Asn Gln Pro
                565                 570                 575

Arg Ile Met Gln Val Ile Ala Met Ser Lys Gln Gln Gly Val Leu Gln
            580                 585                 590

Ser Ser Pro Lys Asn Ala Glu Gly Ser Thr Val Thr Cys Thr Gly Ser
        595                 600                 605

Ile Arg Tyr Lys Thr Leu Thr Asp His Glu Pro Ser Gly Ile Val Arg
        610                 615                 620

Val Glu Ala His Pro Glu Asn Asn Arg Pro Ile Ile Gln Ile Pro Ser
625                 630                 635                 640

Ser Thr Glu Gly Glu Gly Ser Gly Ser Trp Lys Trp Lys Val Pro Glu
                645                 650                 655

Lys Ser Ser Leu Arg Gln Thr Tyr Glu Leu Asn Asp Leu Asn Arg Asp
            660                 665                 670

Ser Glu Ser Cys Glu Ser Leu Lys Asp Ser Phe Gly Ser Gly Asp Arg
        675                 680                 685

Lys Arg Ser Asn Ile Asp Ser Asn Glu His His His Gly Ile Thr
        690                 695                 700

Thr Ile Arg Val Thr Pro Val Glu Gly Ser Glu Ile Gly Ser Glu Thr
705                 710                 715                 720

Leu Ser Val Ser Ser Arg Asp Ser Thr Leu Arg Arg Lys Gly Asn
                725                 730                 735

Ile Ile Leu Ile Pro Glu Arg Ser Asn Ser Pro Glu Asn Thr Arg Asn
            740                 745                 750

Ile Phe Tyr Lys Gly Thr Ser Pro Thr Arg Ala Tyr Lys Asp
            755                 760                 765

<210> SEQ ID NO 6
<211> LENGTH: 716
<212> TYPE: PRT
<213> ORGANISM: Mus musculus

<400> SEQUENCE: 6

Met Leu Ala Met Lys Glu Lys Asn Lys Thr Pro Lys Asp Ser Met Thr
1               5                   10                  15

Leu Leu Pro Cys Phe Tyr Phe Val Glu Leu Pro Ile Val Ala Ser Ser
                20                  25                  30

Ile Val Ser Leu Tyr Phe Leu Glu Leu Thr Asp Leu Phe Lys Pro Ala
```

-continued

```
               35                  40                  45
Lys Val Gly Phe Gln Cys Tyr Asp Arg Ala Leu Ser Met Pro Tyr Val
             50                  55                  60

Glu Thr Asn Glu Glu Leu Ile Pro Leu Leu Met Leu Leu Ser Leu Ala
 65                  70                  75                  80

Phe Ala Ala Pro Ala Ala Ser Ile Met Val Gly Glu Gly Met Val Tyr
                 85                  90                  95

Cys Leu Gln Ser Arg Leu Trp Gly Arg Gly Pro Gly Gly Val Glu Gly
                100                 105                 110

Ser Ile Asn Ala Gly Gly Cys Asn Phe Asn Ser Phe Leu Arg Arg Thr
            115                 120                 125

Val Arg Phe Val Gly Val His Val Phe Gly Leu Cys Ala Thr Ala Leu
        130                 135                 140

Val Thr Asp Val Ile Gln Leu Ala Thr Gly Tyr His Thr Pro Phe Phe
145                 150                 155                 160

Leu Thr Val Cys Lys Pro Asn Tyr Thr Leu Leu Gly Thr Ser Cys Glu
                165                 170                 175

Ser Asn Pro Tyr Ile Thr Gln Asp Ile Cys Ser Gly His Asp Thr His
            180                 185                 190

Ala Ile Leu Ser Ala Arg Lys Thr Phe Pro Ser Gln His Ala Thr Leu
        195                 200                 205

Ser Ala Phe Ala Ala Val Tyr Val Ser Met Tyr Phe Asn Ala Val Ile
210                 215                 220

Ser Asp Thr Thr Lys Leu Leu Lys Pro Ile Leu Val Phe Ala Phe Ala
225                 230                 235                 240

Ile Ala Ala Gly Val Cys Gly Leu Thr Gln Ile Thr Gln Tyr Arg Ser
                245                 250                 255

His Pro Val Asp Val Tyr Ala Gly Phe Leu Ile Gly Ala Gly Ile Ala
            260                 265                 270

Ala Tyr Leu Ala Cys His Ala Val Gly Asn Phe Gln Ala Pro Pro Ala
        275                 280                 285

Glu Lys Val Pro Thr Pro Ala Pro Ala Lys Asp Ala Leu Arg Ala Leu
    290                 295                 300

Thr Gln Arg Gly His Glu Ser Met Tyr Gln Gln Asn Lys Ser Val Ser
305                 310                 315                 320

Thr Asp Glu Leu Gly Pro Pro Gly Arg Leu Glu Gly Val Pro Arg Pro
                325                 330                 335

Val Ala Arg Glu Lys Thr Ser Leu Gly Ser Leu Lys Arg Ala Ser Val
            340                 345                 350

Asp Val Asp Leu Leu Ala Pro Arg Ser Pro Met Gly Lys Glu Gly Met
        355                 360                 365

Val Thr Phe Ser Asn Thr Leu Pro Arg Val Ser Thr Pro Ser Leu Asp
    370                 375                 380

Asp Pro Ala Arg Arg His Met Thr Ile His Val Pro Leu Asp Ala Ser
385                 390                 395                 400

Arg Ser Arg Gln Leu Ile Gly Glu Trp Lys Gln Lys Ser Leu Glu Gly
                405                 410                 415

Arg Gly Leu Gly Leu Pro Asp Glu Ala Ser Pro Val His Leu Arg Ala
            420                 425                 430

Pro Ala Glu Gln Val Ala Glu Glu Glu Glu Glu Glu Glu Glu Glu Glu
        435                 440                 445

Glu Glu Glu Glu Glu Glu Glu Glu Glu Gly Pro Val Pro Pro Ser
    450                 455                 460
```

```
Leu Tyr Pro Thr Val Gln Ala Arg Pro Gly Leu Gly Pro Arg Val Ile
465                 470                 475                 480

Leu Pro Pro Arg Pro Gly Pro Gln Pro Leu Val His Ile Pro Glu Glu
                485                 490                 495

Gly Val Gln Ala Gly Ala Gly Leu Ser Pro Lys Ser Ser Ser Ser Ser
            500                 505                 510

Val Arg Ala Lys Trp Leu Ser Val Ala Glu Lys Gly Gly Pro Val
        515                 520                 525

Ala Val Ala Pro Ser Gln Pro Arg Val Ala Asn Pro Pro Arg Leu Leu
    530                 535                 540

Gln Val Ile Ala Met Ser Lys Ala Ala Gly Gly Pro Lys Ala Glu Thr
545                 550                 555                 560

Ala Ser Ser Ser Ser Ala Ser Ser Asp Ser Gln Tyr Arg Ser Pro
                565                 570                 575

Ser Asp Arg Asp Ser Ala Ser Ile Val Thr Ile Asp Ala His Ala Pro
            580                 585                 590

His His Pro Val Val His Leu Ser Ala Gly Ser Thr Pro Trp Glu Trp
                595                 600                 605

Lys Ala Lys Val Val Glu Gly Glu Gly Ser Tyr Glu Leu Gly Asp Leu
            610                 615                 620

Ala Arg Gly Phe Arg Ser Ser Cys Lys Gln Pro Gly Met Gly Pro Gly
625                 630                 635                 640

Ser Pro Val Ser Asp Val Asp Gln Glu Glu Pro Arg Phe Gly Ala Val
                645                 650                 655

Ala Thr Val Asn Leu Ala Thr Gly Glu Gly Leu Pro Pro Pro Gly Ala
            660                 665                 670

Ser Glu Gly Ala Leu Gly Ala Gly Ser Arg Glu Ser Thr Leu Arg Arg
                675                 680                 685

Gln Val Gly Gly Leu Ala Glu Arg Glu Val Glu Ala Glu Ala Glu Ser
            690                 695                 700

Tyr Tyr Arg Arg Met Gln Ala Arg Arg Tyr Gln Asp
705                 710                 715

<210> SEQ ID NO 7
<211> LENGTH: 325
<212> TYPE: PRT
<213> ORGANISM: Mus musculus

<400> SEQUENCE: 7

Met Ala Val Glu Asn Asn Thr Gln Arg Ser Tyr Ser Ile Ile Pro Cys
1               5                   10                  15

Phe Ile Phe Val Glu Leu Val Ile Met Ala Gly Thr Val Leu Leu Ala
                20                  25                  30

Tyr Tyr Phe Glu Cys Thr Asp Thr Phe Gln Val His Ile Gln Gly Phe
            35                  40                  45

Phe Cys Gln Asp Gly Asp Leu Met Lys Pro Tyr Pro Gly Thr Glu Glu
    50                  55                  60

Glu Ser Phe Ile Ser Pro Leu Val Leu Tyr Cys Val Leu Ala Ala Thr
65                  70                  75                  80

Pro Thr Ala Ile Ile Phe Ile Gly Glu Ile Ser Met Tyr Phe Ile Lys
                85                  90                  95

Ser Thr Arg Glu Ser Leu Ile Ala Glu Glu Lys Met Ile Leu Thr Gly
            100                 105                 110

Asp Cys Cys Tyr Leu Ser Pro Leu Leu Arg Arg Ile Ile Arg Phe Ile
```

```
                115                 120                 125
Gly Val Phe Ala Phe Gly Leu Phe Ala Thr Asp Ile Phe Val Asn Ala
    130                 135                 140

Gly Gln Val Val Thr Gly His Leu Thr Pro Tyr Phe Leu Thr Val Cys
145                 150                 155                 160

Gln Pro Asn Tyr Thr Ser Thr Asp Cys Arg Ala His Gln Gln Phe Ile
                165                 170                 175

Asn Asn Gly Asn Ile Cys Thr Gly Asp Leu Glu Val Ile Glu Lys Ala
                180                 185                 190

Arg Arg Ser Phe Pro Ser Lys His Ala Ala Leu Ser Ile Tyr Ser Ala
                195                 200                 205

Leu Tyr Ala Thr Met Tyr Ile Thr Ser Thr Ile Lys Thr Lys Ser Ser
    210                 215                 220

Arg Leu Ala Lys Pro Val Leu Cys Leu Gly Thr Leu Cys Thr Ala Phe
225                 230                 235                 240

Leu Thr Gly Leu Asn Arg Val Ser Glu Tyr Arg Asn His Cys Ser Asp
                245                 250                 255

Val Ile Ala Gly Phe Ile Leu Gly Thr Ala Val Ala Leu Phe Leu Gly
                260                 265                 270

Met Cys Val Val His Asn Phe Arg Gly Thr Gln Gly Ser Pro Ser Lys
    275                 280                 285

Pro Lys Pro Glu Asp Pro Arg Gly Val Pro Leu Met Ala Phe Pro Arg
290                 295                 300

Ile Glu Ser Pro Leu Glu Thr Leu Ser Ala Gln Asn His Ser Ala Ser
305                 310                 315                 320

Met Thr Glu Val Thr
                325

<210> SEQ ID NO 8
<211> LENGTH: 343
<212> TYPE: PRT
<213> ORGANISM: Mus musculus

<400> SEQUENCE: 8

Met Ala Gly Gly Arg Pro His Leu Lys Arg Ser Phe Ser Ile Ile Pro
1               5                   10                  15

Cys Phe Val Phe Val Glu Ser Val Leu Leu Gly Ile Val Val Leu Leu
                20                  25                  30

Ala Tyr Arg Leu Glu Phe Thr Asp Thr Phe Pro Val His Thr Gln Gly
            35                  40                  45

Phe Phe Cys Tyr Asp Ser Ala Tyr Ala Lys Pro Tyr Pro Gly Pro Glu
    50                  55                  60

Ala Ala Ser Arg Ala Pro Pro Ala Leu Ile Tyr Ala Leu Val Thr Ala
65                  70                  75                  80

Gly Pro Thr Leu Thr Ile Leu Leu Gly Glu Leu Ala Arg Ala Phe Phe
                85                  90                  95

Pro Ala Pro Pro Ser Ser Ser Pro Val Ser Gly Glu Ser Thr Ile Val
            100                 105                 110

Ser Gly Ala Cys Cys Arg Phe Ser Pro Pro Leu Arg Arg Leu Val Arg
        115                 120                 125

Phe Leu Gly Val Tyr Ser Phe Gly Leu Phe Thr Thr Thr Ile Phe Ala
    130                 135                 140

Asn Ala Gly Gln Val Val Thr Gly Asn Pro Thr Pro His Phe Leu Ser
145                 150                 155                 160
```

```
Val Cys Arg Pro Asn Tyr Thr Ala Leu Gly Cys Pro Pro Ser Pro
                165                 170                 175

Asp Arg Pro Gly Pro Asp Arg Phe Val Thr Asp Gln Ser Ala Cys Ala
            180                 185                 190

Gly Ser Pro Ser Leu Val Ala Ala Arg Arg Ala Phe Pro Cys Lys
        195                 200                 205

Asp Ala Ala Leu Cys Ala Tyr Ala Val Thr Tyr Thr Ala Met Tyr Val
    210                 215                 220

Thr Leu Val Phe Arg Val Lys Gly Ser Arg Leu Val Lys Pro Ser Leu
225                 230                 235                 240

Cys Leu Ala Leu Leu Cys Pro Ala Phe Leu Val Gly Val Val Arg Val
                245                 250                 255

Ala Glu Tyr Arg Asn His Trp Ser Asp Val Leu Ala Gly Phe Leu Thr
            260                 265                 270

Gly Ala Ala Ile Ala Thr Phe Leu Val Thr Cys Val Val His Asn Phe
        275                 280                 285

Gln Ser Arg Pro His Ser Gly Arg Arg Leu Ser Pro Trp Glu Asp Leu
    290                 295                 300

Ser Gln Ala Pro Thr Met Asp Ser Pro Leu Glu Lys Asn Pro Arg Pro
305                 310                 315                 320

Ala Gly Arg Ile Arg His Arg His Gly Ser Pro His Pro Ser Arg Arg
                325                 330                 335

Thr Val Pro Ala Val Ala Thr
            340

<210> SEQ ID NO 9
<211> LENGTH: 766
<212> TYPE: PRT
<213> ORGANISM: Rattus norvegicus

<400> SEQUENCE: 9

Met Gln Arg Ala Gly Ser Ser Gly Ala Arg Gly Glu Cys Asp Ile Ser
1               5                   10                  15

Gly Thr Gly Arg Leu Arg Leu Glu Gln Ala Ala Arg Leu Gly Gly Arg
            20                  25                  30

Ala Val His Thr Ser Pro Thr Gly Gly Leu Gly Ala Arg Gln Val Ala
        35                  40                  45

Gly Met Ser Ala Lys Glu Arg Pro Lys Gly Lys Val Ile Lys Asp Ser
    50                  55                  60

Val Thr Leu Leu Pro Cys Phe Tyr Phe Val Glu Leu Pro Ile Leu Ala
65                  70                  75                  80

Ser Ser Val Val Ser Leu Tyr Phe Leu Glu Leu Thr Asp Val Phe Lys
                85                  90                  95

Pro Val His Ser Gly Phe Ser Cys Tyr Asp Arg Ser Leu Ser Met Pro
            100                 105                 110

Tyr Ile Glu Pro Thr Gln Glu Ala Ile Pro Phe Leu Met Leu Leu Ser
        115                 120                 125

Leu Ala Phe Ala Gly Pro Ala Ile Thr Ile Met Val Gly Glu Gly Ile
    130                 135                 140

Leu Tyr Cys Cys Leu Ser Lys Arg Arg Asn Gly Ala Gly Leu Glu Pro
145                 150                 155                 160

Asn Ile Asn Ala Gly Gly Cys Asn Phe Asn Ser Phe Leu Arg Arg Ala
                165                 170                 175

Val Arg Phe Val Gly Val His Val Val Gly Leu Cys Ser Thr Ala Leu
            180                 185                 190
```

-continued

```
Ile Thr Asp Ile Ile Gln Leu Ala Thr Gly Tyr Gln Ala Pro Tyr Phe
            195                 200                 205

Leu Thr Val Cys Lys Pro Met Tyr Thr Ser Leu Glu Gly Ser Cys Lys
    210                 215                 220

Glu Asn Ser Tyr Ile Val Glu Glu Ile Cys Ser Gly Ser Asp Leu Thr
225                 230                 235                 240

Val Ile Asn Asn Gly Lys Lys Ser Phe Pro Ser Gln His Ala Thr Leu
                245                 250                 255

Ala Ala Phe Ala Ala Val Tyr Val Ser Met Tyr Phe Asn Ser Thr Leu
            260                 265                 270

Thr Asp Ser Ser Lys Leu Leu Lys Pro Leu Leu Val Phe Thr Phe Ile
    275                 280                 285

Ile Cys Gly Ile Ile Cys Gly Leu Thr Arg Ile Thr Gln Tyr Lys Asn
290                 295                 300

His Pro Val Asp Val Tyr Cys Gly Phe Leu Ile Gly Gly Ile Ala
305                 310                 315                 320

Leu Tyr Leu Gly Leu Tyr Ala Val Gly Asn Phe Leu Pro Ser Glu Asp
                325                 330                 335

Ser Met Leu Gln His Arg Asp Ala Leu Arg Ser Leu Thr Asp Leu Asn
            340                 345                 350

Gln Asp Pro Ser Arg Val Leu Ser Ala Lys Asn Gly Ser Ser Gly Asp
    355                 360                 365

Gly Ile Ala His Thr Glu Gly Ile Leu Asn Arg Asn His Arg Asp Ala
370                 375                 380

Ser Ser Leu Thr Asn Leu Lys Arg Ala Asn Ala Asp Val Glu Ile Ile
385                 390                 395                 400

Thr Pro Arg Ser Pro Met Gly Lys Glu Ser Met Val Thr Phe Ser Asn
                405                 410                 415

Thr Leu Pro Arg Ala Asn Thr Pro Ser Val Glu Asp Pro Val Arg Arg
            420                 425                 430

Asn Ala Ser Ile His Ala Ser Met Asp Ser Ala Arg Ser Lys Gln Leu
    435                 440                 445

Leu Thr Gln Trp Lys Ser Lys Asn Glu Ser Arg Lys Met Ser Leu Gln
450                 455                 460

Val Met Asp Ser Glu Pro Glu Gly Gln Ser Pro Pro Arg Ser Ile Glu
465                 470                 475                 480

Met Arg Ser Ser Glu Pro Ser Arg Val Gly Val Asn Gly Asp His
                485                 490                 495

His Val Pro Gly Asn Gln Tyr Leu Lys Ile Gln Pro Gly Thr Val Pro
            500                 505                 510

Gly Cys Asn Asn Ser Met Pro Ala Gly Pro Arg Val Ser Ile Gln Ser
    515                 520                 525

Arg Pro Gly Ser Ser Gln Leu Val His Ile Pro Glu Glu Thr Gln Glu
530                 535                 540

Asn Ile Ser Thr Ser Pro Lys Ser Ser Ala Arg Ala Lys Trp Leu
545                 550                 555                 560

Lys Ala Ala Glu Lys Thr Val Ala Cys Asn Arg Gly Asn Asn Gln Pro
                565                 570                 575

Arg Ile Met Gln Val Ile Ala Met Ser Lys Gln Gln Gly Val Leu Gln
            580                 585                 590

Ser Ser Pro Lys Asn Ala Glu Gly Ser Thr Val Thr Cys Thr Gly Ser
    595                 600                 605
```

```
Ile Arg Tyr Lys Thr Leu Thr Asp His Glu Pro Ser Gly Ile Val Arg
    610                 615                 620
Val Glu Ala His Pro Glu Asn Asn Arg Pro Ile Ile Gln Ile Pro Ser
625                 630                 635                 640
Ser Thr Glu Gly Glu Gly Ser Gly Ser Trp Lys Trp Lys Ala Pro Glu
                645                 650                 655
Lys Ser Ser Leu Arg Gln Thr Tyr Glu Leu Asn Asp Leu Asn Arg Asp
                660                 665                 670
Ser Glu Ser Cys Glu Ser Leu Lys Asp Ser Phe Gly Ser Gly Asp Arg
            675                 680                 685
Lys Arg Lys His Ile Asp Ser Asn Glu His His His Gly Ile Thr
690                 695                 700
Thr Ile Arg Val Thr Pro Val Glu Gly Ser Glu Ile Gly Ser Glu Thr
705                 710                 715                 720
Leu Ser Val Ser Ser Arg Asp Ser Thr Leu Arg Arg Lys Gly Asn
                725                 730                 735
Ile Ile Leu Ile Pro Glu Arg Ser Asn Ser Pro Glu Asn Thr Arg Asn
                740                 745                 750
Ile Phe Tyr Lys Gly Thr Ser Pro Thr Arg Pro Tyr Lys Asp
            755                 760                 765

<210> SEQ ID NO 10
<211> LENGTH: 748
<212> TYPE: PRT
<213> ORGANISM: Rattus norvegicus

<400> SEQUENCE: 10

Met Ile Ala Lys Lys Glu Lys Asn Lys Thr Pro Lys Asp Ser Met Thr
1               5                   10                  15
Leu Leu Pro Cys Phe Tyr Phe Val Glu Leu Pro Ile Val Ala Ser Ser
                20                  25                  30
Val Val Ser Leu Tyr Phe Leu Glu Leu Thr Asp Leu Phe Gln Pro Ala
            35                  40                  45
Lys Val Gly Phe Gln Cys His Asp Arg Ser Leu Ser Met Pro Tyr Val
        50                  55                  60
Glu Thr Asn Glu Glu Leu Ile Pro Leu Leu Met Leu Leu Ser Leu Ala
65              70                  75                  80
Phe Ala Ala Pro Ala Ala Ser Ile Met Val Gly Glu Gly Met Val Tyr
                85                  90                  95
Cys Leu Gln Ser Arg Leu Trp Gly Arg Gly Pro Gly Gly Val Glu Gly
                100                 105                 110
Ser Ile Asn Ala Gly Gly Cys Asn Phe Asn Ser Phe Leu Arg Arg Thr
            115                 120                 125
Val Arg Phe Val Gly Val His Val Phe Gly Leu Cys Ala Thr Ala Leu
        130                 135                 140
Val Thr Asp Val Ile Gln Leu Ala Thr Gly Tyr His Thr Pro Phe Phe
145                 150                 155                 160
Leu Thr Val Cys Lys Pro Asn Tyr Thr Leu Leu Gly Thr Ser Cys Glu
                165                 170                 175
Ala Asn Pro Tyr Ile Thr Gln Asp Ile Cys Ser Gly His Asp Thr His
                180                 185                 190
Ala Ile Leu Ser Ala Arg Lys Thr Phe Pro Ser Gln His Ala Thr Leu
            195                 200                 205
Ser Ala Phe Ala Ala Val Tyr Val Ser Met Tyr Phe Asn Ser Val Ile
        210                 215                 220
```

```
Ser Asp Ala Thr Lys Leu Leu Lys Pro Ile Leu Val Phe Ala Phe Ala
225                 230                 235                 240

Ile Ala Ala Gly Val Cys Gly Leu Thr Gln Ile Thr Gln Tyr Arg Ser
            245                 250                 255

His Pro Val Asp Val Tyr Ala Gly Phe Leu Ile Gly Ala Gly Ile Ala
            260                 265                 270

Ala Tyr Leu Ala Cys His Ala Val Gly Asn Phe Gln Ala Pro Pro Ala
        275                 280                 285

Glu Lys Val Pro Thr Pro Ala Pro Ala Lys Asp Ala Leu Arg Val Leu
        290                 295                 300

Thr Gln Arg Gly His Glu Ser Met Tyr Gln Gln Asn Lys Ser Val Ser
305                 310                 315                 320

Thr Asp Glu Leu Gly Pro Pro Gly Arg Leu Gly Val Pro Arg Pro
                325                 330                 335

Val Ala Arg Glu Lys Thr Ser Leu Gly Ser Leu Lys Arg Ala Ser Val
            340                 345                 350

Asp Val Asp Leu Leu Ala Pro Arg Ser Pro Met Gly Lys Glu Gly Met
        355                 360                 365

Val Thr Phe Ser Asn Thr Leu Pro Arg Val Ser Thr Pro Ser Leu Asp
        370                 375                 380

Asp Pro Ser Arg Arg His Met Thr Ile His Val Pro Leu Asp Ala Ser
385                 390                 395                 400

Arg Ser Arg Gln Leu Ile Ser Glu Trp Lys Gln Lys Ser Leu Glu Gly
                405                 410                 415

Arg Gly Leu Gly Leu Pro Asp Glu Ala Ser Pro Ala His Leu Arg Ala
            420                 425                 430

Pro Ala Glu Gln Val Ala Glu Glu Glu Glu Glu Glu Glu Glu Glu Glu
        435                 440                 445

Glu Glu Glu Glu Glu Glu Glu Glu Glu Glu Gly Pro Val Pro Pro
        450                 455                 460

Ser Leu Tyr Pro Thr Val Gln Ala Arg Pro Gly Leu Gly Pro Arg Val
465                 470                 475                 480

Ile Leu Pro Pro Arg Pro Gly Pro Gln Pro Leu Ile His Ile Pro Glu
            485                 490                 495

Glu Val Val Gln Ala Gly Ala Gly Leu Ser Pro Lys Ser Ser Ala Ser
        500                 505                 510

Val Arg Ala Lys Trp Leu Ser Met Val Glu Lys Gly Gly Pro Val
        515                 520                 525

Ala Val Ala Pro Pro Gln Pro Arg Val Ala Asn Pro Pro Arg Leu Leu
        530                 535                 540

Gln Val Ile Ala Met Ser Lys Ala Ala Gly Gly Pro Lys Ala Glu Thr
545                 550                 555                 560

Ala Ser Ser Ser Ala Ser Ser Asp Ser Ser Gln Tyr Arg Ser Pro
                565                 570                 575

Ser Asp Arg Asp Ser Ala Ser Ile Val Thr Ile Asp Ala His Ala Pro
            580                 585                 590

His His Pro Val Val His Leu Ser Ala Gly Ser Thr Pro Trp Glu Trp
        595                 600                 605

Lys Ala Lys Val Val Glu Gly Glu Gly Tyr Glu Leu Gly Asp Leu
        610                 615                 620

Ala Arg Gly Phe Arg Ser Ser Cys Lys Gln Pro Gly Ile Gly Pro Gly
625                 630                 635                 640
```

```
Ser Pro Val Ser Asp Val Asp Gln Glu Glu Pro Arg Phe Gly Ala Val
                645                 650                 655

Ala Thr Val Asn Leu Ala Thr Gly Glu Gly Leu Pro Pro Gly Ala
            660                 665                 670

Ser Glu Gly Ala Leu Gly Ala Gly Ser Arg Glu Ser Thr Leu Arg Arg
        675                 680                 685

Gln Val Gly Ala Leu Gly Glu Arg Glu Val Glu Ala Glu Ala Glu Ser
    690                 695                 700

Tyr Tyr Arg Arg Met Gln Ala Arg Arg Tyr Gln Asp Ala Trp Gln Ser
705                 710                 715                 720

Cys Asp Gly Gln Lys Ala Gly Trp Gly Val Thr Thr Ala Pro Pro Ile
                725                 730                 735

Lys Val His Gly Asn Arg Lys Lys Lys Lys Lys
            740                 745

<210> SEQ ID NO 11
<211> LENGTH: 325
<212> TYPE: PRT
<213> ORGANISM: Rattus norvegicus

<400> SEQUENCE: 11

Met Ala Val Glu Asn Asn Thr Gln Arg Ser Tyr Ser Ile Ile Pro Cys
1               5                   10                  15

Phe Ile Phe Val Glu Leu Val Ile Met Ala Gly Thr Val Leu Leu Ala
                20                  25                  30

Tyr Tyr Phe Glu Cys Thr Asp Thr Phe Gln Val His Ile Gln Gly Phe
            35                  40                  45

Phe Cys Gln Asp Gly Asp Leu Met Lys Pro Tyr Pro Gly Thr Glu Glu
        50                  55                  60

Glu Ser Phe Ile Ser Pro Leu Val Leu Tyr Cys Val Leu Ala Ala Thr
65                  70                  75                  80

Pro Thr Ala Ile Ile Phe Ile Gly Glu Ile Ser Met Tyr Phe Ile Lys
                85                  90                  95

Ser Thr Arg Glu Ser Leu Ile Ala Glu Glu Lys Met Ile Leu Thr Gly
                100                 105                 110

Asp Cys Cys Tyr Leu Ser Pro Leu Leu Arg Arg Ile Val Arg Phe Ile
            115                 120                 125

Gly Val Phe Ala Phe Gly Leu Phe Ala Thr Asp Ile Phe Val Asn Ala
        130                 135                 140

Gly Gln Val Val Thr Gly His Leu Thr Pro Tyr Phe Leu Thr Val Cys
145                 150                 155                 160

Gln Pro Asn Tyr Thr Ser Thr Asp Cys Arg Ala His His Gln Phe Ile
                165                 170                 175

Asn Asn Gly Asn Ile Cys Thr Gly Asp Leu Glu Val Ile Glu Lys Ala
            180                 185                 190

Arg Arg Ser Phe Pro Ser Lys His Ala Ala Leu Ser Ile Tyr Ser Ala
        195                 200                 205

Leu Tyr Ala Thr Met Tyr Ile Thr Ser Thr Ile Lys Thr Lys Ser Ser
    210                 215                 220

Arg Leu Ala Lys Pro Val Leu Cys Leu Gly Asp Leu Cys Thr Ala Phe
225                 230                 235                 240

Leu Thr Gly Leu Asn Arg Val Ser Glu Tyr Arg Asn His Cys Ser Asp
                245                 250                 255

Val Ile Ala Gly Phe Ile Leu Gly Thr Ala Val Ala Leu Phe Leu Gly
            260                 265                 270
```

```
Met Cys Val Val His Asn Phe Lys Gly Thr Gln Gly Ser Ala Ser Lys
        275                 280                 285

Pro Lys Pro Glu Asp Pro Arg Gly Val Pro Leu Met Ala Phe Pro Arg
    290                 295                 300

Ile Glu Ser Pro Leu Glu Thr Leu Ser Ala Gln Asn His Ser Ala Ser
305                 310                 315                 320

Met Thr Glu Val Thr
                325

<210> SEQ ID NO 12
<211> LENGTH: 343
<212> TYPE: PRT
<213> ORGANISM: Rattus norvegicus

<400> SEQUENCE: 12

Met Ala Gly Gly Arg Pro His Leu Lys Arg Ser Phe Ser Ile Ile Pro
1               5                   10                  15

Cys Phe Val Phe Val Glu Ser Val Leu Leu Gly Ile Val Val Leu Leu
                20                  25                  30

Ala Tyr Arg Leu Glu Phe Thr Asp Thr Phe Pro Val His Thr Gln Gly
            35                  40                  45

Phe Phe Cys Tyr Asp Ser Ala Tyr Ala Lys Pro Tyr Pro Gly Pro Glu
        50                  55                  60

Ala Ala Ser Arg Ala Pro Pro Ala Leu Ile Tyr Ala Leu Val Thr Ala
65                  70                  75                  80

Gly Pro Thr Leu Thr Ile Leu Leu Gly Glu Leu Ala Arg Ala Phe Phe
                85                  90                  95

Pro Ala Pro Pro Ser Ser Ser Pro Val Ser Gly Glu Ser Thr Ile Val
            100                 105                 110

Ser Gly Ala Cys Cys Arg Phe Ser Pro Pro Leu Arg Arg Leu Val Arg
        115                 120                 125

Phe Leu Gly Val Tyr Ser Phe Gly Leu Phe Thr Thr Thr Ile Phe Ala
    130                 135                 140

Asn Ala Gly Gln Val Val Thr Gly Asn Pro Thr Pro His Phe Leu Ser
145                 150                 155                 160

Val Cys Arg Pro Asn Tyr Thr Ala Leu Gly Cys Pro Pro Ser Pro
                165                 170                 175

Asp Arg Pro Gly Pro Asp Arg Phe Val Thr Asp Gln Ser Ala Cys Ala
            180                 185                 190

Gly Ser Pro Ser Leu Val Ala Ala Arg Ala Phe Pro Cys Lys
        195                 200                 205

Asp Ala Ala Leu Cys Ala Tyr Ala Val Thr Tyr Thr Ala Met Tyr Val
    210                 215                 220

Thr Leu Val Phe Arg Val Lys Gly Ser Arg Leu Val Lys Pro Ser Leu
225                 230                 235                 240

Cys Leu Ala Leu Leu Cys Pro Ala Phe Leu Val Gly Val Val Arg Val
                245                 250                 255

Ala Glu Tyr Arg Asn His Trp Ser Asp Val Leu Ala Gly Phe Leu Thr
            260                 265                 270

Gly Ala Ala Ile Ala Thr Phe Leu Val Thr Cys Val Val His Asn Phe
        275                 280                 285

Gln Ser Arg Pro His Ser Gly Arg Arg Leu Ser Pro Trp Glu Asp Leu
    290                 295                 300

Ser Gln Ala Pro Thr Met Asp Ser Pro Leu Glu Lys Asn Pro Arg Pro
```

```
                305                 310                 315                 320
Ala Gly Arg Ile Arg His Arg His Gly Ser Pro His Pro Ser Arg Arg
                    325                 330                 335

Thr Val Pro Ala Val Ala Thr
        340

<210> SEQ ID NO 13
<211> LENGTH: 5083
<212> TYPE: DNA
<213> ORGANISM: Homo sapiens

<400> SEQUENCE: 13
ggatccacta gtaacggccg ccagtgtgct ggaattcgcc cttgaagcca ttgcagcaac      60
agcttggagg agggagctgg acgtcgtctc tcgccagaaa acggggagc aggagccaga     120 ctaaaggagg aagaggactg gcccgctcag ggaatagctg ggttgctgca aaaaggggcg    180
gggagaaggc gggggcgctg catgcagcgc gctggctcca gcgtggccg cggggaatgt     240 gacatcagcg gcgccgggcg cttggggctg gaggaggcgg ctcgcctcag ctgcgctgtg    300
cacacctcgc ccggggagg acgcagaccc gggcaggcgg cagggatgtc ggcgaaggag     360
aggccaaagg gcaaagtgat caaggacagc gtcaccctcc tgccctgctt ttatttcgtc    420
gagttgccta tattggcatc atcggtggtt agcctctatt tcctcgaact cacagatgtc    480
ttcaaacctg tgcactctgg atttagctgc tatgaccgga gtcttagcat gccgtacatt    540
gaaccaaccc aggaggcaat tccattcctc atgttgctta gcttggcttt tgctggacct    600
gcaattacga ttatggtagg agaaggaatt ctctactgtt gcctctccaa aagaagaaat    660
ggggtcggac tagagcccaa cattaatgct ggaggctgca acttcaattc cttcctcaga    720
cgagctgtca gattcgttgg tgttcatgta tttggattat gctctacagc tctcattaca    780
gatatcatac agctgtccac aggatatcaa gcaccttact ttctgactgt gtgcaaacca    840
aactatacct ctctgaatgt atcttgcaaa gaaaattcct acattgtgga agatatttgc    900
tcaggatctg acctcacagt tatcaacagt ggcagaaagt ccttcccttc tcaacatgca    960
acccttgctg cctttgcagc tgtgtatgtt tcgatgtact tcaattccac attaacggat   1020
tcctctaagc ttctgaaacc tctcttggtc ttcacattta tcatctgtgg aataatctgc   1080
gggctaacac ggataactca gtataagaac cacccagttg atgtctattg tggctttta   1140 ataggaggag gaattgcact gtacttgggc ttgtatgctg tggggaattt cctgcccagt   1200
gatgagagta tgtttcagca cagagacgcc ctcaggtctc tgacagacct caatcaagat   1260
cccaaccgac ttttatctgc taaaaatggt agcagcagtg atggaattgc tcatacagaa   1320
ggcatcctca accgaaacca cagatgctag ctctctga caaatctcaa aagagcaaat    1380
gctgatgtgg aaatcattac tccacggagc ccatgggga aggagaacat ggttaccttc   1440
agcaatacct tgccgcgagc caataccca tctgtagaag accctgtcag aagaaatgcg    1500
agcattcatg cctctatgga ttccgctcga tcaaagcagc tcctcaccca gtggaagaat   1560
aagaatgaaa gtcgaaagtt gtccttgcaa gttatagagc ctgagcctgg gcagtcacca   1620
cccagatcca tagaaatgag gtcaagctca gagccatcga gggtagggt gaatggagac    1680 caccatggtc ctggcaatca gtacctcaaa atccagcctg cgctgtccc cggatgtaac   1740 aacagcatgc ctggagggcc aagagtgtcc attcagtccc gtcctgggtc ctcacagttg   1800
gtgcacatcc ctgaggagac tcaggaaaac ataagcacct cccccaaaag cagctctgct   1860
cgggccaagt ggttaaaagc tgctgaaaag actgtggcct gtaacagaag caacagccag   1920
```

-continued

```
ccccgaatca tgcaagtcat agccatgtcc aagcagcagg gtgtcctcca aagcagcccc    1980
aagaacactg aaggcagcac ggtctcctgc actggctcca tccgctataa aaccttgaca    2040
gaccatgagc ccagtgggat agtgagggtt gaggctcacc cagagaacaa caggcccatc    2100
atacagatcc cgtccactga aggtgaaggc agtggctcct ggaagtggaa agcccctgaa    2160
aagggcagcc ttcgccaaac ttacgagctc aacgatctca cagggactc agaaagctgt     2220
gagtctctga aagacagctt tggttctgga gatcgcaaga aagcaacat tgatagcaat     2280
gagcatcacc accacggaat taccaccatc cgcgtcaccc cagtagaggg cagcgaaatt    2340
ggctcagaga cgctgtccat ttcttcttcc cgcgactcca ccctgcggag aaagggcaat    2400
atcattctaa tccctgaaag aagcaacagc cccgaaaaca ctagaaatat cttctacaaa    2460
ggaacctccc ccacacgggc ttataaggat tgagtgatgt ccattccatc attagggcta    2520
ctcgcaaaag accatatgtt gattctacct gtgttctgtt ccagcgaatt gggaagtctc    2580
accaagctag attgtctacc atcagcccag aactctgtaa cttttcagaa ctgctatact    2640
caaacttgca gatctcacat caaggagagg gaaaagcaca atgcaagaac ctaactaacg    2700
tgatgatatg aagagttttc ttaagacctg tcgtcaaact taaaaggttt tgcagagggc    2760
agtatcaaaa gaaagtggtt ttcttcaaat gtatactatt ttacttcctg aatgtgccaa    2820
cttgggat ttttctttat agtgagctgt gggaacccag aacacacacg ttttccctac       2880
agcagaggcc atgcagtatt atatattcat tttgcagaat ctgcacctac agctcaatac    2940
gggtggtgct gattattata gtacatatac catgtaaact ctcaaactct atttagctgt    3000
gaaatagtgg tgtgcaattc cttgttaaag aaatgctact ttattaagaa gatgctggct    3060
gctttgtgtt agaataggac accccgcagc ttctctgtag tggctctgtc acagtcaaaa    3120
aatgaaaagg tttttgtgcg tttcttcaaa attctgcttt cttcaacatc aaaaattgtg    3180
tagaaatatt ttcagtgaaa gggaataact agtactttc tgcatagttt ttcttctgct      3240
tacttttat ttaagtatag gtactgctaa tgaatctgtt ttcttagtga gtaaatttgc      3300
ataattttat aaatattatt ttagagaatc ttttgaaatt gttgtgatca tattttgctt    3360
tctatggctt ctccttaact tattgattaa tttttttgaag ttatagatat gttctcctat   3420
tttaaaagca aaaataacaa ttgacattcc ttgagcaaaa tatactgctg tgaatttgca    3480
aacaagaaat ctgagccaaa acttgacatt gtgggttaca ttgccagaaa tgttggtcaa    3540
gtttgccctt agatgtctac aactagctgg cataggttgc catcttaaca agtaatctaa    3600
aagtcccatt cggttctaca ttattaactt tttttttcta tatcctgatg accagtaaat    3660
tagagccaca ctggttaagt ttgactcgtc tctaaaacgt ttttgttaat tggacaccaa    3720
gaggaagaat ctgaaaaaaa aatgcatgtt ggtaagtaaa agtatctcac ggtacaaatt    3780
aagaatgact ttcttcaaaa tatctgaata ggtgcagttt tagtttaaca tgcaaacaac    3840
cattgttgct acctatcctg aatcaagcct tgagcctaaa tcaaagcaaa ccaataccat    3900
tgataagaag aagataaaaa caaaatattt tggagtgttt tccaacttaa agtatgaaga    3960
catactcagt tcttggaact tagtattaaa ccttttttat gccatttcat aagaattccg    4020
atatatactt gatgattgcc aaggggatga aaggaaacaa cagagatggt tgatctgatc    4080
ttagctcact ttccaataac agaaggagtt gtttacagat gaatagtatc acatcattat    4140
caatttccac atgaaaaagg tggagctttc tagaaaaacc aacctctaag gcattaggaa    4200
tttagctgaa accagcagaa ttgaaaactc tggcaataaa acatggactc aaccatatcc    4260
```

```
cttctggcaa tttccttctc agagagggga gtgggaataa aatgttgcct tccccacttc    4320
tcaccaccac cgccatcatg acgctcatac tggcttttgc ctgtttgtag aggaaaaggt    4380
gggctggttt tagtactctg aaggacaaaa acaagcaaac aaaaacccct gctgcagcat    4440
ttcaggtgca gtatgatatt tcctaatctt tcctatttct taacaaaaga ttttaaagta    4500
cttctctagt cattgaagtt ttttttttctt tacataaata ttgatatatt cttttctac    4560 tcaaagtgcc aaaggctaca gttttaatg acttaacaaa ttgtaccaca ttgttaagga    4620
catataatga tagacactag aactcagacc tctgcatgta tatttgataa catgtctttt    4680
gtaaaacaaa aattacaaaa aaatttgttt acattccact ggtaccttaa tttaaaataa    4740
atcagactaa aaggtggtat ctcttcttag tgttctattt atcttatttg ctaatgggag    4800
cacttcttcc tttgttaggc tgtgctttac tgataaaacc aagtattgaa taagagagt     4860 taattatctt tttaaagtaa ataaaattat gaaatatat atagtatata taaagtcctg     4920
tgtttaaaaa aatgttatgc aatgttttcc aaactgataa agtttgtaaa gtgctataaa    4980 tgtatttgt taagtacaga taaaagctat tgtgtgagta tattgtgcta aaatcataga     5040
aataaagatt agatttcttc atcaaaaaaa aaaaaaaaa aaa                       5083

<210> SEQ ID NO 14
<211> LENGTH: 2356
<212> TYPE: DNA
<213> ORGANISM: Homo sapiens

<400> SEQUENCE: 14
aggagacgcg ctttgtgctg ggcgccggcc gcgccagcca cggcctgcgg cgcccgcggc      60
accatgatct ccaccaagga gaagaacaag atcccgaagg acagcatgac gcttctgccc     120
tgcttctact tcgtggagct gcccatagtg gcttcttcca tcgtatcctt gtacttcctg     180
gagctgaccg acctcttcaa gccggccaag gtgggcttcc agtgctatga ccgcactctc     240
tccatgccct acgtggagac caacgaggag ctcatcccgc tgctgatgct gctcagcttg     300
gccttcgcgg cccctgccgc ctcgatcatg gtggccgagg gcatgttgta ctgtctgcag     360
tcccggctgt ggggccgtgc cgggggggccc gccggggcgg agggcagcat caacgccggc     420
ggctgcaact tcaactcctt cctgcggcgt acggtgcggt ttgtggggtgt ccacgtgttc     480 ggcctgtgtg ccacagccct ggtgacggac gtgatccagc tggccacggg ttaccacact     540
cccttcttcc tcaccgtctg caagcccaac tacactctcc tgggcacgtc ctgcgaggtc     600
aacccctaca tcacgcagga catctgctcc ggccacgaca tccacgccat cctgtctgca     660
cggaagacct tcccgtccca gcacgccacg ctgtcagcct tcgccgcggt ctatgtgtcg     720
gtgagtccgg cacctcactg cccttcccag gccctcttgc tgaccgtgg ggagccctcc     780 ctgaccccaa ccccccatgcc ccagatgtac ttcaactcgg tcatctcgga caccaccaag     840
ctgctgaagc ccatcctggt cttcgccttt gccatcgccg cgggcgtatg cgggctcacg     900
cagatcacgc agtaccgcag ccaccctgtg gacgtgtatg ccggcttcct catcggggcg     960
ggcatcgctg cctacctggc ctgccacgcg gtgggcaact ccaggcccc acctgcagag    1020 aagcccgcgg ccccggcccc cgccaaggac gcgctgcggg ccctgacgca gcgggccac     1080 gactcggttt atcagcagaa taagtcggtg agcaccgacg agctgggggcc cccagggcgg    1140 ctggaggggcg cgccccggcc cgtggccccgc gagaagacct cgctgggcag cctgaagcgc    1200
gccagcgtgg acgtggacct gctggccccg cgcagcccca tggccaagga gaacatggtg    1260
accttcagcc acacgctgcc cagggccagc gcgccctcgc tggacgaccc cgcgcgccgc    1320
```

```
cacatgacca tccacgtgcc gctggacgcc tcgcgctcca agcagctcat cagcgagtgg    1380
aagcagaaga gcctggaggg ccgcggcctg ggctgcccg acgacgccag ccccgggcac     1440
ctgcgcgcgc ccgccgaacc catggcgag gaggaggaag aggaggagga cgaagaggaa     1500
gaggaggagg aggaagagga ggaggacgag ggcccggccc cgccctcgct ctaccccacc    1560
gtgcaggcgc ggccggggct ggggcctcgg gtcatcctcc caccgcgcgc ggggccgccg    1620
ccgctggtgc acatcccgga ggagggcgcg cagacggggg ccggcctgtc ccccaaaagc    1680
ggcgccgggg tgcgcgccaa gtggctcatg atggccgaga gagcggggc ggcagtggcc     1740 aaccctccgc ggctgctgca ggtcatcgcc atgtccaagg ctccgggcgc gccgggcccc    1800
aaggcggccg agacggcgtc gtcgtccagc gccagctccg actcctcgca gtaccggtcg    1860
ccgtcggacc gcgactccgc cagcatcgtg accatcgacg cgcacgcgcc gcaccacccc    1920
gtggtgcacc tgtcggccgg cggcgcgccc tgggagtgga aggcggcggg cggcggggcc    1980
aaggcggagg ccgacggcgg ctacgagctg ggggacctgg cgcgcggctt ccgcggcggg    2040
gccaagcccc cggcgtgtc ccccggctcg tcggtcagcg acgtggacca ggaggagccg      2100
cggttcgggg ccgtggccac cgtcaacctg gccacgggcg aggggctgcc cccgctgggc    2160
gcggccgatg gggcgctggg cccgggcagc cgggagtcca cgctgcggcg ccacgcgggc    2220
ggcctggggc tggcggagcg cgaggcggag gcggaggcca agggctactt ccgcaagatg    2280
caggcgcgcc gcttccccga ctagcgcggc ggggccgggg gcgggcgggg ggcgggccga    2340
gggcgcgggc ggccgc                                                    2356

<210> SEQ ID NO 15
<211> LENGTH: 1306
<212> TYPE: DNA
<213> ORGANISM: Homo sapiens

<400> SEQUENCE: 15
atggtgtgag aaatggctgt aggaaacaac actcaacgaa gttattccat catcccgtgt      60
tttatatttg ttgagcttgt catcatggct gggacagtgc tgcttgccta ctacttcgaa     120
tgcactgaca cttttcaggt gcatatccaa ggattcttct gtcaggacgg agacttaatg     180
aagccttacc cagggacaga ggaagaaagc ttcatcaccc ctctggtgct ctattgtgtg     240
ctggctgcca ccccaactgc tattattttt attggtgaga tatccatgta tttcataaaa     300
tcaacaagag aatccctgat tgctcaggag aaaacaattc tgaccggaga atgctgttac     360
ctgaacccct acttcgaagg atcataaga ttcacagggg tgtttgcatt tggactttt      420 gctactgaca tttttgtaaa cgccggacaa gtggtcactg gcacttaac gccatacttc    480 ctgactgtgt gcaagccaaa ctacaccagt gcagactgcc aagcgcacca ccagtttata    540
aacaatggga catttgtac tggggacctg aagtgatag aaaaggctcg agatcctttt     600
ccctccaaac acgctgctct gagcatttac tccgccttat atgccacgat gtatattaca    660
agcacaatca agacgaagag cagtcgactg gccaagccgg tgctgtgcct cggaactctc    720
tgcacagcct tcctgacagg cctcaaccgg gtctctgagt atcggaacca ctgctcggac    780
gtgattgctg gtttcatcct gggcactgca gtggccctgt ttctgggaat gtgtgtggtt    840
cataacttta aggaacgca aggatctcct tccaaaccca gcctgagga tccccgtgga     900 gtaccctaa tggctttccc aaggatagaa agccctctgg aaaccttaag tgcacagaat    960
cactctgcgt ccatgaccga agttacctga gacgactgat gtgtcacaag ctgttttta   1020
```

-continued

| | |
|---|---|
| aaatcatctt ccaattctat acttcaaaac acacagttgc tcaatgtcaa actgtgatga | 1080 |
| caaatattac gtttatctag ttagaagcta atgttttgta cattttttgt atgaggaagt | 1140 |
| gatgtagctt gccctgattt tttttttttt ttttggtcag ctttaatata tttatgccag | 1200 |
| aattttaaaa ccaacaaaat tttcttgttc aagcgtgcat tgaagaacca catttattca | 1260 |
| atggttgacg ttgttttgtg atatttgtac acaaattttc tttttt | 1306 |

<210> SEQ ID NO 16
<211> LENGTH: 2680
<212> TYPE: DNA
<213> ORGANISM: Homo sapiens

<400> SEQUENCE: 16

| | |
|---|---|
| agtctgcgcg gcgcggccag gcccggccga ccgcgtctcg gtcttcgcgt ctgccagcct | 60 |
| ggctggcagt ccgtctgtcc atcccgccgc gccggggcag tctaggcgga gcggggggctc | 120 |
| aggcggcggc ggcctcgacg cgagtgagtg tcgtggttgg ggtgctggac ccagagtgcc | 180 |
| taccctcgcc tgcctgggcc tcagtttcca catctgcaca atgggggtga ccatccctgc | 240 |
| cctgctggct gccaggagcg gctgtgagtc ttcaggcgtg gatgcagcct gggggaagcc | 300 |
| ataggggcgct ttcacaggcc tggccttcac catggcggga gggagaccgc atctgaagag | 360 |
| gagtttctcc atcatcccct gctttgtctt cgtggagtcg gtgctgctgg cattgtgat | 420 |
| cctgcttgct taccgcctgg agttcacgga caccttccct gtgcacaccc agggattctt | 480 |
| ctgctatgac agtacctacg ccaagccta cccagggcct gaggctgcca gccgagtgcc | 540 |
| tcctgctctt gtctacgcac tggtcactgc cgggcccacc ctcacgatcc tgctgggaga | 600 |
| gctggcgcgt gccttttttcc ctgcaccacc ttcagccgtc ccagtcatcg gggagagcac | 660 |
| catcgtgtct ggggcctgct gccgcttcag ccccccagtg cggaggctgg tccgcttcct | 720 |
| gggggtctac tccttcggcc tcttcaccac gaccatcttc gccaacgcgg ggcaggtggt | 780 |
| gaccggcaat cccacgccac acttcctgtc cgtgtgccgc cccaactaca cggccctggg | 840 |
| ctgcctgcca ccttctccgg atcggccagg tcccgaccgc tttgtcactg accagggtgc | 900 |
| ctgcgctggc agtcccagcc tcgtggccgc gcgcgccgc gccttcccct gcaaggatgc | 960 |
| ggccctctgc gcctacgcgg tcacctacac agcgatgtac gtgactctcg tgttccgcgt | 1020 |
| gaagggctcc cgcctggtca aaccctcgct ctgcctggcc ttgctgtgcc cggccttcct | 1080 |
| ggtgggcgtg gtccgcgtgg ccgagtaccg aaaccactgg tcggacgtgc tggctggctt | 1140 |
| cctgacaggg gcggccatcg ccaccttttt ggtcacctgc gttgtgcata actttcagag | 1200 |
| ccggccaccc tctggccgaa ggctctctcc ctgggaggac ctgggccaag cccccaccat | 1260 |
| ggatagcccc ctcgaaaaga acccgaggtc tgcaggccgc attcgacacc ggcacggctc | 1320 |
| accccatcca agtcgcagaa ctgcgcccgc cgtggccacc tgatccccag ctgtgtctcc | 1380 |
| tccagggccc cagccatgtg ttcgtcgccc cgtgtgcccc gtcctcgatt gaggtctgag | 1440 |
| ccgacgccct tgcccctgcc cctacccctg ccagcgccca ccccagcca gggcccctcg | 1500 |
| ccttcctccc ctggacctgg ggggccaggc gggggtggtg gacgtggccg gaagctgctg | 1560 |
| ctgcccacgc ccctgctgcg ggacctgtac accctgagtg gactctatcc ctccccttc | 1620 |
| caccgggaca acttcagccc ttacctgttt gccagccgtg accacctgct gtgaggcccg | 1680 |
| accacccacc cagaatctgc ccagtcccca cttcttccct gccacgcgtg tgtgtgcgtg | 1740 |
| tgccacgtga gtgccaaagt cccctgcccc ccaagccagc cagacccaga cattagaaga | 1800 |
| tggctagaag gacatttagg agacatctgc ctctctggcc ctctgagata tcccgatggg | 1860 |

```
cacaaatgga aggtgcgcac ttgcccctac tattgcccTT ttaagggcca aagcttgacc    1920
ccattggcca ttgcctggct aatgagaacc cctggttctc agaattttaa ccaaaaggag    1980
ttggctccaa ccaatgggag ccttcccctc acttcttaga atcctcctgc aagagggcaa    2040
ctccagccag tgttcagcga ctgaacagcc aataggagcc cttggtttcc agaatttcta    2100
gagtgggtgg gcatgattcc agtcaatggg ggaccgcccg tgtctaagca tgtgcaaagg    2160
agaggaggga gatgaggtca ttgtttgtca ttgagtcttc tctcagaatc agcgagccca    2220
gctgtagggt gggggggcagg ctcccccatg gcagggtcct tggggtaccc cttttcctct    2280
cagcccctcc ctgtgtgcgg cctctccacc tctcacccac tctctcctaa tccctactt     2340 aagtagggct tgccccactt cagaggtttt ggggttcagg gtgctgtgtc tccccttgcc    2400
tgtgcccagg tcatcccaaa cccttctgtt atttattagg gctgtgggaa gggttttttct   2460 tcttttctt ggaacctgcc cctgttcttc acactgcccc ccatgcctca gcctcataca     2520
gatgtgccat catgggggggc atgggtggag cagaggggct ccctcacccc gggcaggcaa   2580
aggcagtggg tagaggaggc actgccccccc tttcctgccc cctcctcatc tttaataaag   2640
acctggcttc tcatctttaa taaagacctg tttgtaacag                          2680

<210> SEQ ID NO 17
<211> LENGTH: 5708
<212> TYPE: DNA
<213> ORGANISM: Mus musculus
<220> FEATURE:
<221> NAME/KEY: misc_feature
<222> LOCATION: (460)..(460)
<223> OTHER INFORMATION: n is a, c, g, or t

<400> SEQUENCE: 17
ygagcgatga tgccccattt accctttctc ttcagatgca ggaaatttc  actctgttcc      60 ccagctgatt ggagctttt ctaggtgctt ccctgggagt tacctcccta gagatcagca     120
ggcagggctg tcacgcttgg gtagcagcca gctcccagtg aattccttct gtggcctact    180
tgtccttatg aagtccgagt tttaatttg cacaggtagg aggtctcttt tgctatggat     240
agggcggata acggtgctac cattagaaaa caggcttctg ttttctagga aggcaagagg    300
aaccccaggt aggggacctt gtgagaccag gtgacttggc tcctcagcct tgcttctaca    360
gaaaccagga gtgcttcccc ccactcttcc ctatttttga cgtcaagctc aaccagccag    420
cagaggagcc tcacgcttg ggcggtggag agagagcccn aggagagtgg cagggagggg    480
aagccatctc agcaacagct tggagaggga gctgctatcc cttgcccgca aaacacggac    540
taaagccagg ctgaagaaga cctgcggcct cgggctcggg gatccgcggg gttactgcaa    600
agaagggcgg ggaaaaggcg ggggcgctgc atgcaacgcg ctggttccag cggtgcccgc    660
ggggaatgtg acatcagcgg cgccgggcgc ttgcggctgg agcaggcagc tcgcctcggt    720
ggccgcacgg tgcacacctc gcccggggga ggacttggag cccggcaggc ggccgggatg    780
tcggcgaagg agaggccaaa gggcaaagtg atcaaggaca gcgtcaccct cctgccctgt    840
ttttatttcg ttgagttgcc tatattggca tcatcagtgg ttagcctcta cttcttggaa    900
ctcacagatg tcttcaaacc tgtgcactct ggattcagtt gctatgatag gagtcttagc    960
atgccgtaca ttgagccaac ccaggaggcc ataccattcc ttatgttgct tagcttggct    1020
tttgctggac ctgcaattac gatcatggtg ggtgaaggga ttctatactg ctgcctctcc    1080
aaaagaagaa acggagctgg attggagcct aacatcaacg ccggaggctg caacttcaac    1140
```

```
tcctttctca ggagagccgt cagattcgtt ggtgtccatg tgtttggact gtgctccaca    1200
gctctcatta cagatatcat acagctctcc acaggatatc aggcaccata ctttctgact    1260
gtgtgcaagc caaactatac ctctctgaat gtatcctgca agaaaactc ctacatcgtg     1320 gaagatattt gttcaggatc tgaccttaca gtcatcaaca gtggcagaaa gtcattccca    1380
tcccaacatg cgaccctcgc tgcctttgcc gctgtgtatg tgtccatgta cttcaattcc    1440
acattaaccg attcctctaa gctcctgaaa cctctcttgg tcttcacatt tatcatctgt    1500
gggatcatct gcggactaac acggataact caatataaga accatccagt cgatgtctat    1560
tgtggctttt taataggagg aggaatcgca ctatatttgg gcctgtatgc tgtagggaat    1620
tttttgccta gtgaagacag tatgcttcag cacagagatg ccctcaggtc actgacagac    1680
ctcaatcaag accccagcag ggttttatca gctaaaaatg gtagcagtgg tgatggaatt    1740
gctcacacag agggtatcct caaccgaaac cacagggatg caagctcctt gacaaatctc    1800
aagagggcca acgctgacgt agaaatcatc actcctagga gccccatggg gaaggaaagc    1860
atggtgacct tcagcaacac gctgcccagg gccaacaccc cctccgtgga agacccagtg    1920
agaagaaatg cgagcatcca tgcctctatg gattctgccc ggtccaaaca gctccttacc    1980
cagtggaaga gcaagaatga gagtcgtaag atgtccctac aggttatgga cactgaacca    2040
gaaggccagt caccacccag gtccatagaa atgaggtcca gctcagagcc ctcgagggtg    2100 gggtgaacg gagatcacca tgtccctggc aatcagtacc tcaagataca gcctggcaca    2160
gtccccgggt gcaacaatag tatgccggga gggccacgcg tgtccatcca gtcccgccct    2220
ggctcttccc aattggtgca catccccgag gagacccagg aaaacataag cacctcgccc    2280
aagagcagtt ctgcgcgagc caagtggctg aaagcagctg agaagaccgt ggactgtaac    2340
cggagcaaca accagccacg catcatgcag gtcatcgcca tgtccaagca gcagggcgtg    2400
ctgcagagca gccccaagaa tgccgaaggt agcactgtca cctgcacagg ttccatccgc    2460
tacaaaaccc tgactgacca tgagcccagc ggcatcgtgc gagtggaggc tcatcccgag    2520
aacaacaggc ccatcattca gatcccgtcg tccactgagg gtgaaggcag cggctcctgg    2580
aagtggaaag ttccggagaa aagtagtctg cgccaaacct atgagctcaa cgacctcaac    2640
agggactcag aaagctgtga gtccctcaaa gacagctttg gttctggaga tcgcaaaaga    2700
agcaacatcg acagcaatga gcaccaccac cacggcatca ccaccatccg agtgaccccg    2760
gtggagggca gcgagatagg ctcagagacg ctgtccgtgt cctcctcacg cgactccacc    2820
ctgcgcagga agggcaacat catcttgatc ccggaaagaa gcaacagccc tgaaaacaca    2880
agaaacatct tctacaaagg aacctccccc acgcgggctt ataaggattg agagatggcg    2940
gcccttcttg tcatcatttt gatgacaccc ccacctcccc atccccacc ctcaccccaa     3000 gaccactcgt ttattgtacc ttgtgctctt ttgggttttt tgttttgttt tgtttggggg    3060
cctttttttt tccctagaag atatggagag ccttcttgtc caactagatt gttcaccatc    3120
agcctggaac tctcactgaa ccaccacaga aatcgtggcg attttacacc aagggaaagg    3180
aaaagcacaa agcaagaccc gaactaaact catcatcaga acagttctta agacacaggc    3240
tttgcagaag gtagtattaa gataaagtgg tttcctccga tgtatagtat ttaactttct    3300
gaatgtgcca acttaatgga gttttttttt ttcattataa ttagctgtgg gaacccaaaa    3360
cacataggtt ttcccaacag cagaggccat gcggtattat atattattca tttttgcaga    3420
ctctgcacca gaagagcaga ctgggtggtg ctgattatca cagtgcatct accatttaaa    3480
ctctcaaact ctatgtagct gtgaaatagt ggtgtgcaac tcctcgtcag agaaatgcta    3540
```

```
cttcattcag aagacgccag tgactttgtg ttagaataga ccattcttgg cttccctgta    3600
gtggctctct cacagttgaa aagaaagaa aagaaaaga aaagaaaga gagagagaga      3660
aagagagaaa gaaagaaaga aagaaagaaa gaaagaaaga aagaaagaaa gaaagaaaga   3720
aagaaagaaa gaaagaaaga aagaaagaat tggatgaatt ggacagggct ttgagcattt   3780
ctttgaaaga tgcttttttt caacatctga aagcttgtag gaatgttttc agtgaaacag   3840
aataactagt tctctgcatc gttttttcttc tttttattta agtattggta atgctgcttt  3900
ctggtttttt gttttttgtt ttagtgagtg catttgcata tttaaaatac attgttttag   3960
agaatatttt gaaattatta tgattacatt ttccatttta tggctttacc ttagtttatt   4020
aagtttctg agggttacac atattcttct attttaagaa agcaaaagtg acaacttgca    4080
ttctttgtgc aaaatacact gctgtgaggt cctacactag aaatctgagc caaaggttga   4140
aactgtgcgt gccaatgcca gatacgctgg tcaaggtcaa gatgtctcca atccgatggc   4200
ataggttatc acatcagtaa gtaatcccaa aatttcattt tgttccagag catttcattt   4260
tcatgttatc ttgataatca ccatattgga gccacagtgg gggtgagttt gactcccttt   4320
cctgacacac ttttaactgc acaccaacag taagaatcta ggcaaatgct aattgataaa   4380
tagatgtgta tcacagtata agtttagaaa gcatatcttc aaaatgtcag accaggtaaa   4440
gctttcgtgc ttagagtata accaacagtt ttggatgtct gtcttgaatc tagaaccta   4500
agcctaaatc aaaggaaacc ttactgttga tagcaagaag ataacaacat attttttgaag 4560
tggttttcca agctagctgt ttaaagtgtg gagaaggatt tggttcttga aatttggtat   4620
taacctttttt tcatgccatg tcttaagagt tataatgtac actcgatgat tgccaagaga  4680
gggggagggg gaggaaaaca gccaacagca gagctggttg gtctgaactc agtgcagttt   4740
tcaatgagaa caacagctgt ccagcaagga atcatatcat ccattctcag cttctacatt   4800
caaagggcag agctttttag aaaactcaac ctcctaaggc attaggaatt gagctgaaac   4860
cagcagaatt gaaaactctg gcaataaaat atagactcaa tcgtaaccct tctggcaagt   4920
tccttctcag agaaggaagt gggagtaaaa tgtggccttc cccacttctt tacatcaccc   4980
ctgtcacaat gtccccgctg gcctggccag tttcgagagg gaagggtgga ctggttttag   5040
tactctgaag aaaacccaag ctgcagtatt tgaggtgcag tataatattt cctaatcttt   5100
cctatttctt aacaaaaaaa gattttaaag tacttctcta ctcattgaat ttttgttctt   5160
tacatactat tgatatattc ttttttctact caaaagtgcc aaaggctaca gttttaatg   5220
acttaacaaa ttgtaccaca ttgttaagga aatataatga tagacactag aattcagacc   5280
tctgcatgta tatttgataa cacatctttt gtaaaaaata aataattaca aaaaatttgt   5340
ttacattcca caggtaccttt aatttaaaat aaatcagact aacaggtggt atctcttctt   5400
agtgttctat ttatcttatt tgctaatgag aacaattctt cttctgttag gctgtgcttt   5460
attgataaaa ccaagtattg aataaaggga gttaattatc tttttaaagt aaatgaaatt   5520
ataaatatat aatatatata aagtattgtg tttaataaaa tgttatgcaa tgttttccaa   5580
actgataaag tttgtaaagt gctataaatg tatttttgtta agtacagatc aaagctatcg   5640
tgtgagtata ttgtgctaac atcatagaaa taaagattag atttcttcat caaaaaaaaa   5700
aaaaaaaa                                                            5708
```

<210> SEQ ID NO 18
<211> LENGTH: 2783
<212> TYPE: DNA

<213> ORGANISM: Mus musculus

<400> SEQUENCE: 18

```
ggcgcggggc gcgggatctc gccttcccca cactgcgccg cgcgctccta ggtcccggag      60
atcaaccgtg ctcgcgcaag gcgcacagaa ggcacgcgca aggggcaggg acgagaccca     120
gattgcggtc cccgcgcagg gccagagacc ctgagacccg cagagtggga ggcggaggcg     180
cccaagccgg gggcggggtt ggggcgggggc cgagcgggct gcagagcgcg cagacaaaga     240
gctcacgcgc cgcacaccgc gcccgggcct cgcgtccctc ccacgcgggg accctggctt     300
tgtgtccgcg ctttgcaagg gactccgccc tccttgctcc ctccaggtga acgagccgcg     360
tgcgcgcgcg ggggctccgg cctctccctt ccccaagttc ccctctgct ccagcctcag     420
tttccccgag ccctcttggc taaccccttat ctccccacct ggagactcca tctgcgcagc     480
tcctagtctc cagcctgcct ttgtccccct gcaatctcgg cctacagcgc caacgtcacc     540
atgcttgcta tgaaggagaa gaataaaacg ccgaaggaca gcatgacact cctgccttgc     600
ttttatttcg tggagctacc catcgtggct tcctccattg tgtctctgta cttcctggag     660
ctgactgacc tgttcaagcc ggccaaggtg ggctttcagt gctacgaccg cgccctgtcc     720
atgccctatg tggagacaaa tgaagagctg atcccattgc tcatgctgct gagcctggcc     780
ttcgctgcac ctgcggcctc aatcatggtc ggcgagggca tggtctactg tctgcagtcc     840
aggctctggg gccgtggtcc aggggggcgtg gagggcagca tcaacgctgg tggctgcaac     900
ttcaactcct tcctccggcg cacagtgcgc tttgtgggtg tacacgtgtt tggcctgtgt     960
gccacggctc tggtgacaga tgtcatccag ctggccaccg gctaccacac acctttcttc    1020
ttaacggtct gcaaacccaa ttacaccctg ctgggcactt cctgtgagtc gaacccttac    1080
atcacacagg acatctgctc tggccacgat acccatgcca tcctgtcagc aaggaagacc    1140
ttcccgtccc agcacgccac tctgtcagcc tttgctgctg tctacgtgtc gatgtacttc    1200
aacgcggtta tctcggacac cacgaagctg ctgaagccca tccttgtgtt tgccttcgcc    1260
attgctgcgg gcgtctgcgg cctcacacag atcacccagt atcgaagcca ccctgtggac    1320
gtctacgctg gctttcttat cggtgctggc atcgctgcct acctggcctg ccacgctgtg    1380
ggcaacttcc aggcaccacc tgcagaaaag gttcctaccc cagctcctgc caaggacgcc    1440
ctgcgagcgc tgacacagcg gggccatgag tccatgtatc agcagaataa gtctgtcagt    1500
accgatgagc tgggccctcc agggaggcta gagggcgtgc ctcggcctgt ggctcgagag    1560
aagacatctc ttggcagctt gaagcgagcc agcgtggatg tggacctgct ggccccacgt    1620
agccccatgg gcaaagaagg catggtcacc ttcagcaaca cactgccccg ggtcagcacg    1680
ccctcgctgg atgaccctgc acggcgccac atgactatca acgtgcccct tgatgcctcc    1740
cgttccaggc agcttatcgg tgagtggaag caaaaatccc tggagggacg tggcctgggt    1800
ctgcctgatg aagccagccc tgtgcatctg agggccccag cagagcaggt agcagaggag    1860
gaagaggaag aggaggagga ggaggaagaa gaggaggaag aggaggaaga ggaagggcct    1920
gttccaccct cactctaccc tactgtccag gctcggccag gccttgggcc ccgagtcatc    1980
ctgcctccaa ggccagggcc ccagcccctc gtacacatcc ctgaggaagg cgttcaggct    2040
ggagctggcc tgtcacccaa gagcagcagc tcatcagtga gggccaagtg gctgtcagtg    2100
gctgagaagg gtgggggccc agtggctgtg gctccatccc agccccgggt ggccaaccca    2160
cccaggctac tacaggtcat cgctatgtcc aaggcggcag ggggcccaa ggctgagaca    2220
gcttcgtcct ccagtgccag ctccgactct tcccagtaca ggtccccgtc agaccgtgac    2280
```

| | |
|---|---|
| tctgccagca ttgttacaat cgatgcccat gcacctcacc atccagtggt gcacctgtct | 2340 |
| gctggcagca caccctggga gtggaaggct aaagtagtgg agggtgaggg tagctatgag | 2400 |
| ctgggggacc tggcacgcgg cttcagaagc agctgtaaac agcctggaat gggcccgggg | 2460 |
| tctccagtca gtgatgtgga ccaggaagaa ccccggtttg gggcagtggc cactgtcaac | 2520 |
| ctggccactg ggagggtct gcccccacca ggtgcaagtg aaggggccct aggtgcaggc | 2580 |
| agcagagaat ccaccctaag gcgccaggtg ggcgggctgg cagagagaga agtggaggct | 2640 |
| gaggcagaaa gttattatag gaggatgcag gccaggaggt accaggacta agcctggcaa | 2700 |
| aactgtgatg gggattaggg gagctggggg tgtctacagc cccaccaata aaaacttatg | 2760 |
| ctattaaaaa aaaaaaaaaa aaa | 2783 |

<210> SEQ ID NO 19
<211> LENGTH: 3764
<212> TYPE: DNA
<213> ORGANISM: Mus musculus

<400> SEQUENCE: 19

| | |
|---|---|
| gatacgcccg tgccgcgcgc tcgcccgctc gctctcccac gcaagcggaa tgcagcagcg | 60 |
| cctgaggagc tcgtctgcag ccgctgcctg aatgcacctc gccgcctgca gtccgtccgc | 120 |
| ccaatagggc gcaaggaagg aagcttggcc gccaaagcct ggacagtttc tgacagtgca | 180 |
| gtctcaccac atgatttgag aaatggctgt agaaaacaac actcaacgca gttactccat | 240 |
| cattccatgt tttatatttg ttgagcttgt catcatggct gggaccgtgc tgcttgccta | 300 |
| ctacttcgaa tgcactgaca cctttcaggt gcatatccaa ggattcttct gtcaggacgg | 360 |
| agacttaatg aagccttacc cggggacaga ggaggaaagt ttcatcagcc ctctggtgct | 420 |
| ctactgcgtt ctggctgcca ctccaactgc tattattttc attggtgaaa tatccatgta | 480 |
| tttcataaag tcaacaaggg agtccctgat tgctgaggag aaaatgatcc tgacagggga | 540 |
| ctgctgctac ctgagcccct actccgaag gatcatcagg ttcatcgggg tatttgcatt | 600 |
| tggactttt gctactgaca tttttgtaaa cgcggggcaa gtcgtcactg gtcacctaac | 660 |
| accatacttc ctgacagtgt gccagccaaa ctataccagt acagactgcc gggcacacca | 720 |
| acagttcatc aacaatggca acatctgcac tggggacctg gaagtgatag aaaaagctcg | 780 |
| gaggtccttt ccctccaaac atgctgctct gagcatttac tccgccttat atgccacgat | 840 |
| gtacatcaca agcacaatca agacgaagag cagtcggctg gccaagccag tgctgtgctt | 900 |
| ggggaccctc tgtaccgcct tcctgacagg cctcaaccgc gtctcagagt accggaacca | 960 |
| ctgttccgac gtgatcgccg gcttcatcct gggcaccgca gtggccctgt ttttgggaat | 1020 |
| gtgtgtggtt cataacttca gaggaaccca aggctctcct tccaaaccca aacccgagga | 1080 |
| tccccgcgga gttcccctga tggctttccc aaggatagag agcccgctgg aaaccttaag | 1140 |
| tgcacagaat cactccgcct ccatgaccga agtcacctga gatgaatgaa gacatgcagc | 1200 |
| tgtttaggga ttgtttggtt tttgtttgt tttttttcca gcaaccttcc agttcaattc | 1260 |
| ttcaaaacac acagatactc aagtcaaact gtgaagacaa gtattacatt tgtctagtta | 1320 |
| gaggctaatg ttttgtacat ttttgtatg aagaagtgat gtagcttgcc ctgatctttt | 1380 |
| tttgtcagct ttaatatatt tatgccagat ttttaaaacc aacaaaattt tcctgttgtt | 1440 |
| caagtgtgca ttgaagaatc acatttatcc aatggttgac gttgttttgt gatatttgta | 1500 |
| cacaaatttt tctcagttttt atagacacaa ataaagcaaa caacccactt taaccctta | 1560 |

-continued

```
ttaccacagt tgctgcctcc tccagaagtt ttgaatttta atggaagtta aacttttgag    1620
ttacaggaag gaccgtggtg gttaattgta aatctcaaag tcaatcgtgg aaaaaaaaat    1680
attggaagag aacattgtgt tctgctttgt aaatagttga ctgcattccc agttaaagca    1740 acagggcat actagtgaag agttctagtt gcccaactat tggcacagaa gcctatattt     1800
ggaggaagag tactttggtt atatgatgct ttcttagata atggcctcgc catcctacag    1860
agcacaaggt cagtctggga ttctgacctt gggcaggtga caccgtggcc tactatccaa    1920
gagagcagca agcaccagcc tttcctgtca actcaacagt tttgtatatc atattgtatg    1980 gacttttat gaaaagaat attttacagt ttgcacagta ttattttaca gaaaggctat      2040
cagagcatct acatgtagag cccagagcaa cggcttcact atggggcttt taactgttct    2100 tagatttta ctgcatccca tttttctag catggtgata atgtgtccct cctttgggag      2160
aaggagttcc ctttctgtat ctatcaaaat gtttctcacc cttgtcaggt cttcttagct    2220 tttttgtac atatttttt ttctaaagag aagaaaaaaa aagttatcac aaaatgtagt      2280
ctggctcctg tgctctgtgt ttcatttcag ttggcggtgt ttgaagaact gtggagtgtc    2340
tgtgcttctc agtccatgag agaggggatt agatgaacca ttaaacaggg gcatgctgaa    2400
aggtcattca gagtaagcag acagaagcag ggggcgaagg aatgactgta cacaaatagg    2460
catacatatg tgttaaaata aggtgaaaga attccttcat ttattaagat actcaaatca    2520
aatgcatttt ctggattctt agtgtgatgc catagtcttc aacctgttct gaaatttcca    2580
agttttcagt aaacaattag tcttttttt ttttttagga acaaaagtca cctctgataa     2640
aactttcctg ggagtttcct gaactgtact catacacatg ttctaagtag tatctgacta    2700
aagtcagaga aaagagctgt taaggctctg ttcatcacaa gtgttaacca cctgccctca    2760
catatataat gcatctgttg ttttcagggc aatgaaccca gggagggata taaactctaa    2820
aacactgtga catacactag ttccaacatc ttggtcgagc tctgccccat tcttatttct    2880
atttctgtta catgatgcct ctgaatcaag tttagcccct cttggtgtga tgtgtctact    2940
gagatggttc atggatgcta cagacaaaag gaagtcccag gaaagaatga tttgtagact    3000
ctgagctctg tcttctgtcc tgtatgctaa gtgtgaagtc atccagtgtc tgggcgacac    3060
atttatttta cttaaacaca tggtattttt aaagaaaatt agtaatgggc tctctttagt    3120
ttacttttcc taaaacatca gaaatgaggg tagacaaaat tgatgtttat tacctacttc    3180
atgtcacacg tagttatcag cttttcttgt caccaaattg tattttgaag aaaaatcaag    3240
tcaacaacac ggatcactac ctttgaactc ctcttttcta ggtttgattc tgggaagatc    3300
acttgttact tcaaaatctg tggtcacaga ctctgcttcc atagcccagg gtgtataggg    3360
tattctctgg caagctatgc tctatatcag ttacaactga gggatttctt tctgttctgt    3420
tccctggatc tctgagttag tctaccctct gcattatgcc actttaataa agcctctgcg    3480
tacccttaag atattcagtg gcctcaggtt gagggtaaac cttccaatct agcatgtgag    3540
attcattcct caggtttgga tgtccctact tggttttttct gacaaagaca aagcttttg    3600 ttcaaacagg acaaataatg actataacct aagagaaata aattctggag tgaatgctgt    3660
tcctcttttt tagtggattg cagaaatgcc tgagaaagtc tggcttgctg tggaaaggga    3720
ttggaaagga acaagacgaa taaagtgttt tgattttatg ccgc                     3764
```

<210> SEQ ID NO 20
<211> LENGTH: 2699
<212> TYPE: DNA
<213> ORGANISM: Mus musculus

<400> SEQUENCE: 20

```
gtgtagtgtt tgggatggag gccacgcctg ggttatatct tatgtgggag tgcccatatg      60
ggtgactctg cacacctgga atctggtgac cctctctcca atatgtcatt ctgtggagta     120
ggcctcaatg gagccctgga tgcacagtac ccaccttcat ctgcctgggc ctcagtttcc     180
acatccgtgc aatggagatg aatgttcttg ccttgctggc ctcacggagt ggctgtgagt     240
tggtggcagt ggaggtggat gcctggaaga agccctaggg ctctttcaca ggccccagct     300
tcgccatggc tggagggaga cctcacctga agcggagttt ctctatcatc ccttgcttcg     360
tctttgtgga gtctgtgttg ctaggcatcg tggtccttct tgcgtaccgc ctggagttca     420
cggacacctt ccctgtgcac acccagggct tcttctgcta tgacagcgct tatgccaagc     480
cgtatcccgg gcctgaggct gccagccgag cgcccctgc cctcatctat gccttggtca     540
ctgctgggcc caccctcacg atcctgctgg gggagctggc ccgtgccttc ttccctgcgc     600
caccctcctc cagtcctgtc agtggggaga gcaccatcgt gtccggggcc tgctgccgct     660
tcagtccccc actgaggagg ctggtccgtt cctgggggt gtactctttt ggcctcttca     720
ccacgaccat ttttgcaaat gcgggacaag tggtgaccgg taaccccaca cctcacttcc     780
tgtcggtgtg tcgccccaac tacacggccc tgggctgccc accaccgtct cctgaccggc     840
cagggcctga ccgcttcgtc acggaccaga gcgcctgtgc aggcagtccc agcttggtgg     900
ccgccgcacg ccgcgccttt ccctgcaagg atgcggccct gtgcgcctac gctgtcacct     960
atactgcgat gtacgtgacc ctagtgttcc gcgtgaaggg ctctcgcctg gtgaaacctt    1020
ccctctgcct ggccctgctg tgccccgcct tcctggtggg cgtggtccgc gtggcggagt    1080
atcgcaacca ttggtcggac gtgctggctg gctttctgac gggagcagcc atcgccacct    1140
ttttggtcac ctgtgttgtg cacaatttcc agagccgacc ccactctggt cgaaggctct    1200
cccctggga ggacctgagc caggccccca ccatggacag cccctcgaa aagaacccga    1260
gacctgcagg ccgcattcga caccggcacg gctcacccca tccaagccgc agaactgtgc    1320
ccgccgtggc cacctgattc ccagctgtgt gtcctccagg gcgccagcta tgtgctcctc    1380
gccccgtgtg cccgcccctc gactgaggtc tgagccaaca cccctgcctc tgccgctgcc    1440
tcttcctgca ccgactccca gtcagggtcc ctcgccttcc tccctggac ccggggccc     1500
aggcggggga ggtgggcggg gccggaagct gctgctgccc acgcccctgc taagggacct    1560
gtacaccctc agtggactcc atccctcccc tttccaccgc gacaacttca gcccttatct    1620
gtttgccagc cgcgaccacc tgctgtgaga tccaccacct agaatctacc cagtgaccgt    1680
ttcccccctg ccacgcgtgt gtgtggcatg tgagtgctaa aggcccctgc cctccaaacc    1740
agccaggccc acccagcgtc agaagatggc tggaagggac gcttcaaggc agggaatctc    1800
ttggctgctc tttggccttt tgggatatct gggtaggcaa aaataaccag gtgggcccat    1860
gtccccagga tttcccttttt aacggctgat gcttgaccta attgaccatt gcctagccag    1920
tgagagctct gagttatcag aattcaaccc aaaagtttac aaaagtttat gggaaccctct    1980
cacttcttag cttcctcaag caggagggtg ctactgtggc cggtgttcaa gtgtctaaac    2040
agccaataag agcccttggc gttcagaatt gcagagagtg ggtgggaatg attccagtca    2100
atgggggacc gcccgtgtca aagccaagtc aaagccaagg agggctatcc agctctcctc    2160
gggaacacgg aatccagctg gagagggggg gggcaggctc ccccacagca gagtcctgcg    2220
gcaccccttc ccttctagac cttcccccag gtgcaccatc tcacaccctc caactcccta    2280
```

-continued

```
cttaagtagg gcttgcccca gttcacaggt tttagaattc tggacgctgt ctcccttggc    2340
tgtgcctagg gcacctcccc ccactccccg ccaaaccttc tattattact agggctgtgg    2400
aaaatgactt tattttctcg ggacccaccc ttcttcttca cactgccccc atgcctcagt    2460
ctcatgcagt tgtgccatct tgggggcat ggtggagca aaggggtt ccctaccct    2520 gaatagccaa aggcagtggg cagatgagac actgtccccc tttcctgccc cctcctcat    2580 cttaataaa gacctgtttg taacagaaaa aaaaaaaaa aaaaaaaaa aaaaaaaaa    2640 aaaaaaaaa aaaaaaaaa aaaaaaaaa aaaaaaaaa aaaaaaaaa aaaaaaaa    2699
```

<210> SEQ ID NO 21
<211> LENGTH: 5372
<212> TYPE: DNA
<213> ORGANISM: Rattus norvegicus
<220> FEATURE:
<221> NAME/KEY: misc_feature
<222> LOCATION: (1137)..(1137)
<223> OTHER INFORMATION: n is a, c, g, or t
<220> FEATURE:
<221> NAME/KEY: misc_feature
<222> LOCATION: (2899)..(2899)
<223> OTHER INFORMATION: n is a, c, g, or t
<220> FEATURE:
<221> NAME/KEY: misc_feature
<222> LOCATION: (2917)..(2919)
<223> OTHER INFORMATION: n is a, c, g, or t
<220> FEATURE:
<221> NAME/KEY: misc_feature
<222> LOCATION: (2921)..(2924)
<223> OTHER INFORMATION: n is a, c, g, or t
<220> FEATURE:
<221> NAME/KEY: misc_feature
<222> LOCATION: (2929)..(2929)
<223> OTHER INFORMATION: n is a, c, g, or t

<400> SEQUENCE: 21

```
atgccccaat tcaccctctc tcttcagatg caggcaaaaa attctcactt tgttcctcgg      60
cggattggag ctttttctag gtgcttccct tggagttacc tccctagaga tcagaaggtc     120
agggctgtca cgcttgggta gcggccagct cccagtgaat tccttctatg gcctacttgt     180
cagtatgaaa tctgagtttt aattttgcac aggtggaggt ctcttttgct atgggtaagg     240
tggatagcgg tgcccagcaa gctcctgctc tctagaaagg caacaagaac cccaggtagg     300
agaccaggtg ccttggctcc tcagccttgc ttctgcagaa accaggagtg cctcccccca     360 ctattttga cgtcaagctc agacaaccag cagaggagcc tcacagcttg gcggtggag      420 agcccaggga gagtggcagg gaggggaagc catcacagca acagcttgga gggggagctg     480
gctatcactt tccctcaaaa tacggactaa aacccggctg aagaagacct gcgggatcag     540
ggaagcgccg ggttactgca aagaagggcg gggaaaagga gggggcgctg catgcagcgc     600
gctggctcca gcggtgcccg cggggaatgt gacatcagcg gcaccgggcg cttgcggctg     660
gagcaggcag ctcgcctcgg tggccgcgca gtgcacacct cacccacggg aggactcgga     720
gcccggcagg tggccgggat gtcggcgaag gagaggccaa agggcaaagt gatcaaggac     780
agcgtcaccc tcctgccctg tttctatttc gttgagttgc ctatattggc gtcatcggtg     840
gttagtctct acttcctgga actcacagat gtcttcaaac ctgtgcactc cggattcagt     900
tgctatgaca ggagtcttag catgccgtac attgagccaa cccaagaggc cattccattc     960
ctcatgttgc ttagcttggc ttttgctgga cctgcaatta cgatcatggt gggtgaaggg    1020
attctgtact gctgcctctc taaagaagaa aatggagctg gattggagcc caacatcaac    1080
gccgggggct gcaacttcaa ttcctttctc agaagagccg tcagatttgt tggtgtncac    1140
```

```
gtggttggac tgtgctccac agctctcatt acggatatca tacagcttgc cacaggatat   1200
caggcaccat actttctgac tgtgtgcaag ccaatgtaca cctccctgga aggatcctgc   1260
aaggaaaatt cctacatcgt ggaagaaatt tgttcgggat ctgacctaac agtcatcaac   1320
aatggcaaaa agtcattccc gtcccagcat gcgaccctcg ctgcctttgc tgctgtgtat   1380
gtgtccatgt acttcaattc cacattaact gactcctcca agctcctgaa acctctcttg   1440
gtcttcacat ttatcatctg tggaatcatc tgcgggctaa cacggatcac tcagtataag   1500
aaccatcccg tcgatgttta ttgtggcttt ttaattggag gaggaatcgc gctgtatttg   1560
ggcctgtatg ctgtagggaa ttttctgcct agtgaagaca gcatgcttca gcacagagat   1620
gccctcaggt cactgacaga cctcaatcaa gaccccagca gggttttgtc agctaaaaat   1680
ggtagcagcg gtgatggaat tgctcacaca gagggtattc tcaaccgaaa tcacagggat   1740
gcaagctcct taacaaatct gaagagggcc aacgctgacg tagagatcat cactcctagg   1800
agccccatgg ggaaggagag catggtgacc ttcagtaaca cgctgcccag ggccaacacc   1860
ccgtccgtgg aagacccggt gagaagaaac gcgagcattc acgcctctat ggattctgcc   1920
cggtccaagc agctccttac ccagtggaag agcaagaacg agagtcgcaa gatgtccctg   1980
caggttatgg actctgaacc agaagggcag tcaccaccca ggtccataga aatgaggtcc   2040
agctcagagc cctcgagggt gggggtgaat ggagatcacc atgtcccggg caatcagtac   2100
ctcaagatcc agcctggcac agttcccggg tgcaacaata gtatgcctgc agggccacgt   2160
gtgtccatcc agtcccgccc tggctcttcc caattggtgc acatcccga ggagacccag   2220 gaaaacataa gcacctcgcc caagagcagt tccgcacggg ccaagtggct gaaagcagca   2280
gagaagaccg tggcctgtaa ccggggcaac aaccagccac gcatcatgca ggtcatcgcc   2340
atgtccaagc agcagggcgt gctgcagagc agccccaaga atgccgaagg tagcacggtc   2400
acctgcacag gctccatccg ctacaaaacc ctgactgacc acgagccgag tggcattgtg   2460
cgagtggagg ctcatcccga gaacaacagg cccatcatcc agattccatc gtccaccgag   2520
ggcgaaggca gtggctcctg gaagtggaaa gctccggaga gagtagcct cgccaaacc    2580 tatgagctca acgacctcaa cagggactcg gaaagctgcg agtccctcaa agacagcttt   2640
ggttctggag atcgcaagag aaagcacatc gacagcaatg agcaccacca ccacggcatc   2700
acaaccatcc gcgtgacccc agtggagggc agcgagatag gctcagagac gctgtctgta   2760
tcctcctcac gcgactccac cctgcgcagg aagggcaaca ttatcttgat ccctgaaaga   2820
agcaacagcc ctgaaaacac aagaaacatc ttctacaaag gaacctcccc cacgaggcct   2880
tataaggatt gaatccccnc ccttctgcct catcatnnng nnnncatcnc ccacccccc    2940 accccagcca cacatttatt atagtacctt gtgctctttt gggtattttg ttgttgtttt   3000
ggttttggtt ttttgttttc tttttctagtg atatggaga gccttcttgc ccaactagat   3060
tgttcaccat cagcctggaa ctctcactga cccaccacag aaaccgtggt gattttccac   3120
caagggaaag gaaagcaca agcaagacc cgaactaatc tcatcatctg aatagttctt     3180
aaggcctgtc actgagactt cgcagagggc agtattagga taaagtggtc tcctccgatg   3240
tatagtattt aacttctga atgtgccaac tttgaagttt cttttttttt ttttttcatta   3300 taattagcgg tgggaaccca aaacactaca ggtttccccg gcagcagagg ccacgcgta    3360 ttatatagta tttattttg cagactctgc accagaagag cagactgggc ggtgctgatt   3420
accacagtac atctaccatt tcaactctca gactctgtgt agctgtgaga gagtggtgta   3480
```

```
caaccccctt gtcagagaaa tgctacttca ttcagaagac gccagtgact ttgtggtagc    3540
ataggccatt cttggcttcc ctgtagtggc tctctcacag tcaaaaagaa aaagaaaga    3600 aaaaactgga cagggttctg agcatttctt tgaaagattc tttgttttca acatttgaaa    3660
gtctgtaggg atgttttcgg tgagacggaa caactagttc tccgcatcgt ttttctgctt    3720
tttatttaag tattggtaat gctggtttct ggtatctttt ttttttagtg agtgcatttg    3780
catatttaaa atacattgtt ttagagaata ttttgaaatt attataatca cattttccat    3840
tttgtggctt catcttagtt tattaagttt tttgaggtta tgcacaccat tcttctattt    3900
taagaaagca acagtgacca tttacattcc ttgtgcaaaa tacactgctt cgaggtccta    3960
cgcaagaaat atgagccaac ggttgaaact gtgcgttcca ttgccagata cattggtcac    4020
attcaagatg tctccaatcc gatggcatag gttatcacat cagtaagcga tccccaaact    4080 tcatttttctt ccagagcatt tcatttttgt gttatcctga taatcaccat atcggagcca    4140
ccatgggggt gagcttgact cccttccctg acacactttt aactggacac caacagtaag    4200
gacctaggca aaggctaatt gatagataga agtgtatcac agcatacatt tagaaagtgt    4260
atcttcaaaa cagcagacca ggcaaagctt ttgtgcttag agtactattg acagttttgg    4320
ctgcctgtct tgaatctaga accttgagcc aaaatcaaag gaaaccatac tgttgatagc    4380
aagaagatta ccacaagata tttttgaagt gttttcccag gttagatgtt taaagagtgg    4440
agacatatat ttggtccttg aaatttgtta taaaaccttt ctcatgccat gtcttaagaa    4500
ttataatgga cacttgatga ttgccaagag ggggagcaaa acagcgaac agcagagctg    4560 gttggtctga actcagtgca gctttcagtg agaacaaaag ctgtccagca aagagtcaca    4620
tcattcattc tctagcctct ccattcaaag ggcagagctt ttttttttttt ttaagaaaac    4680 tcaacctctt aaggcattag gaatttagct gagaccagca gaattgaaaa ctctggcagt    4740
aaaatatagg ctcaaccata acccttctgg aaagttcctt tttttttttt ttttcctttt    4800 ttttatttttt ttttttttttt ttgtgatcga gttgactgca gtagttcatc atattctttt    4860
tctactcaaa gtgccaaagg ctacagtttt taaacgactt aacaaattgt accacactgt    4920
taaggaacta taacgataga cactagaatt cagacctctg catgtatatt tgataacaca    4980
tcttttgtaa aaaataaata attacaaaaa atttgtttac attccactgg taccttaatt    5040
taaaagaaat cagactaaca ggtggtatct cttcttagtg ttctatttat cttacttgct    5100
aacgagagca attcttcttt tgttaggctg tgctttattg atgaaaccga gtattgaata    5160
aagagagtta attatctttt taaagtaaat aaaaactatga atatataata tatatgaagt    5220
atcgtgttta ataaaaatgt tatgcaatgt tttccaaact gataaagttt gtaaagtgct    5280
ataaatgtat tttgttaagt acagatcaaa gctatcgtgt gagtatattg tgctggcatc    5340
atagaaataa agattagatt tcttcatcaa aa                                 5372
```

<210> SEQ ID NO 22
<211> LENGTH: 2597
<212> TYPE: DNA
<213> ORGANISM: Rattus norvegicus

<400> SEQUENCE: 22

```
gaccaaagca tgttcataag ttctgggaac tgttcataca taaaagtagc cttggcaatc      60
tctcccatga gctgcccaga aggtccccaa ggatcatcat tcgttgcttc tcgaactttg     120
gactcgatct ctgaataatt cataaccaca ttggtggctt tgtccatcag tcccgcacct     180
cccttcccca gtttcccccc ttctgctcca gcctcagttt ccccgagcct tctgaccagg     240
```

```
agccagggct agcccttatc tccccacctg gagactccat ctgcgcacca actagtctcc    300
agcctgcctt tgtccccctg caacctcggc ctacagcgcc agcgtcacca tgattgctaa    360
gaaggagaag aataaaacgc cgaaggacag catgacgctc ctaccttgct tttatttcgt    420
ggagctaccc atcgtggctt cctctgttgt gtctctgtac ttcctggagc tgactgacct    480
gttccagccg gctaaggtgg gctttcagtg ccacgaccgc tccctgtcca tgccctacgt    540
ggagacaaat gaagaactga ttccactgct catgttgctg agcctggcct ttgctgcacc    600
cgcggcctcc atcatggtcg gcgagggcat ggtctactgt ctgcagtcca ggctctgggg    660
ccgaggtcca gggggtgtag agggcagcat caatgctggt ggctgcaact tcaactcctt    720
cctccggcgc acagtgcgct tgtgggtgt acacgtgttt ggcctgtgtg ccacggctct    780
ggtgacagat gtcatccagc tggcaaccgg ctaccacaca cctttcttcc taaccgtctg    840
caaacccaat tacaccctgc tgggcacttc ctgtgaggcg aacccttaca tcacacagga    900
catctgctct ggccatgata tcatgccat cctgtcagca cggaagacct tcccatccca    960
gcacgccact ctgtccgcct cgctgctgt ctacgtttcg atgtacttca actccgttat   1020
ctcggacgcc acaaagctgc tgaaacccat ccttgtgttc gccttcgcca ttgccgctgg   1080
cgtctgtggc ctcacacaga tcacccagta ccgcagtcac cctgtggacg tctacgccgg   1140
cttccttatt ggtgctggca ttgctgccta cctggcctgc cacgcggtgg caacttcca   1200
ggcgccacct gcagaaaagg tgcccacccc agctcctgcc aaggacgccc ttcgagtgct   1260
gacacagcgg ggccatgagt ccatgtatca gcagaataag tctgtcagca cagatgagct   1320
gggccctccg gggaggttag agggtgtgcc tcggcctgtg gctagagaga agacatctct   1380
tggcagcctg aagcgagcca gcgtggatgt agacctgctg gccccacgca gccccatggg   1440
caaagagggc atggtcacct tcagcaacac actgccccgg gtcagcacgc cctcgctgga   1500
tgacccttcc cggcgacaca tgactatcca cgtgcccctt gatgcctcgc gctccaggca   1560
gctgatcagt gagtggaagc aaaagtctct ggagggtcgt ggcctggggc tgcctgatga   1620
ggctagccct gcgcatctgc gggccccagc agagcaggtg gcagaggaag aagaggaaga   1680
ggaggaggag gaagaggagg aagaagagga agaggaggag gaggaagggc ctgttccacc   1740
ctcgctctac cccactgtcc aggctcggcc agggctcggg ccccgagtca tcctgcctcc   1800
aaggcctggg ccccagcccc tcatccacat ccctgaggaa gtagttcagg ctggagctgg   1860
cctgtcaccc aagagcagtg catcagtgcg ggccaagtgg ctgtcaatgg tggagaaggg   1920
tgggggccca gtggctgtgg ctccaccaca gccacgggtg gccaacccac cgaggctact   1980
acaggtcatt gccatgtcca aggcagcagg ggccccaag gctgagacag cttcctcctc   2040
cagtgccagc tccgactctt cccagtacag gtccccatca gaccgggact ctgccagcat   2100
cgtcacaatt gatgcacatg caccccacca cccgtggtg cacctgtctg cgggcagcac   2160
accctgggag tggaaggcca agtggtgga gggggaaggt ggctatgagc tgggggacct   2220
ggcgcgtggg ttcagaagca gctgcaaaca gcctggaatt ggcccagggt ctccagtcag   2280
tgatgtggac caggaggaac cccggtttgg ggctgtggcc accgtcaacc tggccactgg   2340
ggagggtctg cccccaccag gtgcaagtga aggggccctg ggtgcaggca cagggaatc    2400
caccctgaga cgccaggtgg gggcgctggg ggagagagaa gtggaggcag aggcagaaag   2460
ctactacaga aggatgcagg ccaggaggta ccaggactaa gcctggcaaa gctgtgatgg   2520
gcagaaggca ggctgggggg tcactacagc cccaccaata aaggttcatg gtaaccgtaa   2580
```

```
aaaaaaaaaa aaaaaaa                                                     2597
```

<210> SEQ ID NO 23
<211> LENGTH: 1040
<212> TYPE: DNA
<213> ORGANISM: Rattus norvegicus

<400> SEQUENCE: 23

```
agcttggccg ccaaagcctg gattatttct gtcagtgcag tctcaccaca tggtttgaga      60
aatggctgta gagaacaaca cccaacgcag ttactccatc atcccatgtt ttatatttgt     120
tgagcttgtc atcatggctg ggacagtgct gcttgcctac tacttcgaat gcactgacac     180
ctttcaggtg catatccaag gattcttctg tcaggatgga gacttaatga agccttaccc     240
ggggacagag gaggaaagct tcatcagccc tctggtgctc tactgtgttc tggctgccac     300
cccaactgct attattttca ttggtgaaat atctatgtat ttcataaagt caacaaggga     360
gtccctgatt gctgaggaga aaatgatcct gacggggac tgctgctacc tgagccctt      420
actccgaagg atcgtcaggt tcattggggt atttgcattt ggacttttg ctactgacat      480
ttttgtaaac gccgggcaag tagtcactgg tcacctaaca ccgtacttcc tgacagtgtg     540
ccagccaaac tataccagta cagactgccg ggcacaccac cagttcatca acaatggcaa     600
catctgcact ggggacctgg aagtgataga aaagctcgg aggtcctttc cttccaaaca      660
cgctgctctg agtatttact ccgccttata tgccacgatg tacatcacaa gcacaatcaa     720
gacaaagagc agtcggctgg ccaagccagt gctgtgcttg ggggacctct gtacagcctt     780
cctgacaggc ctcaatcggg tctcagagta ccggaaccac tgttcagacg tgattgccgg     840
cttcatcctg gcaccgcag tagccctgtt tttgggcatg tgtgtggttc ataactttaa      900
aggaactcaa ggctctgctt ccaaacccaa acctgaggat ccccgtggag ttcctctgat     960
ggctttccca aggatagaga gcccgctgga aaccttaagt gcacagaatc actcagcctc    1020
catgaccgaa gtcaccctgag                                                1040
```

<210> SEQ ID NO 24
<211> LENGTH: 1501
<212> TYPE: DNA
<213> ORGANISM: Rattus norvegicus

<400> SEQUENCE: 24

```
gtgtagtgtt tgggatggag gccacgcctg ggttatatct tatgtgggag tgcccatatg      60
ggtgactctg cacacctgga atctggtgac cctctctcca atatgtcatt ctgtggagta     120
ggcctcaatg gagccctgga tgcacagtac ccaccttcat ctgcctgggc ctcagtttcc     180
acatccgtgc aatggagatg aatgttcttg ccttgctggc ctcacggagt ggctgtgagt     240
tggtggcagt ggaggtggat gcctggaaga agcccctaggg ctctttcaca ggccccagct    300
tcgccatggc tggagggaga cctcacctga agcggagttt ctctatcatc ccttgcttcg     360
tcttttgtgga gtctgtgttg ctaggcatcg tggtccttct tgcgtaccgc ctggagttca    420
cggacacctt ccctgtgcac acccaggct tcttctgcta tgacagcgct tatgccaagc     480
cgtatcccgg gcctgaggct gccagccgag cgcccctgc cctcatctat gccttggtca     540
ctgctgggcc caccctcacg atcctgctgg gggagctggc ccgtgccttc ttccctgcgc     600
caccctcctc cagtcctgtc agtggggaga gcaccatcgt gtccggggcc tgctgccgct     660
tcagtccccc actgaggagg ctggtccgtt tcctgggggt gtactctttt ggcctcttca    720
ccacgaccat tttgcaaat gcgggacaag tggtgaccgg taacccccaca cctcacttcc     780
```

-continued

```
tgtcggtgtg tcgccccaac tacacggccc tgggctgccc accaccgtct cctgaccggc    840
cagggcctga ccgcttcgtc acggaccaga gcgcctgtgc aggcagtccc agcttggtgg    900
ccgccgcacg ccgcgccttt ccctgcaagg atgcggccct gtgcgcctac gctgtcacct    960
atactgcgat gtacgtgacc ctagtgttcc gcgtgaaggg ctctcgcctg gtgaaacctt   1020
ccctctgcct ggccctgctg tgccccgcct tcctggtggg cgtggtccgc gtggcggagt   1080
atcgcaacca ttggtcggac gtgctggctg gctttctgac gggagcagcc atcgccacct   1140
ttttggtcac ctgtgttgtg cacaatttcc agagccgacc ccactctggt cgaaggctct   1200 cccctgga ggacctgagc caggccccca ccatggacag ccccctcgaa agaacccga     1260 gacctgcagg ccgcattcga caccggcacg gctcacccca tccaagccgc agaactgtgc   1320
ccgccgtggc cacctgattc ccagctgtgt gtcctccagg gcgccagcta tgtgctcctc   1380
gccccgtgtg ccccgccctc gactgaggtc tgagccaaca cccctgcctc tgccgctgcc   1440
tcttcctgca ccgactccca gtcagggtcc ctcgccttcc tccctggac ccggggggccc   1500 a                                                                  1501
```

```
<210> SEQ ID NO 25
<211> LENGTH: 30
<212> TYPE: DNA
<213> ORGANISM: Rattus norvegicus

<400> SEQUENCE: 25
caccacagct gagagggaaa tcgtgcgtga                                     30

<210> SEQ ID NO 26
<211> LENGTH: 30
<212> TYPE: DNA
<213> ORGANISM: Rattus norvegicus

<400> SEQUENCE: 26
atttgcggtg cagcatggag gggccggact                                     30

<210> SEQ ID NO 27
<211> LENGTH: 51
<212> TYPE: DNA
<213> ORGANISM: Rattus norvegicus

<400> SEQUENCE: 27
gcagaggtct gaattctagt gtctatcgtt atagttcctt aacagtgtgg g             51

<210> SEQ ID NO 28
<211> LENGTH: 14
<212> TYPE: PRT
<213> ORGANISM: Rattus norvegicus

<400> SEQUENCE: 28

Cys Val Gly Val Asn Gly Asp His His Val Pro Gly Asn Gln
1               5                   10

<210> SEQ ID NO 29
<211> LENGTH: 26
<212> TYPE: DNA
<213> ORGANISM: Rattus norvegicus

<400> SEQUENCE: 29
ctaggcttgt agctgtgggg aatttc                                         26
```

<210> SEQ ID NO 30
<211> LENGTH: 22
<212> TYPE: DNA
<213> ORGANISM: Rattus norvegicus

<400> SEQUENCE: 30
tcaatcctta taagcccgtg tg                                            22

<210> SEQ ID NO 31
<211> LENGTH: 20
<212> TYPE: DNA
<213> ORGANISM: Rattus norvegicus

<400> SEQUENCE: 31
gaactttgcg agtgagctgg                                               20

<210> SEQ ID NO 32
<211> LENGTH: 20
<212> TYPE: DNA
<213> ORGANISM: Rattus norvegicus

<400> SEQUENCE: 32
tgcggagagc tttaacctcc                                               20

<210> SEQ ID NO 33
<211> LENGTH: 20
<212> TYPE: DNA
<213> ORGANISM: Rattus norvegicus

<400> SEQUENCE: 33
cctacctctt cctcatgttc                                               20

<210> SEQ ID NO 34
<211> LENGTH: 20
<212> TYPE: DNA
<213> ORGANISM: Rattus norvegicus

<400> SEQUENCE: 34
taaagggtgg agtccatcag                                               20

<210> SEQ ID NO 35
<211> LENGTH: 21
<212> TYPE: DNA
<213> ORGANISM: Rattus norvegicus

<400> SEQUENCE: 35
ggaattgcct ctgcaacatc t                                             21

<210> SEQ ID NO 36
<211> LENGTH: 18
<212> TYPE: DNA
<213> ORGANISM: Rattus norvegicus

<400> SEQUENCE: 36
gagtagatga tgggttca                                                 18

<210> SEQ ID NO 37
<211> LENGTH: 51
<212> TYPE: DNA
<213> ORGANISM: Rattus norvegicus

<400> SEQUENCE: 37
gcagaggtct gaattctagt gtctatcgtt atagttcctt aacagtgtgg g            51

```
<210> SEQ ID NO 38
<211> LENGTH: 44
<212> TYPE: DNA
<213> ORGANISM: Rattus norvegicus

<400> SEQUENCE: 38
catccttctg tagtagcttt ctgcctctgc ctccacttct ctct                    44
```

LIPID PHOSPHATE PHOSPHATASES AND USES THEREOF FOR TREATING NEURONAL DISEASES

CROSS REFERENCE TO RELATED APPLICATION

This application is a 35 USC §371 National Phase Entry Application from PCT/EP2003/010228, filed Sep. 15, 2003, which claims priority to EP 02020679.3 filed Sep. 13, 2002 and EP 03002993.8 filed Feb. 11, 2003, and designating the United States.

The present invention relates to lipid phosphate phosphatase proteins, genes coding for them, vectors and cells comprising them, antibodies directed against them, methods of identifying compounds binding to them and functional interactors as well as to the use of proteins, genes, vectors, cells, interacting compounds and functional interactors for treating neuronal diseases and/or injuries.

Axons in the central nervous system (CNS) elongate through the extracellular space over long distances (N. Tessier-Lavigne and C. S. Goodman (1996) Science 274: 1123-1133). This occurs during development (C. S. Goodman (1996) Annu. Rev. Neurosci. 19:341-377 and H. Super and E. Soriano (1994) J. Comp. Neurol. 344:101-120) and during axonal sprouting in response to partial deafferentation (C. Cotman et al. (1977) J. Neurocytol. 6:455-464 and M. Frotscher et al. (1997) Trends Neurosci. 20:218-223). The extracellular space, however, is an outgrowth repellent environment that allows axonal elongation only under specific molecular conditions (E. Stein and N. Tessier-Lavigne (2001) Science 291:1928-1938). Molecules involved in axonal outgrowth, such as semaphorins, netrins, or ephrins (S. A. Colamarino and M. Tessier-Lavigne (1995) Cell 81:621-629, H Kobayashi et al. (1997) J. Neurosci. 17:8339-8352, E. Stein et al. (1999) J. Neurosci. 19:8585-8893 and A. Steup et al. (2000) Mol. Cell Neurosci. 15:141-155) are able to transduce outgrowth promoting as well as inhibiting signals to elongating axons via specific receptors.

In the hippocampus, afferent connections from the entorhinal cortex enter in a layer-specific manner during development (T. Skutella and R. Nitsch (2001) Trends Neurosci. 24:107-113). This specific axonal navigation depends on molecular cues expressed along the pathway and in the target region (T. Skutella and R. Nitsch, supra). Transection of entorhinal axons in the adult leads to a specific deafferentation in the hippocampus with subsequent regenerative axon sprouting by remaining afferents into the denervated zones (C. Cotman et al, supra and D. A Matthews et al. (1976) Brain Res. 115:23-41). It has been shown that signaling via bioactive lipid phosphates such as phosphatidate (PA), lysophosphatidate (1- or 2-oleoyl-lysophosphatidic acid; LPA) or sphingosine-1-phosphate (S-1-P) are involved in cell migration, mitogenesis and neurite retraction (K. Jalink et al. (1994) Biochim. Biophys. Acta 1198:185-196, W. H. Moolenaar (1995) Curr. Opin. Cell Biol. 7:203-210 and N. Zhang et al. (1997) Nature 385:64-67) and in particular it has been shown that signaling via extracellular LPA plays an important role in CNS development and that postmitotic neurons are at least one endogenous source for LPA in the nervous system (N. Fukushima et al. (2000) Dev. Biol. 228:6-18). LPA has properties of an extracellular neurite repellent factor (K. Jalink (1994) supra and K. Jalink et al. (1993) Cell Growth Differ. 4:247-255). It is present in the extracellular space of the nervous system (Fukushima et al. (2000) supra and J. Bothmer et al. (1992) Neurochem. Int. 21:223-228) and mediates diverse cellular responses through the activation of multiple signal transduction pathways (W. H. Moolenaar (1995) supra). One major structural effect of LPA on neurons is rapid neurite retraction with subsequent cell rounding. Therefore, LPA and similar bioactive lipid phosphatases inhibit a regrowth of axons following neuronal lesion. Therefore, it is a problem known in the art, that after neuronal damage due to, for example, neuronal disease or trauma a regrowth of axons does not occur.

Within the context of the present invention it has been found that the expression of a family of genes called plasticity-related genes (PRGs) overcomes the repellent effect of bioactive lipid phosphates, in particular of LPA and, thus, allows the regrowth of axons in spite of the presence of bioactive lipid phosphates. Therefore, the present invention is directed at an isolated protein comprising the same or substantially the same amino acid sequence selected from the group consisting of human PRG-1 [SEQ ID NO:1], human PRG-2 [SEQ ID NO:2], human PRG-3 [SEQ ID NO:3], human PRG-4 [SEQ ID NO:4], mouse PRG-1 [SEQ ID NO:5], mouse PRG-2 [SEQ ID NO:6], mouse PRG-3 [SEQ ID NO:7], mouse PRG-4 [SEQ ID NO: 8], rat PRG-1 [SEQ ID NO:9], rat PRG-2 [SEQ ID NO:10], rat PRG-3 [SEQ ID NO:11], and rat PRG-4 [SEQ ID NO: 12], respectively, or a splice variant or a salt thereof. A protein having substantially the same amino acid sequence comprises proteins with at least about 95%, preferably at least about 96%, more preferably at least about 97%, more preferably with at least about 98% and most preferably with at least about 99% amino acid sequence identity. The amino acid exchanges are preferably so called conservative changes meaning substitutions of, for example, a polar amino acid residue by another polar amino acid residue, of a acidic amino acid residue by another acidic amino acid residue or of a basic amino acid residue by another basic amino acid residue.

Proteins having substantially the same amino acid sequence within the meaning of this invention exhibit in a preferred embodiment lipid phosphate phosphatase activity The lipid phosphate phosphatase activity of a given protein with substantially the same amino acid can be tested, for example, by the ectophosphatase assay described in example 11 below. The proteins employed in the assay can either be purified from cells or can be recombinantly expressed and purified by methods well known in the art.

In one embodiment of the present invention the protein comprises at least one fragment of the human PRG-1, PRG-2, PRG-3, and PRG-4 or mouse PRG-1, PRG-2, PRG-3 and PRG-4 or rat PRG-1, PRG-2, PRG-3 and PRG-4. A fragment within the meaning of the present invention refers to one of the proteins according to SEQ ID NOs: 1 to 12 bearing at least one N-terminal, C-terminal and/or internal deletion. The resulting fragment has a length of at least about 50, preferably of at least about 100, more preferably of at least about 150, more preferably of at least about 200, more preferably of at least about 250, more preferably of at least about 300 and in case of human PRG-1 and PRG-2 or mouse PRG-1 and PRG-2 or rat PRG-1 and rat PRG-2, more preferably of at least about 350 and most preferably of at least about 400 amino acids.

Preferably, the fragment is an N-terminal fragment which comprises 330 amino acids or less as outlined above, which are highly conserved between, for example, PRG-1 and members of the family of LPP membrane-associated phosphatic acid phosphatase ecto-enzymes, which have six membrane spanning domains with their active site located on the external surface of the plasma membrane. This domain comprises preferably the catalytic region. For example, human PRG-1 carries a catalytic histidine at position 252, which is involved in the phosphatase activity of human PRG-1. Similarly human, mouse and rat PRG-3 comprises a domain highly homologous to human PRG-1, which in rat PRG-3 spans amino acids 210 to 212 and includes a histidine residue at amino acid 209. Therefore, in a preferred embodiment any N-terminal fragment of the proteins of the present invention comprises the catalytic site, preferably including the conserved His-residue. The fragment itself has preferably an amino acid sequence identity with hPRG-1, hPRG-2, hPRG-3, hPRG-4, mPRG-1, mPRG-2, mPRG-3, mPRG-4, rPRG-1, rPRG-2, rPRG-3, and rPRG-4, respectively, of at least about 95%, preferably of at least about 96%, more preferably of at least about 97%, more preferably of at least about 98%, more preferably of at least about 99% and most preferably of 100%.

The C-terminal cytoplasmatic part of the PRG proteins is potentially involved in regulation of lipid phosphate phosphatase activity and/or signaling and, thus, a further preferred fragment comprises a C-terminal fragment, which comprises about 413 amino acids or less as outlined above and which comprises regions required for above activity of the PRG proteins. The fragment itself has preferably an amino acid sequence identity with hPRG-1, hPRG-2, hPRG-3, hPRG-4, mPRG-1, mPRG-2, mPRG-3, mPRG-4, rPRG-1, rPRG-2, rPRG-3, and rPRG-4, respectively, of at least about 95%, preferably of at least about 96%, more preferably of at least about 97%, more preferably of at least about 98%, more preferably of at least about 99% and most preferably of 100%.

In a further aspect the present invention is directed at a nucleic acid, which comprises at least one nucleic acid encoding one of the proteins of the present invention. Preferably the nucleic acid consists of DNA or RNA, wherein the DNA preferentially is either single or double stranded. Also comprised are DNA's, which hybridize to one of the aforementioned DNA's preferably under stringent conditions like, for example, hybridization at 60° C. in 2.5×SSC buffer and several washes at 37° C. at a lower buffer concentration like, for example, 0.5×SSC buffer and which encode proteins exhibiting lipid phosphate phosphatase activity and/or association with plasma membranes. Additional reagents required for carrying out stringent Northern or Southern blots like, for example, single stranded salmon sperm DNA are well known in the art. Also comprised are nucleic acid sequences, which are related to the nucleic acids according to SEQ ID No. 13-24 and/or the hybridizing nucleic acids as outlined above by the degeneration of the genetic code.

In a preferred embodiment of the nucleic acid of the present invention the nucleic acid comprises a nucleic acid selected from the group consisting of the human PRG-1 gene [SEQ ID NO:13], the human PRG-2 gene [SEQ ID NO:14], the human PRG-3 [SEQ ID NO:15], the human PRG-4 [SEQ ID NO:16], the mouse PRG-1 gene [SEQ ID NO:17], the mouse PRG-2 gene [SEQ ID NO:18], the mouse PRG-3 [SEQ ID NO:19], the mouse PRG-4 [SEQ ID NO:20], the rat PRG-1 [SEQ ID NO:21], the rat PRG-2 [SEQ ID NO:22], the rat PRG-3 [SEQ ID NO:23], and the rat PRG-4 gene [SEQ ID NO:24].

In a further embodiment the nucleic acid of the present invention further comprises at least one promoter, enhancer, intron and/or polyA-sequence. Preferred promoters or enhancers posses tissue specificity, in particular neuronal specificity and more particular a specificity for growing neurons. Examples of such promoters and/or enhancers are the neuron specific enolase promoter (Erickson, R. P. and Bernard, O. (2002) J. Neuro Science Res 68:738-44), the peripherin promoter (Weinstein, D. E. et al. (1999) Brain Res. Dev. Brain Res. 116:29-39), the synapsin promoter (Flood, D. G. et al. (1999) Am. J. Pathol. 155:663-72) and the Thy 1 promoter (Kahle, P. J. et al. (2001) Am. J. Pathol. 159:2215-25).

In some instances it might be desirable to interfere with, for example, the transcription or translation of the nucleic acids of the present invention and, therefore, the present invention is also directed at a nucleic acid, which is complementary to the nucleic acid of the present invention and, thus, is capable of inhibiting, for example, transcription or translation. A preferred embodiment of such a complementary nucleic acid is a so called antisense oligonucleotide (R. Q. Zheng and D. M. Kemeny (1995) Clin. Exp. Immunol. 100:380-2, W. Nellen and C. Lichtenstein (1993) Trends. Biochem. Sci. 18:419-423 and C. A. Stein (1992) Leukemia 6:967-74), ribozymes (M. Amarzguioui and H. Prydz (1998) Cell. Mol. Life Sci. 54:1175-1202, N. K. Vaish et al (1998) Nucleic Acids Res. 96:5237-5242, Persidis (1997) Nat. Biotechnol. 15:921-922 and L. A. Couture and D. T. Stinch-comb (1996) Trends Genet. 12:510-515) and/or so called small interfering RNA-molecules (siRNAs) (S. M. Elbashir et al. (2001) Nature 411:494-498). Anti-sense oligonucleotides are able to decrease the stability of the above described nucleic acids and/or can inhibit the translation. Similarly the use of siRNA-oligonucleotides can also lead to a reduction in the amount of the translated polypeptides. Anti-sense oligonucleotides have in a preferred embodiment a length of at least 20, preferable of at least about 30, more preferably of at least about 40 and most preferably a length of at least about 50 nucleic acids.

Oligonucleotides are generally rapidly degraded by endo- or exonucleases, which are present in the cell, in particular by DNases und RNases and, therefore, it is advantageous to modify the nucleic acids which are used, for example, in anti-sense strategies, as ribozymes or siRNAs to stabilize them against degradation and thereby prolong the time over which an effective amount of the nucleic acid is maintained within the cell (L. Beigelmann et al. (1995) Nucleic acids Res. 23:3989-94, WO 95/11910, WO 98/37340 and WO 97/29116). Typically such stabilization can be obtained by the introduction of one or more internucleotide phosphate groups and/or by the introduction of one or more non-phosphor-internucleotides.

Suitable modified internucleotides are summarized in, for example, Uhlmann and Peimann (1990) Can. Rev. 90:544. Modified internucleotide phosphate residues and/or non-phosphate bridges which can be used in a nucleic acid of the invention comprise, for example, methylphosphonate, phosphorthioate, phosphoramidate, phosphordithionate, phosphate ester, non-phosphor internucleotide analogues, which can be used in nucleic acids of the invention include, for example, siloxane bridges, carbonate bridges, carboxymethylester, acetamid bridges and/or thioether bridges.

A further aspect of the present invention is directed at a vector comprising a protein according to the present invention and/or a nucleic acid according to the present invention. A vector within the meaning of the present invention is a protein or a nucleic acid or a mixture thereof which is capable of being introduced or of introducing the proteins and/or nucleic acid comprised into a cell. It is preferred that the proteins encoded by the introduced nucleic acid are expressed within the cell upon introduction of the vector.

In a preferred embodiment the vector of the present invention comprises plasmids, phagemids, phages, cosmids, artificial mammalian chromosomes, knock-out or knock-in constructs, viruses, in particular adenovirus, vaccinia virus, lentivirus (Chang, L. J. and Gay, E. E. (20001) Curr. Gene Therap. 1:237-251), Herpes simplex virus (HSV-1, Carlezon, W. A. et al. (2000) Crit. Rev. Neurobiol.), baculovirus, retrovirus, adeno-associated-virus (AAV, Carter, P. J. and Samulski, R. J. (2000) J. Mol. Med. 6:17-27), rhinovirus, human immune deficiency virus (HIV), filovirus and engineered versions thereof (see, for example, Cobinger G. P. et al (2001) Nat. Biotechnol. 19:225-30), virosomes, "naked" DNA liposomes, and nucleic acid coated particles, in particular gold spheres. Particularly preferred are viral vectors like adenoviral vectors or retroviral vectors (Lindemann et al. (1997) Mol. Med. 3:466-76 and Springer et al. (1998) Mol. Cell. 2:549-58). Liposomes are usually small unilamellar or multilamellar vesicles made of neutral cationic and/or anionic lipids, for example, by ultrasound treatment of liposomal suspensions. The DNA can, for example, be ionically bound to the surface of the liposomes or internally enclosed in the liposome. Suitable lipid mixtures are known in the art and comprise, for example, cholesterol, phospholipide like, for example, phosphatidylcholin (PC), phosphatidylserin (PS) and the like, DOTMA (1,2-Dioleyloxpropyl-3-trimethylammoniumbromid) and DPOE (Dioleoylphosphatidylethanolamin) which both have been used on a variety of cell lines.

Nucleic acid coated particles are another means for the introduction of nucleic acids into cells using so called "gene guns", which allow the mechanical introduction of particles into the cells. Preferably the particles itself are inert, and therefore, are in a preferred embodiment made out of gold spheres.

In a further aspect the present invention is directed at an isolated cell comprising a protein of the present invention, a nucleic acid of the present invention and/or a vector of the present invention. Cells of the present invention can be prokaryotic or eukaryotic cells and in a preferred embodiment the cells of the present invention are stem cells, in particular non-human embryonic stem cells, embryonic stem cell lines, foetal stem cells, adult stem cells, neuronal precursor cells or neuronal cells in particular axons (Hsieh, G. et al. (2002) Hum. Gene Therap., 13:579-604 and Martinez-Serrano, A. et al. (2001) Curr. Gene Therap. 1:279-299). The cells preferably comprise the nucleic acids extrachromosomally or interchromosomally.

A further aspect of the present invention is a transgenic non-human animal generated from a cell or cells of the present invention. The animal can be a mosaic animal, which means that only part of the cells making up the body comprise cells of the present invention or the animal can be a transgenic animal which means that all cells of the animal are derived from a cell of the present invention. Mosaic or transgenic animals can be either homo- or heterozygous with respect to the nucleic acid of the present invention contained within the cell of the present invention. In a preferred embodiment the transgenic animals are either homo- or heterozygous knock-out or knock-in animals with respect to the genes which code for the proteins of the present invention.

In a further aspect the present invention is directed at an antibody directed against a protein of the present invention. The term "antibody" comprises monoclonal and polyclonal antibodies and binding fragments thereof, in particular Fc-fragments as well as so called "single-chain-antibodies" (Bird R. E. et al (1988) Science 242:423-6) and diabodies (Holliger P. et al (1993) Proc. Natl. Acad. Sci. U.S.A. 90:6444-8).

In a further aspect the present invention is directed at a method of producing a protein of the present invention or a nucleic acid of the present invention and comprises the steps of: a) cultivating a cell of the present invention and b) isolating the protein and/or the nucleic acid. If the method is used primarily to isolate nucleic acids then in an preferred embodiment the cells, which are used are prokaryotic cells, in particular E. coli. cells If the method is used primarily for the isolation of proteins of the invention than the cells can be either of prokaryotic or eukaryotic origin. Someone of skill in the art is aware of a variety of different cell types suitable for the production of proteins like, for example, E. coli, Sf9, Hi5, P. pastoris, COS and HeLa. Eukaryotic cells are preferably chosen, if it is desired that the proteins produced by the cells exhibit an essentially natural pattern of glycosylation and prokaryotic cells are chosen, if, for example, glycosylation or other modifications, which are normally introduced into proteins only in eukaryotic cells, are not desired or not needed.

In a further aspect the present invention is directed at a method of isolating compounds interacting with a protein of the present invention comprising the steps of: a) contacting one or more of the proteins of the present invention, preferably one, with at least one potentially interacting compound, and b) measuring binding of said compound to said protein. This method is suitable for the determination of compounds that can interact with the proteins of the present invention and to identify, for example, inhibitors, activators, competitors or modulators of proteins of the present invention, in particular inhibitors, activators, competitors or modulators of the enzymatic activity of the proteins of the present invention.

The potentially binding substance, whose binding to the protein of the present invention is to be measured, can be any chemical substance or any mixture thereof. For example, it can be a substance of a peptide library, a combinatory library, a cell extract, in particular a plant cell extract, a "small molecular drug", a protein and/or a protein fragment.

The term "contacting" in the present invention means any interaction between the potentially binding substance(s) with the proteins of the invention, whereby any of the two components can be independently of each other in a liquid phase, for example in solution, or in suspension or can be bound to a solid phase, for example, in the form of an essentially planar surface or in the form of particles, pearls or the like. In a preferred embodiment a multitude of different potentially binding substances are immobilized on a solid surface like, for example, on a compound library chip and the protein of the present invention is subsequently contacted with such a chip.

The proteins of the present invention employed in a method of the present invention can be full length proteins or a fragments with N/C-terminal and/or internal deletions. Preferably the fragments are either N-terminal fragments comprising the enzymatic region of the protein or C-terminal fragments comprising the cytoplasmic region, depending on whether potentially interacting compounds are sought that specifically interact with the N- or C-terminal fragment Measuring of binding of the compound to the protein can be carried out either by measuring a marker that can be attached either to the protein or to the potentially interacting compound. Suitable markers are known to someone of skill in the art and comprise, for example, fluorescence or radioactive markers. The binding of the two components can, however, also be measured by the change of an electrochemical parameter of the binding compound or of the protein, e.g. a change of the redox properties of either the protein or the binding compound, upon binding. Suitable methods of detecting such changes comprise, for example, potentiometric methods. Further methods for detecting and/or measuring the binding of the two components to each other are known in the art and can without limitation also be used to measure the binding of the potential interacting compound to the protein or protein fragments of the present invention. The effect of the binding of the compound or the activity of the protein can also be measured indirectly, for example, by assaying the phosphatase activity of the protein after binding.

As a further step after measuring the binding of a potentially interacting compound and after having measured at least two different potentially interacting compounds at least one compound can be selected, for example, on grounds of the measured binding activity or on grounds of the detected increase or decrease of protein activity, in particular lipid phosphate phosphatase activity upon binding. The phosphatase activity can be measured, for example, as described in example 11.

The thus selected binding compound is than in a preferred embodiment modified in a further step. Modification can be effected by a variety of methods known in the art, which include without limitation the introduction of novel side chains or the exchange of functional groups like, for example, introduction of halogens, in particular F, Cl or Br, the introduction of lower alkyl groups, preferably having one to five carbon atoms like, for example, methyl, ethyl, n-propyl, isopropyl, n-butyl, isobutyl, tert-butyl, n-pentyl or isopentyl groups, lower alkenyl groups, preferably having two to five carbon atoms, lower alkinyl groups, preferably having two to five carbon atoms or through the introduction of, for example, a group selected from the group consisting of $NH_2$, $NO_2$, OH, SH, NH, CN, aryl, heteroaryl, COH or COOH group.

The thus modified binding substances are than individually tested with the method of the present invention, i.e. they are contacted with the protein and subsequently binding of the modified compounds to the protein is measured. In this step both the binding per se can be measured and/or the effect of the function of the protein like, e.g. the enzymatic activity of the protein can be measured. If needed the steps of selecting the binding compound, modifying the binding compound, contacting the binding compound with a protein of the invention and measuring the binding of the modified compounds to the protein can be repeated a third or any given number of times as required. The above described method is also termed "directed evolution" since it involves a multitude of steps including modification and selection, whereby binding compounds are selected in an "evolutionary" process optimizing its capabilities with respect to a particular property, e.g. its binding activity, its ability to activate, inhibit or modulate the activity, in particular the phosphatase activity of the proteins of the present invention.

A further aspect of the present invention is a method of isolating compounds functionally interacting with the activity of the proteins of the present invention comprising the steps of: a) contacting a neuronal cell that comprises a wt nucleic acid coding for a protein selected from the group consisting of SEQ ID NOs: 1 to 12, a splice variant thereof, or a fragment thereof with a potential functional interactor, b) contacting the cell with a bioactive lipid phosphate, and c) measuring neurite movement or phosphatase activity.

The term "contacting" has to be understood as previously defined and comprises any possibility of interaction between the potential functional interactor and a neuronal cell. Contacting also comprises the introduction of the potential functional interactor into the neuronal cell which can be effected by a variety of methods including, for example, electroporation, which allows influx of a potential functional interactor contained in the medium surrounding the neuronal cell into the neuronal cell. A neuronal cell that comprises a wt nucleic acid coding for a PRG protein (as indicated in SEQ ID NOs: 1 to 12) can be any neuronal cell capable of neurite movement. The cell may or may not express the wild-type nucleic acid depending on, for example, the developmental stage of the neuronal cell. For example entorhinal cortex cells of embryonic day 16 (E16), which exhibit neurite movement, do not express PRG-1 while entorhinal cortex cells of postnatal day 0 (P0) do express PRG-1. The choice of either a cell that already expresses or does not express the wild-type nucleic acids will depend on the functional interaction of the potential functional interactor that is sought. If, for example, a functional interactor is sought, that activates transcription within the cell normally not expressing PRG-1 than, for example, an E16 cell could be chosen. If functional interactors are sought that primarily interact on the protein level, i.e. that activate or suppress phosphatase activity of already expressed PRG-1 than neuronal cells expressing PRG-1 would be chosen like, for example, P0 cells.

Bioactive lipid phosphates are lipid phosphates which inhibit neurite movement of neuronal cells, which do not express PRG-1, like for example, E16 cells. Examples of such bioactive lipid phosphates comprise PA, LPA and S-1-P. Whether a lipid phosphate, which can be used in the method of the present invention is bioactive can be determined by, for example, the experiment described in Example 9.

Methods for measuring neurite movements are well-known in the art and are described, for example, in Savaskan et al. (1999) European J. Neurosci. 11:319-326. One way of measuring neurite movement is scoring of the cells after contacting with a bioactive lipid phosphate. It is possible to categorize the cells into at least three different categories, i.e. round cells, cells with short processes and cells with long processes. It is also possible to quantify the effect by measuring the length of the neurite processes. The effect of the potential functional interactor can be determined by comparing the neurite movement of the neuronal cell, the categories the cells are in or the length of the neurite processes after contacting the cell with a bioactive lipid phosphate with or without the functional interactor. Other ways to assess the effect of potential functional interactors are the determination of the expression level of the PRG genes and/or proteins or the enzymatic activity of the proteins.

In a further embodiment the method includes the additional steps of: a) contacting a neuronal cell that comprises a mutant nucleic acid coding for a mutant of the proteins selected from the group consisting of SEQ ID NOs: 1 to 12, a splice variant thereof, or a fragment thereof or that contains a knock-out of the wt nucleic acid coding for one of said proteins with a potential functional interactor, b) contacting said cell with a bioactive lipid phosphate, and c) measuring neurite movement. The above described neuronal cell is preferably incapable of expressing a functional PRG protein and, thus, can not be stimulated by any functional interactor to activate PRG genes or PRG protein function. Therefore, any potential functional interactor, which shows an effect on the neurite movement of neuronal cells comprising wild-type PRG genes but shows no effect in the neuronal cell comprising mutants or knock-out PGR genes have thereby been shown to functional interact with the PRG genes. Once such an interactor has been identified the mode of functional interaction can be further analyzed and to that end the amount of PRG mRNA and/or protein expressed or the activity of the PRG protein can be determined by a variety of different techniques, which are either known in the art or described herein.

In a preferred embodiment the method of the invention comprises the further steps of: a) modifying the functional interactor to generate a variety of modified functional interactors, b) contacting a neuronal cell comprising a wild-type nucleic acid coding for a protein selected from the group consisting of SEQ ID NOs: 1 to 12, a splice variant thereof, or a fragment thereof and if needed a cell that comprises a mutant nucleic acid coding for a mutant of the protein selected from the group consisting of SEQ ID NOs: 1 to 12, a splice variant thereof, or a fragment thereof with the modified functional interactors, c) contacting said cell or cells with a bioactive lipid phosphate, d) measuring the neurite movement, and e) if needed repeating steps a) to d) for one or more times. The modification of the functional interactor can be any of the modifications outlined above with respect to the modification of an interacting compound and the modification and selection steps can be repeated one or several times until a functional interactor has been selected that shows the desired functional interaction, e.g. repression or activation of the activity in particular of the enzymatic activity of PRG proteins.

In a further embodiment of the method of the present invention the interacting compound identified as outlined above or the functional interactor identified as outlined above, which may or may not have gone through additional rounds of modification and selection, is admixed with suitable auxiliary substances and/or additives. Such substances comprise pharmacological acceptable substances, which increase the stability, solubility, biocompatibility, or biological half-life of the interacting compound or the functional interactor or comprise substances or materials, which have to be included for certain routs of application like, for example, intravenous solution, sprays, Band-Aids or pills.

Since expression of PRG-1 can prevent LPA induced neurite retraction and/or expression of rat PRG-3 induces neurite extension these proteins have another utility in the treatment of neuronal injuries and diseases. Accordingly a further aspect of the present invention is a pharmaceutical composition for the treatment of neuronal injuries or diseases comprising a protein of the invention, a nucleic acid of the invention, a vector of the invention, a cell of the invention, an antibody of the invention, a binding component isolated by a method of the invention and/or a functional interactor isolated by a method of the invention and if needed suitable auxiliary substances and/or additives.

Accordingly, a further aspect of the present invention is the use of a pharmaceutical composition of the invention for the production of a medicament for the treatment of neuronal diseases or injuries. Neuronal diseases which can be treated with the pharmaceutical composition comprise spinal cord lesion, Alzheimer disease and stroke. Typical neuronal injuries comprise traumata of any sort in particular head traumata resulting in the damage of neurons and in particular the severing of neuronal connections.

As stated above it has also been found that PRG proteins are differentially expressed in certain tissues and that they have been found to be differentially expressed in certain diseases, however, differential expression is also associated with certain disease states. Thus, PRG proteins present attractive targets for diagnosis and treatment of a variety of diseases. Therefore, another aspect of the present invention is the use of the proteins or nucleic acids of the present invention as diagnostic marker for the diagnosis of a disease or disease state, whereby the presence, the absence, or the amount of PRG proteins is evaluated by, for example, immunological methods, RT-PCR, Northern blot. For the immunological detection and/or quantification methods the antibodies of the present invention can be used.

As PRG is differentially regulated in neuronal diseases PRG proteins or nucleic acids are in a preferred embodiment used as diagnostic marker for the diagnosis of neuronal diseases.

Furthermore PRG proteins are overexpressed in tumors. PRG-1, for example, is overexpressed in a variety of tumor cells, e.g. astroglioma WHO Grad III-IV, neuroblastoma, kidney cell carcinoma, myoblastoma and ovarial cell carcinoma, and in particular it has also been found to be overexpressed in migrating, i.e. metastasizing cancer cells which have lost the anchorage dependence for growth. Therefore, PRG proteins also present attractive targets for diagnoses and treatment of tumors, in particular metastasizing tumors. Consequently, a further aspect of the present invention is the use of PRG proteins and nucleic acids of the present invention as a tumor markers and, preferably, as metastatic markers. Because of the above property PRG proteins are also therapeutic targets for the development of drugs, which modulate, preferably inhibit the function of PRG proteins. Such drugs can be identified with above-described methods for identifying interacting or functional interacting compounds.

In a preferred embodiment, PRG proteins of the present invention are used for diagnosis of cancers selected from the group of cancers consisting of neuroblastoma, astroglioma, ovarial cell carcinoma, prostatic cell carcinoma and breast cell carcinoma.

In addition, PRG proteins, in particular PRG-1, have been found to be overexpressed in differentiating sperm cells and, thus, a further embodiment of the present invention is the use of the PRG proteins or nucleic acids as diagnostic targets for the diagnosis of infertility, in which a lack of PRG proteins would indicate either a low amount of differentiating sperm cells or the malfunction of the sperm cells. The amount of expression of PRG proteins or nucleic acids can be detected by, for example, in situ immunofluorescence, in situ Northern blots. The skilled persons knows a variety of additional methods that are suitable to determine the amount and distribution of PRG proteins and RNA within a cell and/or tissue.

The following figures and examples merely serve to illustrate the invention and should not be construed to restrict the scope of the invention to the particular embodiments of the invention described in the examples. All references cited in the text and the disclosure of the priority applications EP 02 020 679.3 and EP 03 002 993.8 are hereby incorporated in their entirety by reference.

FIGURES

FIG. 1 Panel A depicts the human PRG-1 amino acid sequence (SEQ ID NO. 1). The first 300 amino acids are highly conserved among LPP family members. The other 400 amino acids (gray boxed sequence) of PRG-1 show no homologies to known sequences. The catalytic histidine (His-252) is marked with an asterisk. Panel B depicts rPRG-3 [nucleic acid: [SEQ ID NO:23: amino acid: SEQ ID NO:11]. Start and stop codons are marked with a dark box. Putative transmembrane domains are underlined in grey, the C-terminal tail is indicated light grey. The probes, which were used for in situ hybridization are marked with a black line.

FIG. 2 Panel A depicts the hydrophobicity profile of human PRG-1 protein predicted by the Kyte and Doolittle algorithms. The gray shaded area of PRG-1 is predicted as hydrophilic and located in the cytosol. Panel B depicts the hydrophobicity profile of rat PRG-3-protein. The numbers at the bottom of the profiles refer to amino acid residues from the amino terminus. Panel C depicts the in silico determined phylogenetic tree of different PRG-proteins and LPP-1.

FIG. 3 Northern blot analysis of PRG-1 mRNA expression

Figure 4:
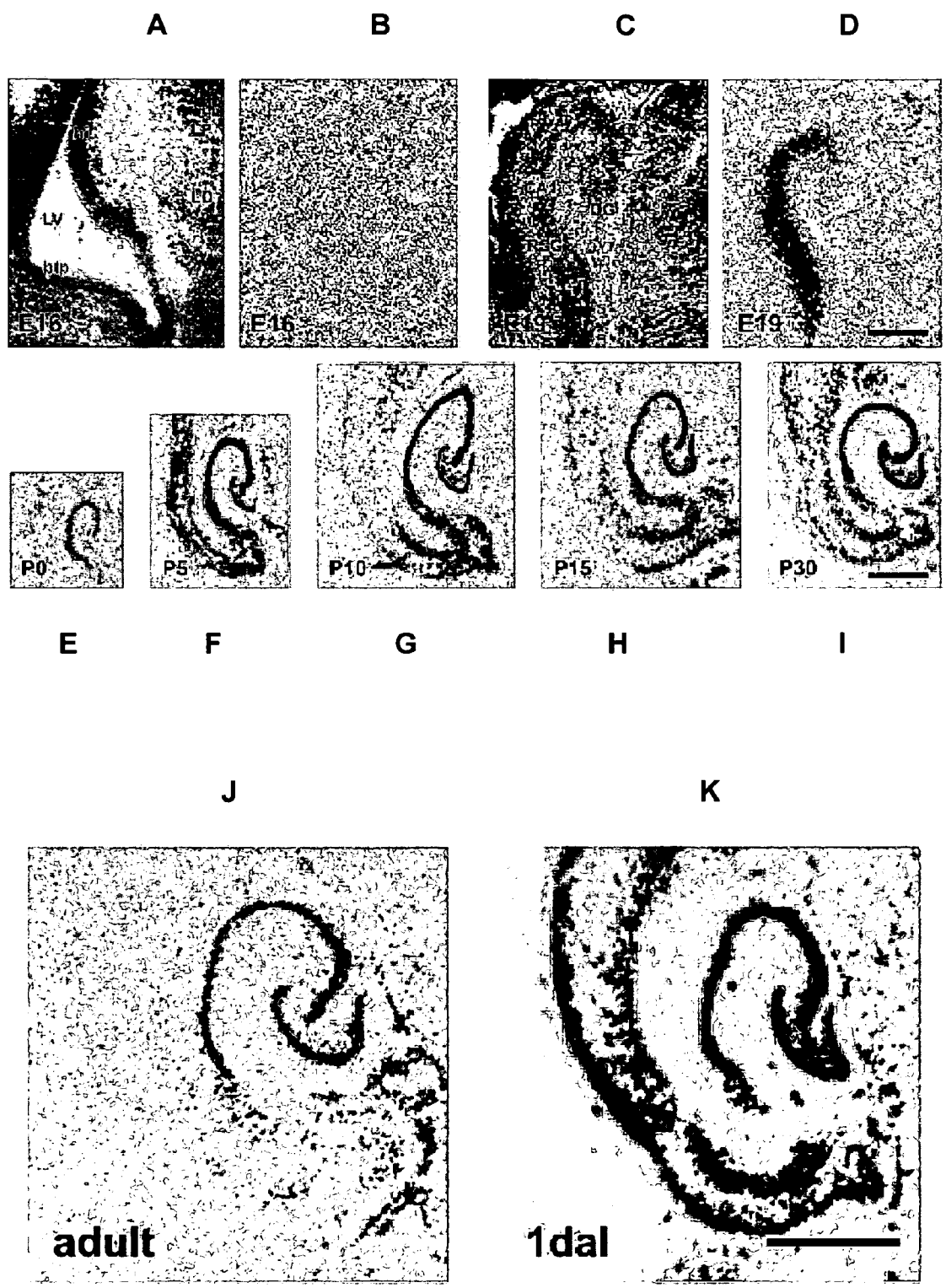

FIG. 4 Expression pattern of PRG-1 mRNA in the developing and lesioned rat brain detected by in situ Northern blot. Panel A shows the Toluidene blue staining of a brain section on embryonic day 16 (E16). Panel B shows the in situ hybridization signal with a probe specific for PRG-1 mRNA of the same section as shown in panel A. Panel C shows a Toluidene blue staining of a brain section on embryonic day 19 and panel D shows the in situ hybridization with a probe specific for PRG-1 mRNA of the same section as shown in panel C. Panels E through K show in situ Northern blot analysis of brain sections at days 0, 5, 10, 15, 30 after birth, in an adult and one day after lesion, respectively. The scale bar in E19 equals 850 µm. The scale bar in P30 equals 740 µm and also applies to P0-P15. The scale bar in 1 dal equals 500 µm and also applies to adult. "LV" means lateral ventricle, "LP" means lateral posterior thalamic nucleus, "LD" means laterodorsal thalamic nucleus, "bcp" means basal telencephalic plate, posterior part, "CA1" means cornu ammonis, "DG" means dentate gyrus, "RSG" means retrosplenial granular cortex, "dal" means days after lesion.

Figure 5:
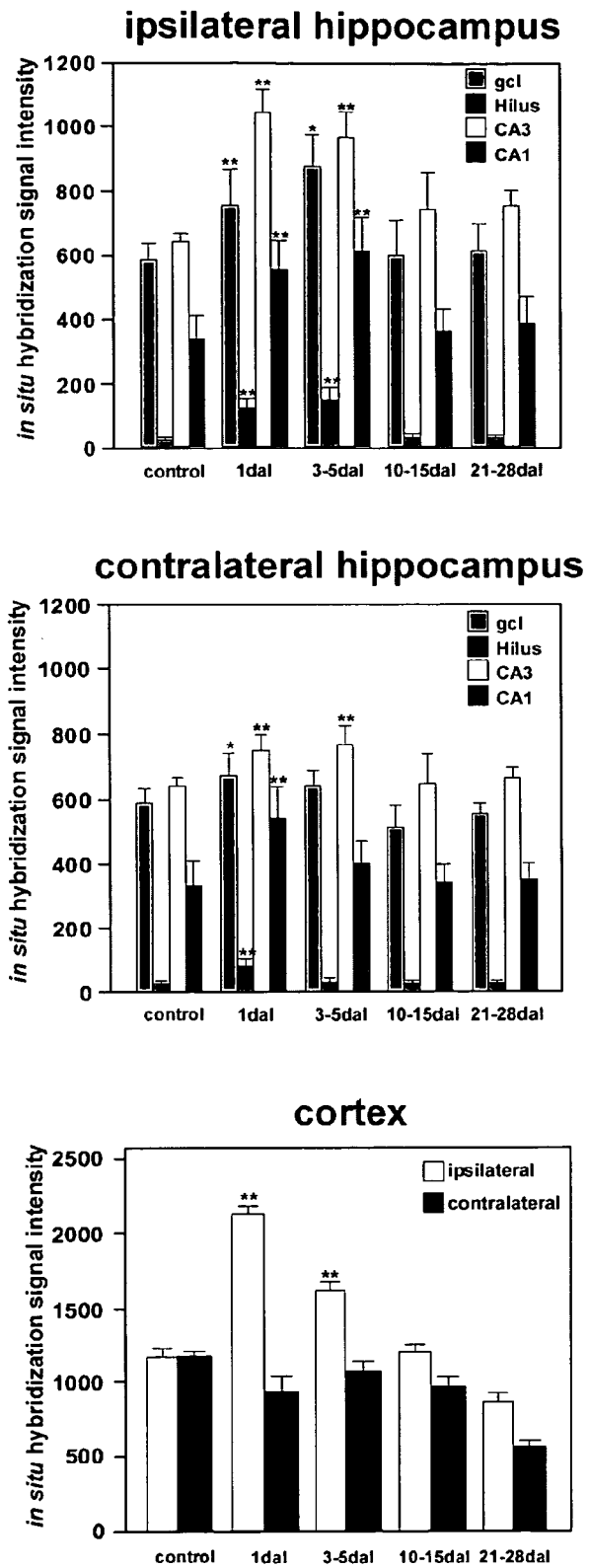

FIG. 5 Quantification of the in situ hybridization signals in different regions of the brain after lesion. "gcl" means granule cell layer, "CA3" means cornu ammonis 3, "CA1" means cornu ammonis and "dal" means days after lesion.

FIG. 6 Overexpression of a PRG-1-eGFP fusion protein in COS-7 cells. Panel A shows the fluorescence of the green fluorescent protein, panel B shows the fluorescence of a fluorecently labeled anti-PRG-1 peptide antibody and panel C shows the colocalization of the fluorescence of the PRG-1-eGFP and the anti-PRG-1 antibody. In each picture the processes of the COS-7 cells are marked with a white arrow. The scale bar depicts a length of 10 µm. Panel D shows the result of a Western blot using an antiserum raised against a C-terminal peptide of PRG-1.

FIG. 7 Immunocytochemical analysis of PRG-1 in the adult rat hippocampus prior and after lesion. Pyramidal neurons are labeled in the CA1 and CA3 region. Polymorphic cells are stained in the hilus. The outermoelcular layer is marked with black errors. "Gcl" means granule cell layer "Oml" means outer molecular layer and "hi" means hilus. The scale bar in panel A and B equals 580 µm. Panel C shows immunoblots from total protein extracts of adult control and deafferentiated hippocampus five days after lesion.

Figure 8:
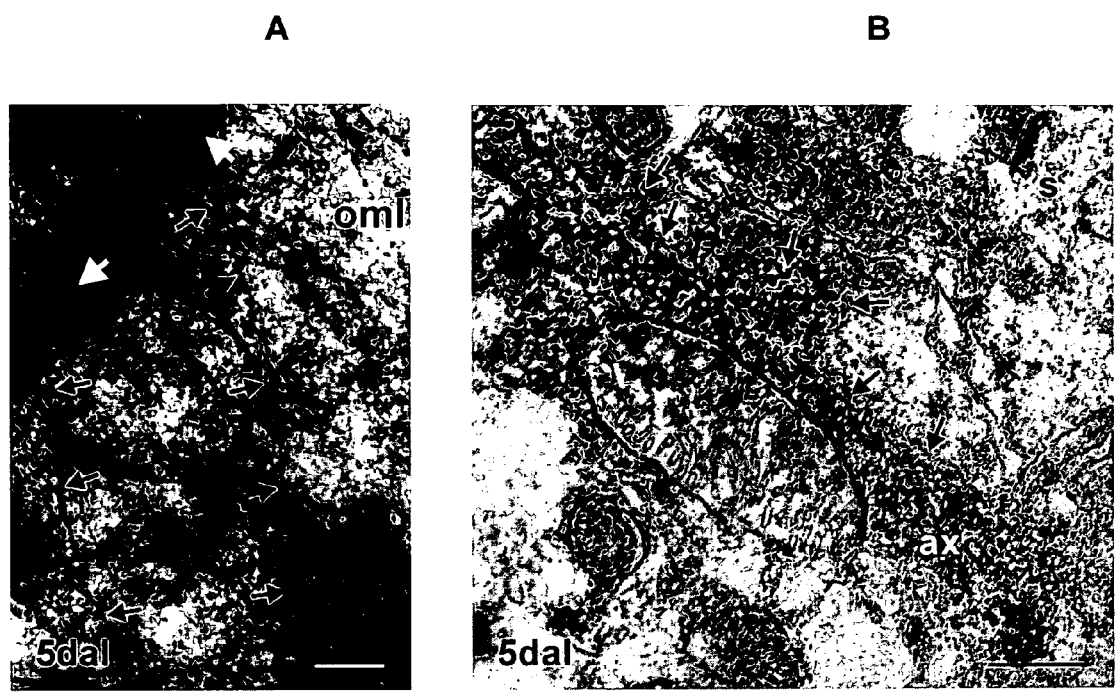

FIG. 8 Panel A shows a higher magnification of the boxed area of panel B of FIG. 7. Immuno-stained axons are marked with black arrows and the terminal branches with white arrows. Panel B shows an electron micrograph of a PRG-1 immunopositive axon. The immunopositive axon is delineated by black arrows, while its terminal branch is delineated by gray arrows. "oml" means outer molecular layer and "ax" means axon and "s" means spine. The scale bar in panel A equals 20 µm and the scale bar in panel B equals 0.4 µm.

Figure 9:
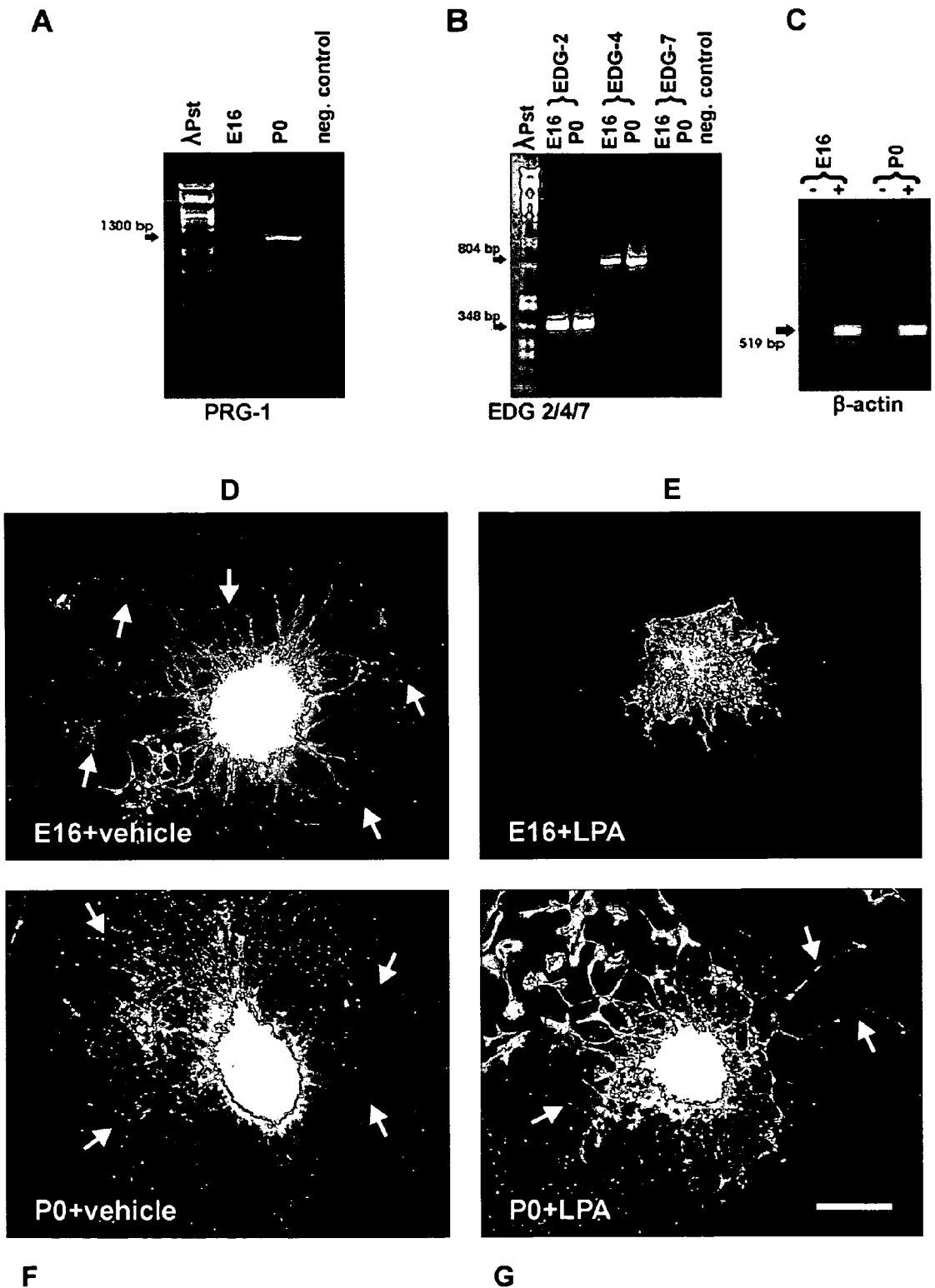

FIG. 9 Panel A-C show the result of an RT-PCR analysis of RNA from tissues from E16 and P0 explants. The amplification was carried out with primers specific for PRG-1 (panel A), EDG 2, 4 or 7 (panel B) and β-actin (panel C). Panel D and E depict explants from rat entorhinal cortex at embryonic day 16 and panel F and G depict rat entorhinal cortex at postnatal day 0 (bottom row of panels). Outgrowing axons are marked with white arrows and the panels D and F show neurite retraction in the presence of vehicle (0,9% NaCl) while panels E and G show neurite retraction upon the addition of 100 nmol/l LPA. The scale bar in panel G equals 20 µm.

Figure 10:
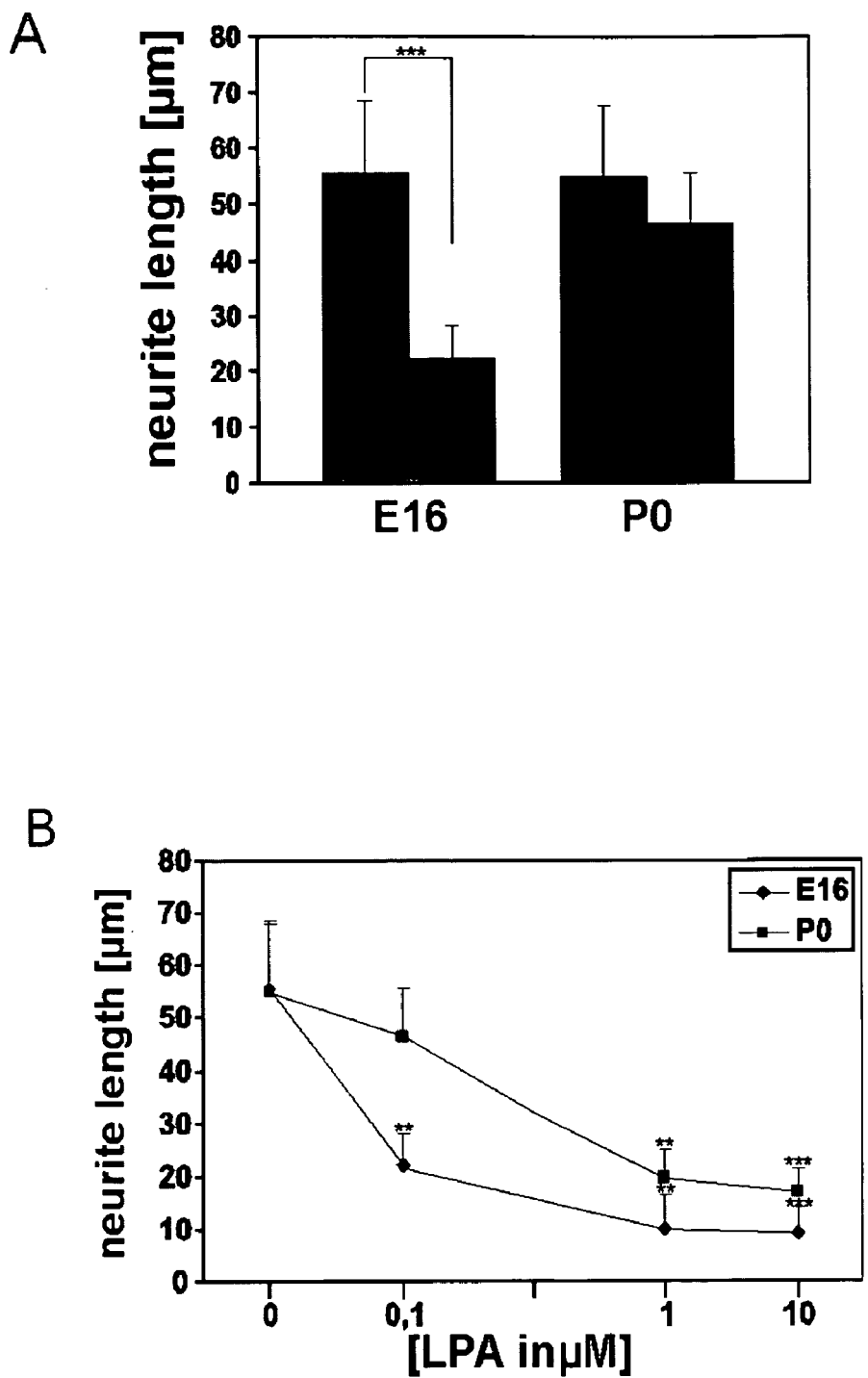

FIG. 10 Panel A shows the neurite outgrowth length in control cultures (left bar) and LPA treated cultures, (right bar) in E16 and postnatal explants (P0) in µm. Panel B shows the dose-response of LPA on P0 and E16 explants.

Figure 11:
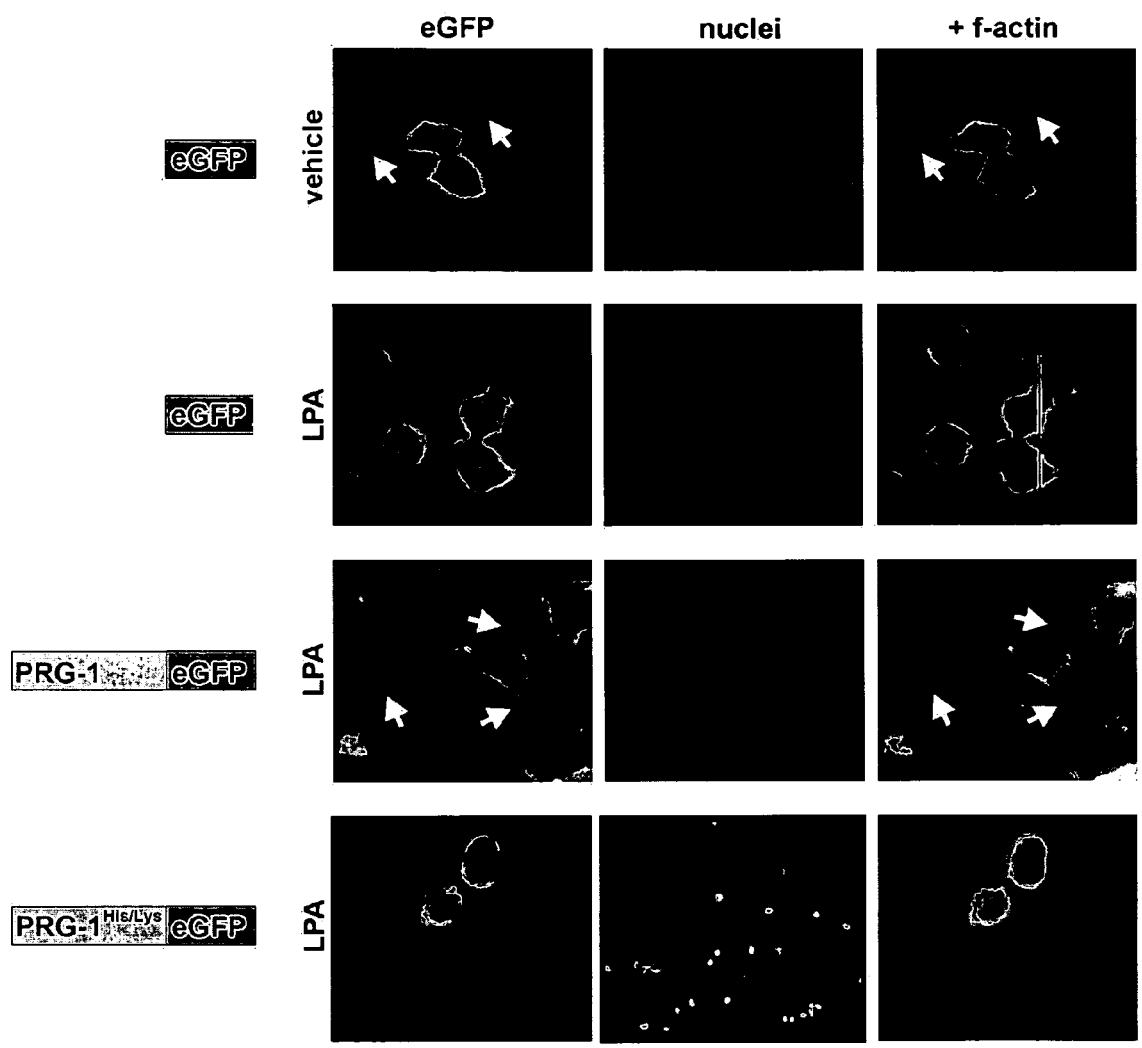

FIG. 11 Depicts cell rounding and neurite retraction in response to LPA in N1E-115 cells. The cells depicted in the first three top panels were transfected with a plasmid containing only eGFP and were not treated with LPA but with vehicle only. The cells in the second row were transfected with a plasmid containing only eGFP but were treated with 10 µmol/l LPA, the cells of the third row were transfected with a plasmid coding for a PRG-1-eGFP fusion protein and were treated with 10 µmol/l LPA while the cells depicted in the bottom row of panels were transfected with a mutant PRG-1-eGFP fusion protein, which carried a His-Lys exchange in the catalytic histidine of PRG-1 (PRG-1$^{His/Lys}$) and were also treated with 10 µmol/l LPA. The panels on the left show transfected cells, panels in the middle show nuclear staining (Hoechst staining) and panels on the right show merged images with f-actin staining.

Figure 12:
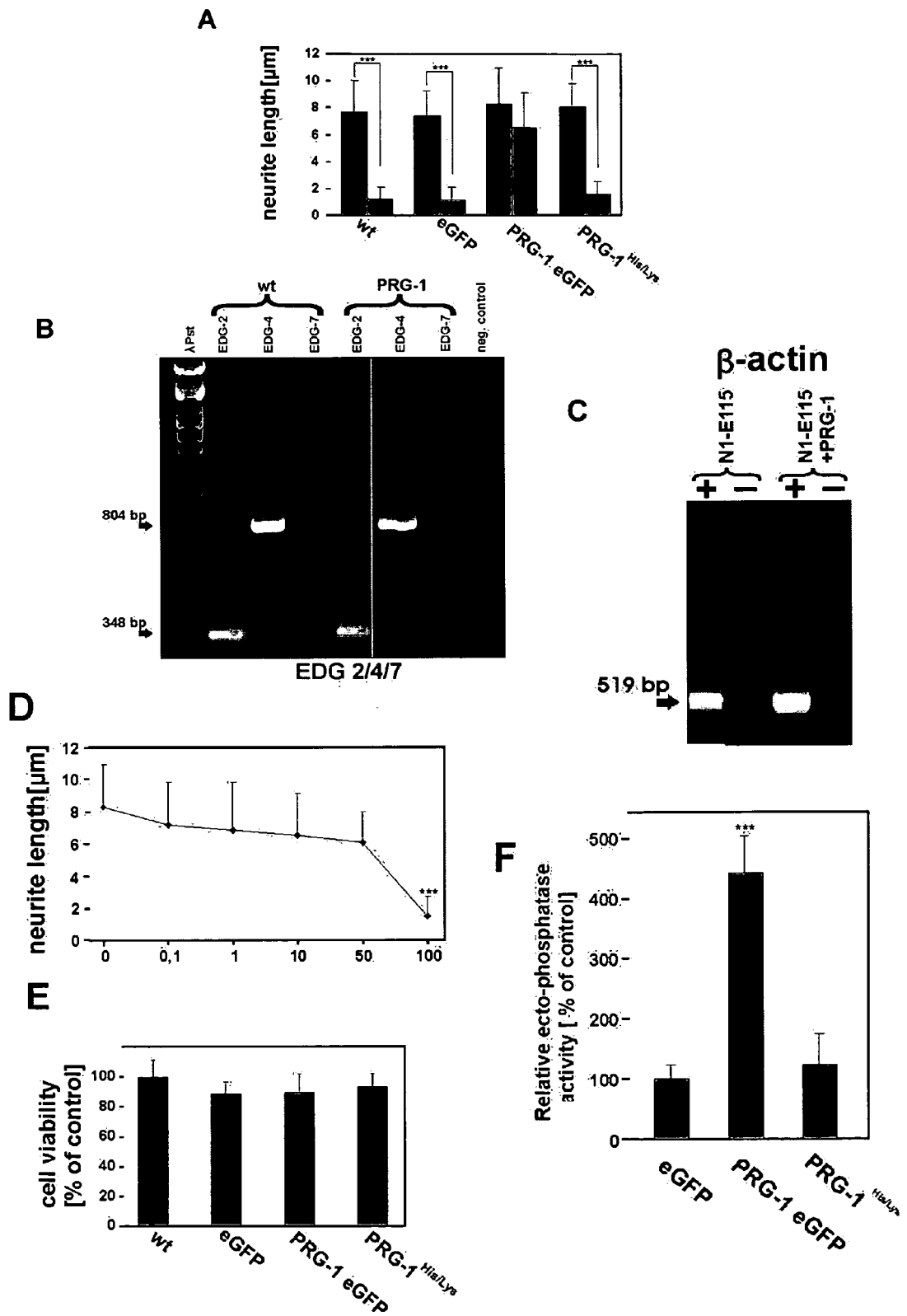

FIG. 12 Panel A shows the quantification of the results shown in FIG. 11 and of a similar experiment performed with wild type N1E-115 cells (wt). Panel B shows the results of RT-PCR using LPA receptor specific primers to assess LPA receptor expression in wild type N1E-115 cells (wt) or PRG-1 transfected N1E cells (PRG-1). Panel C shows the results of RT-PCR using β-actin specific primers to assess β-actin expression in wt N1E-115 cells and in PRG-1 transfected cells. Panel D shows a dose response of LPA treatment on neurite length of PRG-1 overexpression cells. Panel E shows cell viability of N1E-115 cells 48-72 h after transfection. Panel F shows the phosphatase activity of intact cells overexpressing eGFP, PRG-1-eGFP, and PRG-1$^{His/Lys}$.

Figure 13:
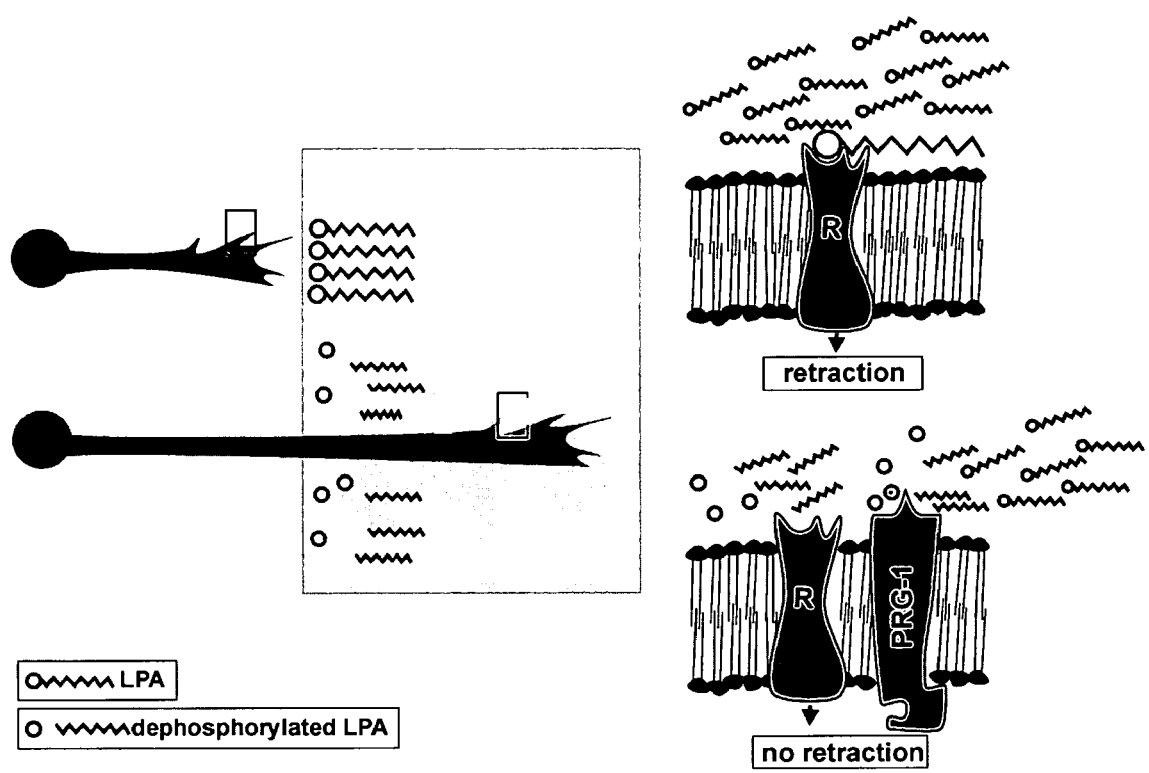

FIG. 13 Schematic diagram of the proposed axon growth mechanism in a lipid phosphate lipid rich environment. "R" means receptor mediating a retraction signal.

Figure 14:
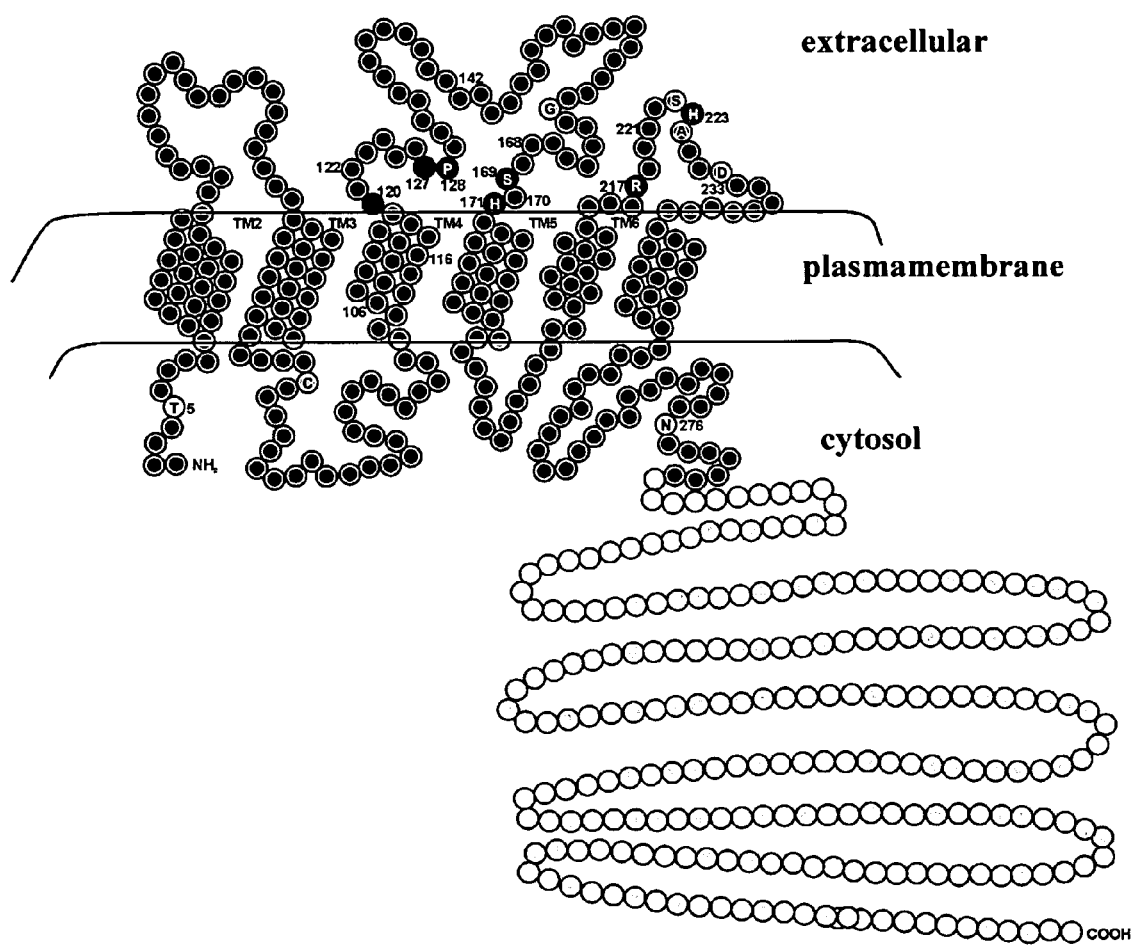

FIG. 14 Depicts the proposed structure of the human PRG-1 wherein those parts presumed to be arranged on the extracellular surface inserted in the plasma membrane and protruding into the cytoplasm are shown.

Figure 15:
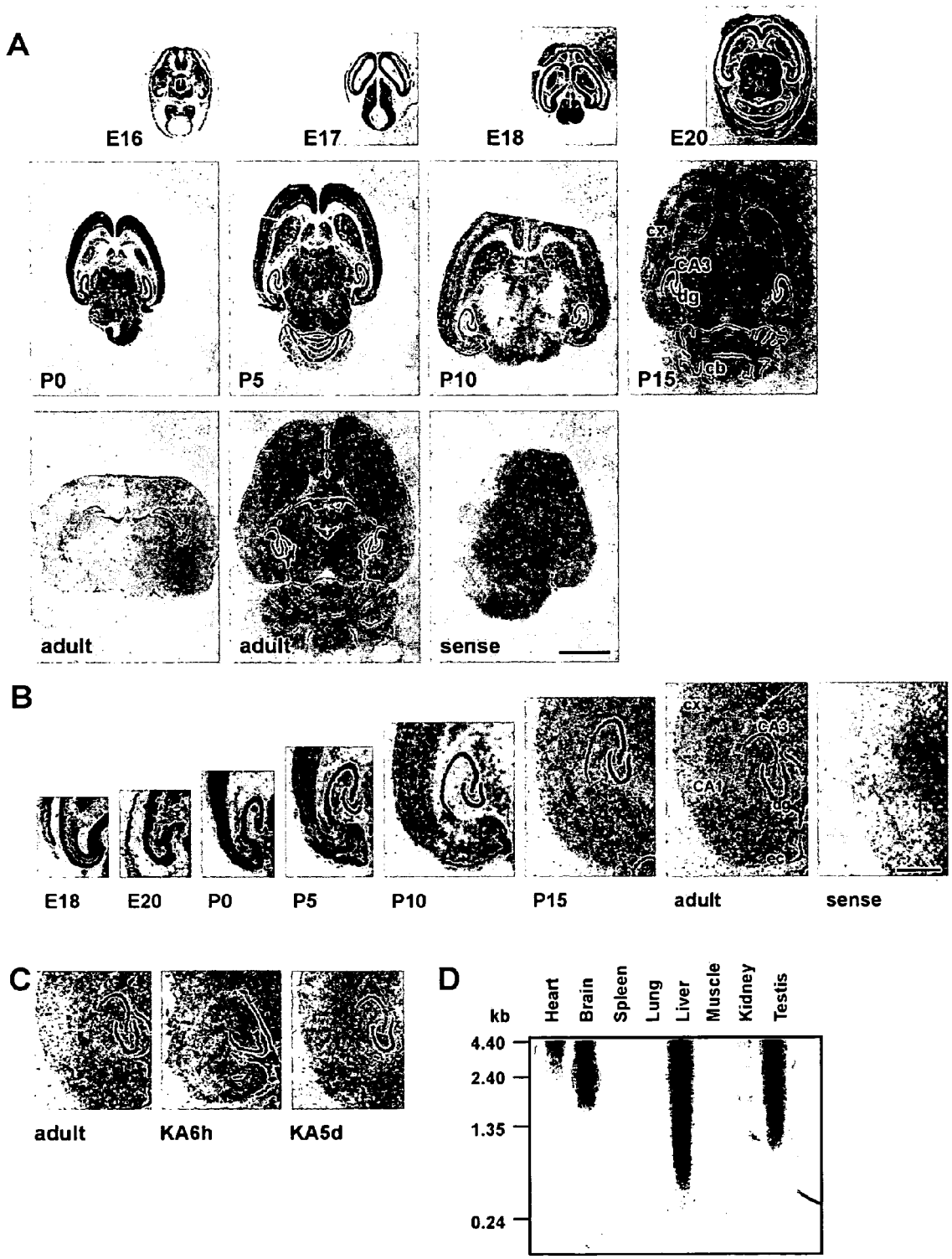

FIG. 15 Expression pattern of PRG-3 mRNA in the developing rat brain detected by in situ Northern blot. Panels A-C depict the in in situ staining of rat brain sections at various developmental stages in which E18 and E20 depict stains from embryonic days 18 and 20, and P0, P5, P10, P15 stains post partum at days 0, 5, 10, and 15. The scale bar in A equals 1.8 mm and in panel B 400 µm. Panel D depicts the Northern blot analysis of RNA derived from different tissues of the adult rat.

Figure 16:
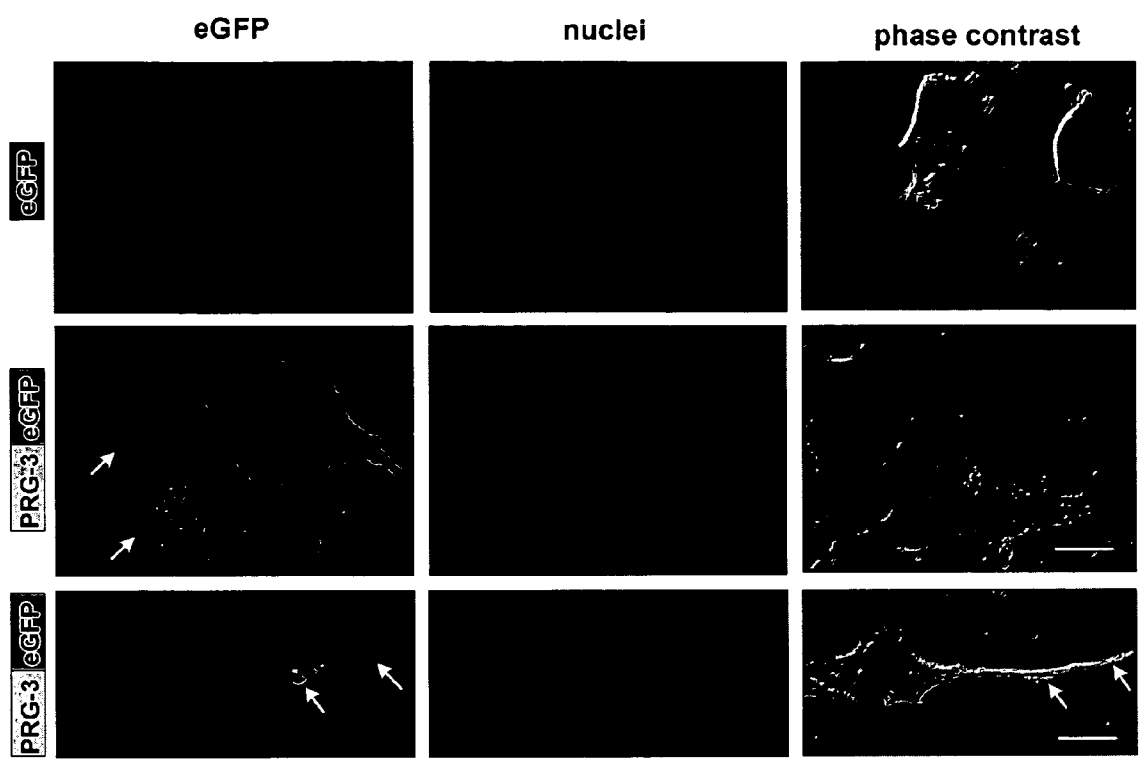

FIG. 16 Depicts the cellular localization of PRG-3-eGFP fusion proteins. PRG-3 is visible predominantly in the plasma membrane and in neurite extensions. The upper row depicts cells transfected with the peGFP-N1 reporter vector alone and the second and third row cells transfected with a pPRG-3-eGFP fusion construct. The scale bar in the second row represents 2 µm and 5 µm in the third row.

EXAMPLES

1. Isolation of PRG-1

Animals and Surgery

All animals were housed under standard laboratory conditions, and the surgical procedures were performed in agreement with the German law (in congruence with 86/609/EEC) for the use of laboratory animals. All efforts were made to minimize the number of animals used, and all surgical procedures were performed under sufficient anesthesia to minimize animal suffering. The experimental procedures are described in detail in Bräuer et al (2001) FASEB J. 15:2689-2701.

Substraction cDNA Library and Differential Screening

The SMART cDNA technology from Clontech was used to generate high yields of full-length, double-stranded cDNA from adult, control and lesioned hippocampus rat RNA. To develop the substraction library, the Clontech PCR-Select cDNA substraction Kit (Heidelberg, Germany) was used.

Each clone was dotted in duplicates on Hybond N filters (Amersham, Germany) and screened with randomly radioactively labeled cDNA (Prime-A-Gene, Promega, Germany) from adult non-lesioned and lesioned hippocampus.

2. Analysis of the Sequence of PRG-1

Similar to other members of LPP-family a hydrophobicity analysis of PRG-1 predicts 6 N-terminal membrane-spanning regions with a highly conserved phosphatase domain. The analysis was done using the DNAsis for Windows Version 2.6; Hitachi Software Engineering Co. Hydrophobicity Analysis Submenue using the Kyte & Doolittle algorithm with all settings set to default values. However, unlike the other members of this family the second type of the protein consists of a long hydrophilic domain of around 400 amino acids (FIG. 2). According to the structural models of LPP orientation in the membrane, this C-terminal extension is positioned on the cytoplasmatic site and might thus play a role as a regulatory or signal transduction domain. Beside the homology of the N-terminal part of the PRG-1 to other members of the LPP-family such as LPP-1 and the *Drosophila* cell migration modulator Wunen, GenBank searches revealed only one other related gene (genomic DNA sequence: GenBank acc. # NP_011255.11) for which we cloned the complete cDNA sequence and named it PRG-2. This gene shares the same C-terminal extension with partial sequence homology. Thus, these genes represent a novel distinct subclass of the LPP-1 family. Amino acid residues which have been shown to be essential for ecto-enzyme activity in the LPP-1 class of proteins are conserved in PRG-1 N-terminal sequences (FIG. 1). Database analysis of the C-terminal domains did not detect any significant similarities to any other protein or any other matches with known conserved domains (using ProDom and Swiss-Prot databases). A GenBank search for orthologous proteins showed that both genes are highly conserved in mammals (human/mouse>93%), and partial EST sequences indicate orthologous proteins in *Xenopus* and Zebrafish, whereas no significant homology for the C-terminal part could be found in the *Drosophila* or other invertebrate genome.

3. Northern Blot Analysis of PRG-1 Expression

20 μg of total RNA from six adult control and six 1 dal animals were loaded on a 1% agarose gel containing formaldehyde, transferred to Hybond™—Ns (Amersham Life Science, UK) and crosslinked by ultraviolet irradiation. As a probe for PRG-1, the full length cDNA clone as well as the C-terminal coding region was used. As probe for β-actin (as control for mRNA integrity and amounts of mRNA loaded), a cDNA fragment amplified by RT-PCR was used. Primer for the amplification of the control gene β-actin were: β-actin 5' (5'-CAC CAC AGC TGA GAG GGA AAT CGT GCG TGA -3', SEQ ID No. 25) spanning bases 2395-2424, and β-actin 3'-primer (5'-ATT TGC GGT GCA GCA TGG AGG GGC CGG ACT-3', SEQ ID no. 26) complementary to bases 3095-3124, with an amplificate length of 520 bp for rat β-actin cDNA (GenBank accession no. J00691). PCR was performed in 25 μl final volume containing 1 mmol/l dNTPs (Pharmacia Biotech, Germany), 2.5 units Taq Polymerase (Perkin Elmer, USA) 2.5 μl 10× buffer including 2.5 mol/l $MgCl_2$ (Perkin Elmer, USA), 10 μmol/l each primer and 1 μl cDNA using a Thermo-Cycler PTC-100 (MJ Research, Inc., USA). The cycle program was: 95° C., 2 min; 35×[94° C., 30 s; 70° C., 30 s 72° C., 2 min] and 10 min, 72° C. Both probes were labeled with the Prime-a-Gene Labelling System (Promega, USA) and [$^{32}$P] dCTP (DuPont NEN, USA). Hybridization was performed in 10 ml hybridization solution (250 mmol/l sodium-phosphate, pH 7.2, 7% SDS, 0.5 mmol/l EDTA, 1% BSA) at 60° C. for 12 h. The membrane was washed in 2×SSC at RT, 0.2×SSC at RT, and 0.2×SSC at 40° C. for 30 min each. Membranes were exposed to Kodak X-OMAT AR X-ray films at −80° C. for 12 h, using an intensifying screen. Northern blot analysis revealed one distinct band which migrated around 5.5 kb. Expression of this mRNA was CNS-specific with the exception of a weak expression in testies (see FIG. 3). Thus, PRG-1 is a novel vertebrate specific protein selectively located in the brain with putative phosphatase function.

4. In situ Hybridization Analysis of PRG-1 Expression

For hybridization, an antisense oligonucleotide (5'-GCA GAG GTC TGA ATT CTA GTG TCT ATC GTT ATA GTT CCT TAA CAG TGT GGG-3', SEQ ID No. 27) complementary to bases 425-475 of a rat EST cDNA clone (GenBank acc. AW 526088.1) was used. The oligonucleotide was synthesized by Metabion (Munich, Germany). The specificity was confirmed by a BLAST GenBank search to rule out cross-hybridization to other genes. The protocol was used as described by Bräuer et al (2002) supra.

The in situ hybridization analysis highlighted the tight regulation of PRG-1 transcription in the developing hippocampus. At embryonic day 16 (E16), no PRG-1 transcripts could be detected in the brain (FIG. 4, panel B). An expression signal first appears at day 19 (E19) in the subventricular zone and specifically in the hippocampal anlage, whereas other cortical regions did not show PRG-1 expression (FIG. 4, panel D). From postnatal stages on, PRG-1 mRNA is present in the hippocampus and in the entorhinal cortex throughout adult stages (see FIG. 4, panels E-J). In the dentate gyrus, a region bearing postnatally developing granule cells, weak PRG-1 mRNA expression is found in the infrapyramidal blade at P0, whereas the later developing suprapyramidal blade first showed expression signals at P5. This expression pattern remains unchanged during maturation, however, a reduced expression is apparent in the adult brain.

5. PRG-1 mRNA Expression After Entorhinal Cortex Lesion

The treatment of the animals, the surgery the construction of the subtraction cDNA library and the screening were carried out as described in example 1. The in situ hybridization was carried out as described in example 4. PRG-1 is upregulated one day after lesion (dal) and peaks at 5 dal in the ipsilateral hippocampus (gcl=37%, hilus 300%, CA1=100%, CA3=60%). The contralateral hippocampus (maximum by 1 dal, gcl=16%, hilus=200%, CA1=59%, CA3=46%), as well as the ipsilateral cortex, shows a strong upregulation of PRG-1 mRNA (maximum by 1 dal 83%) (see FIG. 5).

6. Transfection of a PRG-1-eGFP Construct

Antibody Generation and Immunohistochemistry

To design a peptide antibody against PRG-1, a sequence in the hydrophilic C-terminal region was used. The peptide ($NH_2$-CVGVNGDHHVPGNQ-COOH, SEQ ID No. 28), representing amino acids 490-507 of the PRG-1 rat sequence (SEQ ID No. 9), was synthesized by BioGenes (Berlin, Germany). The amino-terminal cysteinyl residue, which is not part of the PRG-1 sequence, was included for conjugation of the peptide to a carrier protein. The peptide was conjugated through the cysteinyl sulfhydryl to maleimide activation (keyhole limpet hemocyanin). Rabbits were immunized by BioGenes. The specificity of the peptide antibody was further tested on Western blot and on brain sections by blocking via peptide incubation prior to adding the antiserum. The protocol for the immunohistochemistry is described in detail by Bräuer et al (2001) Neuroscience 102:515-526.

Western Blot Analysis

For Western Blot analysis, rat adult and 5 dal hippocampus extracts were separated on a 12% SDS/PAGE and electroblotted to nitrocellulose membranes (Millipore, Germany). All incubation was done overnight at 4° C. in PBST. The PRG-1 antiserum was used at a 1:2000 dilution. Secondary anti-rabbit antibody coupled with horseradish peroxidase was used at a 1:5000 dilution, and visualized by incubation in ECL detection reagents (Amersham Pharmacia, Germany). The protocol for the immunocytochemistry is essentially the same as described in detail in Bräuer et al. (2001) supra].

The immunoblot in FIG. 6D showed a single band obtained by incubation with the anti-PRG-1 antiserum. The absence of specific signal in the preimmune serum prior to immunization is noteworthy. Immunoblots from total protein extracts of adult control and deafferentiated hippocampus shown in FIG. 7C demonstrated an increase five days after lesion (5 dal). Data represents three separate experiments in each group. Statistical difference is marked with an asterisk (mean±S.D.), *P<0.05; Mann-Whitney-U-test.

Subcellular Localization

PRG-1 tagged with the eGFP reporter gene was used to identify the subcellular localization. Golgi apparatus was visualized with the cell tracker BODYPY ceramide (Molecular Probes, Netherlands). The staining protocol was obtained from molecular Probes.

The transfection studies using a PRG-1 construct tagged with a eGFP reporter gene revealed that PRG-1 protein was processed in COS-7 cells through the Golgi apparatus (data not shown) to its final localization in the plasma membrane of small processes (FIG. 6, panel A). To localize the PRG-1 proteins in vivo an antiserum against a peptide from the cytoplasmic C-terminus of PRG-1 was raised. This antiserum specifically stained transfected COS-7 cells, which expressed PRG-1-eGFP fusion proteins (FIG. 6, panel A-C) and detected a specific band in Western blot analysis (FIG. 6, panel B). Both the immunostaining and Western blot signal could be blocked by specific peptide incubation prior to the addition of antiserum (data not shown). The fluorescence of the labeled entire-PRG-1 peptide antibody and the fluorescence of the eGFP part of the fusion protein colocalized in COS-7 cells and in the processes (see white arrows in panels A-C of FIG. 6).

7. Expression Analysis by RT-PCR

Tissue from the retraction assays, E16 and P0 explants and N1E-115 cells were used for mRNA isolation and as templates for RT-PCR. cDNA from testis was used as a positive control. The MidiMACS mRNA Isolation Kit (Miltenyi Biotec, Germany) was used to isolate mRNA from the explants or cells. Reverse transcription was performed as described by Bräuer et al. (2000) Hippocampus 10:632-644. PCR was performed with the following primers: PRG-1-5'-primer (5'-CTA GGC TTG TAG CTG TGG GGA ATT TC-3', SEQ ID No. 29), spanning bases 896 bp-921 bp, and PRG-1-3' primer (5'-TCA ATC CTT ATA AGC CCG TGT G-3', SEQ ID No. 30) complementary to bases 2202 bp-2225 bp with an amplification length of 1329 bp of the PRG-1 cDNA (SEQ ID No. 21). For amplification of the EDG receptor cDNA, the primer EDG-2-5' primer (5'-GAA CTT TGC GAG TGA GCT GG-3', SEQ ID No. 31), spanning bases 836 bp-855 bp, and EDG-2-3'primer (5'-TGC GGA GAG CTT TAA CCT CC-3', SEQ ID NO. 32), complementary to bases 1165 bp-1184 bp with an amplification length of 348 bp of the EDG-2 cDNA (GenBank accession no. NM010336), the primer EDG-4-5'primer (5'-CCT ACC TCT TCC TCA TGT TC-3', SEQ ID No. 33), spanning bases 344 bp-363 bp, and EDG-4-3'primer (5'-TAA AGG GTG GAG TCC ATC AG-3', SEQ ID No. 34), complementary to bases 1199 bp-1148 bp of the EDG-4 cDNA (GenBank accession no. NM020028), the primer EDG-7-5'primer (5'-GGA ATT GCC TCT GCA ACA TCT-3', SEQ ID No. 35), spanning bases 673 bp-693 bp, and EDG-7-3'primer (5'-GAG TAG ATG ATG GG TTC A-3', SEQ ID No. 36), complementary to bases 1096 bp-1054 bp of the EDG-7 cDNA (GenBank accession no. NM022983). PCR was performed using a Thermo-cycler PTC-100 (MJ Research, Inc.) in 25 µl final volume containing 10 µmol/l dNTPs (Pharmacia, Germany), 2.5 units Taq Polymerase (Stratagen, Germany), 2.5 µl 10× buffer including 2.5 mol/l $MgCl_2$ (Stratagen, Germany), 10 µmol/l of each primer, and 2 µl of each cDNA for all molecular analysis. For all EDG receptors, as well as for PRG-1 amplification, the cycle program was: 2 min at 95° C., 40×(94° C., 30 sec; 52° C., 30 sec; and 72° C., 1 min), and 5 min at 72° C. Amplification of β-actin cDNA was performed as described by Bräuer et al. (2000) Hippocampus 10:632-644.

8. Immunocytochemical Staining of Rat Hippocampus

The antibody described in experiment 6 was also used for the immunocytochemical staining and Western blot analysis. For Western blot analysis, rat adult and 5 dal hippocampus extracts were separated on a 12% SDS/PAGE and electroblotted to nitrocellulose membranes (Millipore, Germany). All incubation was done overnight at 4° C. in PBST. The PRG-1 antiserum was used at a 1:2000 dilution. Secondary anti-rabbit antibody coupled with horseradish peroxidase was used at a 1:5000 dilution, and visualized by incubation in ECL detection reagents (Amersham Pharmacia, Germany). The protocol for the immunocytochemistry is essentially the same as described in detail in Bräuer et al., 2001 (FASEB J, 15, 2689-2701). The immunocytochemical staining of rat hippocampus revealed that PRG-1 was specifically expressed in neurons (see FIG. 7, panel A) and in particular pyramidal neurons are labeled in the CA1 and CA3 region, polymorphic cells are stained in the hilus and granule cells of the dentate gyrus are also immunopositive. However, the outer molecular layer, the termination zone of afferents from the entorhinal cortex (Skutella T. and Nitsch R. (2001) Trends. Neuroscience 24:107-163) showed no PRG-1 positive fibers (FIG. 7, panel A). Conversely five days after entorhinal cortex lesion, a clear immunoreactive PRG-1 positive band appeared in the denervated outer molecular layer (FIG. 7, panel B). Western blot analysis revealed a 50% increase in PRG-1 expression in the denervated hippocampus (FIG. 7, panel C). PRG-1 immunostaining highlighted single axonal processes in the outer molecular layer which form terminal branches (FIG. 8, panel A). The higher magnification of an area from the immuno stained axons showed that PRG-1 is indeed localized in the growth cone-like axon structures in the denervated zones of the hippocampus (see FIG. 8, panel B).

Subcellular Localization

PRG-1 tagged with the eGFP reporter gene was used to identify the subcellular localization. Golgi apparatus was visualized with the cell tracker BODYPY ceramide (Molecular Probes, Oregon). The staining protocol was obtained from Molecular Probes.

9. Effect of PRG-1 Expression on the LPA Response of Neurons

LPA Induced Neurite Retraction in Explants

Entorhinal explants from E16 and P0 rat pups were obtained from timed-pregnant Wistar rats and were cultivated as described (N. E. Savaskan (2000) Eur. I. Neurosci 12:1024-1032). In brief, entorhinal cortex was carefully dissected from the hippocampal anlage and the meninges were removed. Explants were gently transferred with a fire-polished Pasteur pipette into 12-well plates and cultivated on baked glass cover slides coated with laminin and poly-L-lysin (25 μg/ml and 10 μg/ml, respectively) in culture medium containing selenium-defined fetal bovine serum [5%] (N. E. Savaskan et al (2000) FASEB J. e-published) (Neurobasal medium plus 25 μg/ml Penicillin/Streptomycin; B-27 supplement). After 24 h, culture medium was exchanged and cultivation was further performed in serum-free Neurobasalmedium for 20 h. Serum-starved explants were treated with 100 nmol/l oleoyl-LPA (5 mmol/l stock solution in ultra-filtrated water) for 10 min or with vehicle (0.9% NaCl) and then fixed in 4% paraformaldehyde for 20 min. For F-actin staining, fixed tissues were incubated with TRITC-phalloidin (0.1 μg/ml, Sigma, Germany) for 40 min, followed by incubation with HOECHST 33258 dye (1:20,000, Sigma, Germany) for 5 min at room temperature. After three washing steps in PBS, explants were coverslipped with ImmunoMount (Merck, Germany) prior to analysis. Images were taken with a CCD camera on an Olympus BX-50 microscope and quantification was performed using the Meta Morph analysis system (Universal Imaging, PA). For statistical analysis Statview II was used (Abacus, USA).

A dose response of LPA neurite length of E16 and P0 explants was done as described above, however, with 0, 0.1, 1.0 and 10 μmol/l.

Entorhinal explants obtained at day 16 (E16) do not express PRG-1 while postnatal explants (P0) express PRG-1 (see FIG. 9, panel A). In contrast, the LPA-specific receptors EDG-2/4/7 were equally expressed in both embryonic and postnatal explants (see FIG. 9B). The control RT-PCR with β-actin showed the integrity of the RNA from E16 and P0 cells. Both embryonic and postnatal explants grow equally well under serum-free culture conditions and show long extending axons (see FIG. 9, panels D and F). However, their response to LPA differed dramatically (see FIG. 9, panels E and G). Whereas application of 100 nmol/l LPA led to rapid neurite retraction in embryonic entorhinal explants (E16; n=20, compare panel D to panel E), postnatal explants (P0; n=22, compare panel F to panel G) did not differ significantly from vehicle treated control cultures. Thus, postnatal entorhinal axons expressing PRG-1 are resistant to LPA-induced neurite retraction. The amount of retraction observed in panels D-G is quantified in FIG. 10, panel A. The dose response is shown in FIG. 10, panel B.

10. Differential Effect of PRG-1 and PRG-1 Mutant on LPA-induced Neurite Retraction Site-directed Mutagenesis of PRG-1$^{HIS/LYS}$ The rat PRG-1 full length clone was amplified by Marathon PCR (Clontech, USA) from adult rat hippocampus RNA (SEQ ID No. 17). For transfection studies, the full length PRG-1 coding sequence was fused to EGFP (pEGFP-N1 vector Clontech, USA). The PRG-1$^{His/Lys}$ exchange mutant at the catalytic histidine (His-252) was introduced in the same protein fusion vector by site specific mutagenesis (CAT to AAG).

LPA Induced Neurite Retraction and Protection in N1E-115 Cells

N1E-115 mouse neuroblastoma cells (ATCC: CRL-2263) were routinely grown in DMEM medium supplemented with selenium-defined fetal bovine serum (10%). The cells were seeded on baked glass cover slides at a density of 10,000 cells/cm². The next day, cells were transfected with the cationic lipids procedure (FuGene6, Roche, Germany) and cultivated for 24 h. Serum-starvation was performed for 20 h in DMEM medium, followed by treatment with 10 μmol/l oleoyl-LPA or vehicle (0.9% sodium chloride) (K. Jalink et al (1993) Cell Growth Differ. 4:247-255). After 10 min, cells were fixed in 4% paraformaldehyde for 20 min at room temperature and further analysis processed as described above. Images were taken with a CCD camera on an Olympus BX-50 microscope. Quantification was performed with the Meta Morph analysis system (University Imaging, PA). For statistical analysis Statview II was used (Abacus, USA). The effects of transfection on cell viability were analysed by MTT assay and propidium iodide staining (Savaskan N. E. et al. (2002) FASEB J. 17:112-114).

N1E-115 cells are uniformly sensitive to LPA-induced growth cone collapse (see FIG. 11 and compare first row of panels versus second row of panels). This is also confirmed by phalloidin staining (K. Jalink et al, (1994) J. Cell Biol. 126: 801-810) which showed actin polymerization upon PRG-1 overexpression, however, led to a resistance of N1E-115 cells to LPA-induced growth cone collapse and also prevented LPA-induced actin-polymerization (see FIG. 11, third row of panels). The mutation of the conserved catalytic histidine (His-252) to a lysine (PRG-1$^{His/Lys}$) a change which has been shown to completely abolish enzymatic function of the catalytic center of LPP-1 (N. Zhang, et al. (1997) supra) no longer prevented LPA-induced retraction of processes as achieved by the wt-construct. This shows that the conserved enzymatic domain of the LPP-1 family is necessary for PRG-1 function in attenuating LPA-induced neurite retraction. The results of the experiments are quantified in FIG. 12, panel A. The transfection, however, had no effect on the expression of the LPA-receptors EDG-2/4//7 (see FIG. 12, panel B). The control for the integrity of the RNA tested by RT-PCR is shown in FIG. 12, panel C. The resistance against CPA-induced growth cone collapse achieved by PRG-1 overexpression could only be overcome by a 10-fold increase of LPA applied to the culture (FIG. 12, panel D).

11. Ectophosphatase Activity in PRG-1 Transfected N1H-115

The assay procedures used were adapted from those described in Imai et al. (2000) J. Clin. Endocrinol. Metab 85:3370-3375 and Hooks S. B. et al. (2001) J. Biol. Chem. 276:4611-4621. Briefly, transfected cells were harvested after serum-free cultivation for 20 h by scraping in lysis buffer (containing 20 mmol/l HEPES pH 7.4, 1 mmol/l NaHCO$_3$, 500 μmol/l DTT, 1 mmol/l EGTA) and sonicated with two strokes (Bandolin GM 70, Germany). After centrifugation at 800×g, the supernatant was diluted in lysis buffer and centrifuged at 100,000×g for 1 h. Alternatively, the supernatant was topped on a sucrose step gradient (50% and 5%) and centrifuged at 100,000×g for 1 h (Savaskan, N. E. et al. (2000) Eur. J. Neurosci. 12:1024-1032. The resulting pellet and interphase, respectively, were re-homogenized and centrifuged again at 100,000×g for 1 h. The crude membrane pellet was re-suspended in reaction buffer (50 mmol/l HEPES pH 7,5; 1 mmol/l EGTA) and protein concentration was determined spectroscopically by Bradford protein assay (Amersham, Germany). Assessment of LPA metabolism was performed with exogenous $^3$H-oleoeyl-LPA (Perkin Elmer, Germany) measuring $^3$H-oleoeyl-glycerol production. Briefly, 10-25 μg membrane proteins were pre-warmed to 37° C. in reaction buffer and reactions were started by the addition of 10 μmol/l $^3$H-oleoeyl-LPA. The reaction was allowed to proceed for 5-30 min at 37° C. and stopped with the addition of 2.5 vol acidified methanol and 1.5 vol chloroform. After two-phase separation, the chloroform phase was dried under N$_2$ and applied to silica gel matrices (Machery Nagel, Germany).

Plates were developed in chloroform-aceton-acetic acid (90:10:1). All fractions of dried plates were scintillation counted and compared with authentic standards (LPA, 1-monoolein, 1,2-monoolein, oleic acid). All experiments were performed in triplicate. The ecto-phosphatase assay in intact cells was determined as described above. $^3$H-LPA was added to the serum-free medium and the reaction was allowed to proceed for 5-60 min. The reaction was stopped by adding 2.5 vol acidified methanol and 1.5 vol chloroform to the supernatant. The radioactivity was determined in the lipid fraction as described above.

The results from three independent sets of experiments are shown in FIG. 12, panel F (one set with n=40 for each group in the outgrowth assay). PRG-1-eGFP showed essentially the same ecto-phosphatase activity as the wt PRG-1 construct. Statistical differences from controls are marked with an asterisk (mean±S.D.), ***P<0.001; two-tailed t test with Bonferroni correction for multiple comparisons.

The extracellular LPA-degradation achieved by transfected N1E-115 cells revealed a 5-fold increase in ecto-phosphatase activity of wildetype PRG-1 transfectants when compared to eGFP transfection alone (FIG. 12, panel F). Moreover, point-mutation in the conserved catalytic domain by His/Lys exchange led to a 95% decrease of ecto-phosphatase activity (FIG. 12, panel F). These findings show that PRG-1 has ecto-phosphatase activity which is conveyed by a conserved enzymatic domain present in the LPP-1 family, and necessary for attenuating LPA-induced neurite retraction. In addition transfection of the PRG-1 construct into N1E-115 cells did not prevent CPA-induced retraction of processes as achieved by the wt-constructs, whereas cell viability was unaffected (see FIG. 12, panel E).

Thus the ecto-phosphatase activity of PRG-1 was shown by two independent experiments: a) transfection of a mutant construct into N1E-115 cells did not prevent LPA-induced retraction of processes as achieved by transfection of wt construct and b) the transfection of the wt construct led to a 5-fold increase in ecto-phosphatase activity, if compared to cells transfected with a control vector.

12. Model of Axon Growth Mechanism

FIG. 13 shows a diagram of the proposed axon growth mechanism in a phospholipid rich environment. Axons that are sensitive to repulsive phosphor lipid but do not express PRG-1 are unable to cross a phosphor lipid-rich barrier. In contrasts PRG-1 expressing neurons can grow through a phosphor lipid rich zone by local depleting the extracellular pool of repulsive phosphor lipids acting as ligands on EDG-receptors. This way, PRG-1 may regulate the activation of EDG-receptors and thereby modulate axonal outgrowth.

13. Northern Blot Analysis of PRG-3 Expression

The full coding region of PRG-3 was amplified by PCR and the product was p32-dCTP labelled by T4 kinase reaction. Hybridization was performed overnight at 68° C. and exposure followed for 20 h. The multi-tissue Northern blot analysis of rat PRG-3 mRNA shows a single 2.4 kb band in brain and liver. Slightly lower bands are also present in kidney and testis as depicted in FIG. 15.

14. In situ Hybridization Analysis of PRG-3 Expression

For hybridization, we used two antisense oligonucleotides which both gave essentially the same hybridization signal: 5'-GCA GAG GTC TGA ATT CTA GTG TCT ATC GTT ATA GTT CCT TAA CAG TGT GGG-3' (SEQ ID NO. 37) and 5'-CAT CCT TCT GTA GTA GCT TTC TGC CTC TGC CTC CAC TTC TCT CT-3' (SEQ ID NO. 38) complementary to rat PRG-3 sequence (SEQ ID NO. 23). The oligonucleotide was synthesized by Metabion (Munich, Germany). The specificity was confirmed by a BLAST GenBank search to rule out cross-hybridization with other genes. We used the protocol as previously described (Brauer et al., 2001, supra).

Kainate Administration and Assessments of Seizure Activity and Neuronal Cell death in vivo Six rats, weighing 200-300 g, were weight-paired (±10 g per pair). These animals received a single i.p. injection of kainic acid (10 mg/kg bodyweight; from Ocean Products Int., Canada) freshly dissolved in 0.9% saline. Behavior was then observed constantly for 24 hr via video time lapse recordings. Controls received a single i.p. injection of saline in the same volume or were not treated. Severity of seizures was scored for 4 h after kainate injection using the classification of Zhang et al. Twenty-four hours after kainate injections, rats were killed and brains were harvested. Coronal brain sections were cut on a freezing microtome with 20 μm thickness and stained with cresyl violet and acid fuchsin. Nissl-positive undamaged neurons were counted in five coronal brain sections per animal (sections were chosen by unbiased sampling), and the mean number of cells per section were determined such that the value obtained for each rat represents an average total number of neurons counted per section (250 μm by 250 μm square in the middle of the CA1 region). Counts were performed by an investigator blind to treatment status.

The hybridization was carried out as described above. At embryonic day 16 (E16) a hybridization signal for PRG-3 can be detected in the hippocampal anlage, thalamus, and in the olfactory bulb. At perinatal stages (E20-P0), a strong hybridization signal is found in the cortex and hippocampus except the dentate gyrus (dg). FIG. 15, panel B shows a higher magnification of the hippocampus. Note that in the dentate gyrus the first hybridization signal occurs at postnatal day β (P0). FIG. 15, panel C shows that adult, PRG-3 transcripts can be found in all principal layers of the hippocampus. A rapid PRG-3 repression is found six hours after kainic acid application. Five days after kainic acid application, PRG-3 mRNA shows comparable levels to the adult non-treated controls. CA, cornu ammonis; cb, cerebellum; Cx, cortex; dg, dentate gyrus; KA, kainic acid. Scale bar in A, is 1.8 mm and in B, 400 μm.

15. Effect of PRG-3 Expression on Neurons

N1E-115 cells were transfected with peGFP-N1 reporter vector alone or with a pPRG-3-eGFP fusion construct as described above. As can be seen from the second and third row the eGFP is mainly found in the cytosol whereas PRG-3-eGFP is localized in the plasma membrane and in neurite extensions (arrows). Note that PRG-3-eGFP expression induce a spreading-like phenotype and long extensions. Scale bar in the second row of panels represents 2 μm; in the third row of panels 5 μm.

16. PRGs as a Prognostic Marker for Cancer

To test the hypothesis, that PRG-1 might be a prognostic marker for cancer diagnostics, differential human prostatic tumors were screened by means of PCR and immunocytochemistry. Adenocarcinoma is the most malignant neoplasia of human males in western world. Samples from 10 matched pairs of microdissected prostate tissue (tumor and normal) were frozen and sections were made. A transcription analysis was performed using RNA preparations from these samples. It was found, that in normal prostate tissue almost no PRG-1 transcript or protein could be detected. In tumor tissue with Gleason tumor grades 1-3, which is characterized as low-grade tumors, we found only 2 PRG-1 positive samples.

Analysis of high-grade tumors (Gleason grade 4-5) revealed in 80% of the cases a significant PRG-1 upregulation. Therefore, PRG-1 is an independent prognostic marker for high-grade prostate tumors in human males.

17. PRG as a Prognostic Marker for Alzheimer's Disease

Alzheimer's disease is characterized by intracellular neurofibrillary tangle formation formed by tau-based paired helical filaments (PHF) and by extracellular beta-amyloid plaques. The degree of Alzheimer dementia correlates well with the severity of PHF occurrence. These PHF are formed by hyperphosphorylated tau formation. Analysis of brain sections from patients with Alzheimer's disease revealed a reduced PRG-1 expression. To gain insights into the functional role of PRG-1 in Alzheimer's pathology we used an established cell culture model.

Comparing neurons overexpressing PRG-1 with control transfected cells revealed an significant reduction of hyperphosphorylated tau protein. Also, using okadaic acid or LPA as known tau hyperphosphorylation induced substances, we found a significantly decrease in hyperphosphorylated tau and PHF formation.

---

The invention claimed is:

1. An isolated protein comprising an amino acid sequence of SEQ ID NO: 1 or an amino acid sequence having at least 95% sequence identity thereto, wherein mutations in the sequences having at least 95% sequence identity are located in a sequence portion selected from the group consisting of:
   a) the N-terminal fragment of 330 amino acids or less, including the catalytic region, and
   b) the C-terminal fragment of 413 amino acids or less, including a regulatory domain, and wherein the protein inhibits neurite retraction in a statistically significant manner in an LPA-induced neurite retraction assay.

2. A pharmaceutical composition for the treatment of neuronal injuries or diseases comprising a protein according to claim 1 and optionally auxiliary substances and/or additives.

* * * * *